(12) United States Patent
Hatchwell et al.

(10) Patent No.: US 11,384,397 B2
(45) Date of Patent: Jul. 12, 2022

(54) METHODS AND COMPOSITIONS FOR DIAGNOSING, PROGNOSING, AND TREATING ENDOMETRIOSIS

(71) Applicant: Population Bio, Inc., New York, NY (US)

(72) Inventors: Eli Hatchwell, Winchester (GB); Peggy S. Eis, Fitchburg, WI (US)

(73) Assignee: POPULATION BIO, INC., New York, NY (US)

(*) Notice: Subject to any disclaimer, the term of this patent is extended or adjusted under 35 U.S.C. 154(b) by 253 days.

(21) Appl. No.: 16/197,593

(22) Filed: Nov. 21, 2018

(65) Prior Publication Data

US 2019/0249252 A1 Aug. 15, 2019

Related U.S. Application Data

(62) Division of application No. 14/538,404, filed on Nov. 11, 2014, now Pat. No. 10,174,376.

(60) Provisional application No. 61/903,286, filed on Nov. 12, 2013.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/142* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,143,854 A | 9/1992 | Pirrung et al. |
| 5,223,409 A | 6/1993 | Ladner et al. |
| 5,288,514 A | 2/1994 | Ellman |
| 5,384,261 A | 1/1995 | Winkler et al. |
| 5,424,186 A | 6/1995 | Fodor et al. |
| 5,445,934 A | 8/1995 | Fodor et al. |
| 5,451,683 A | 9/1995 | Barrett et al. |
| 5,510,270 A | 4/1996 | Fodor et al. |
| 5,527,681 A | 6/1996 | Holmes |
| 5,700,637 A | 12/1997 | Southern |
| 5,744,305 A | 4/1998 | Fodor et al. |
| 5,837,832 A | 11/1998 | Chee et al. |
| 5,858,659 A | 1/1999 | Sapolsky et al. |
| 5,945,334 A | 8/1999 | Besemer et al. |
| 6,040,138 A | 3/2000 | Lockhart et al. |
| 6,207,392 B1 | 3/2001 | Weiss et al. |
| 6,300,063 B1 | 10/2001 | Lipshutz et al. |
| 6,429,027 B1 | 8/2002 | Chee et al. |
| 6,858,394 B1 | 2/2005 | Chee et al. |
| 6,858,412 B2 | 2/2005 | Willis et al. |
| 6,916,621 B2 | 7/2005 | Shah |
| 6,951,761 B2 | 10/2005 | Star et al. |
| 6,969,589 B2 | 11/2005 | Patil et al. |
| 6,977,148 B2 | 12/2005 | Dean et al. |
| 7,011,949 B2 | 3/2006 | Amorese et al. |
| 7,014,997 B2 | 3/2006 | Knoll et al. |
| 7,030,231 B1 | 4/2006 | Craik et al. |
| 7,034,144 B2 | 4/2006 | Van Dongen et al. |
| 7,238,484 B2 | 7/2007 | Pinkel et al. |
| 7,702,468 B2 | 4/2010 | Chinitz et al. |
| 7,910,353 B2 | 3/2011 | Shaffer et al. |
| 7,957,913 B2 | 6/2011 | Chinitz et al. |
| 8,862,410 B2 | 10/2014 | Hatchwell et al. |
| 8,932,993 B1 | 1/2015 | Ward et al. |
| 2002/0012930 A1 | 1/2002 | Rothberg et al. |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0207295 A1 | 11/2003 | Gunderson et al. |
| 2003/0215821 A1 | 11/2003 | Gunderson et al. |
| 2004/0018491 A1 | 1/2004 | Gunderson et al. |
| 2004/0248161 A1 | 12/2004 | Rothberg et al. |
| 2005/0079510 A1 | 4/2005 | Berka et al. |
| 2005/0100893 A1 | 5/2005 | Gunderson et al. |
| 2005/0100932 A1 | 5/2005 | Lapidus et al. |
| 2005/0124022 A1 | 6/2005 | Srinivasan et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |

(Continued)

FOREIGN PATENT DOCUMENTS

| | | |
|---|---|---|
| CN | 103436606 A | 12/2013 |
| WO | WO-9002809 A1 | 3/1990 |

(Continued)

OTHER PUBLICATIONS

Rahmioglu et al; Curr Obstet Gynecol Rep, 2012, vol. 1, pp. 124-137.*
Wang et al; Molecular Psychiatry, vol. 16, pp. 949-959, 2011.*
Korn et al; Nature Genetics, vol. 40, pp. 1253-1260, 2008.*
Hochstenbach et al; Cytogenet Genome Res; vol. 135, pp. 174-202; 2011.*
Olive et al; Annals of the New York Academy of Sciences, 2009, pp. 360-372.*
Alexander Zimprich et al., "A Mutation in VPS35, Encoding a Subunitof the Retromer Complex, CausesLate-Onset Parkinson Disease", American Journal of Human Genetics, vol. 89, No. 1, Jun. 21, 2011, p. 168-175.

(Continued)

*Primary Examiner* — Jehanne S Sitton
(74) *Attorney, Agent, or Firm* — Wilson Sonsini Goodrich & Rosati

(57) ABSTRACT

This document provides methods and materials related to genetic variations associated with endometriosis. For example, this document provides methods for using such genetic variations to assess risk of, or susceptibility of developing or diagnosing endometriosis.

9 Claims, 75 Drawing Sheets

Specification includes a Sequence Listing.

(56) References Cited

U.S. PATENT DOCUMENTS

| | | |
|---|---|---|
| 2007/0207141 A1 | 9/2007 | Lieberburg |
| 2008/0305967 A1 | 12/2008 | Ward et al. |
| 2017/0095456 A1 | 4/2017 | Albertsen |
| 2017/0107563 A1 | 4/2017 | Samusik et al. |

FOREIGN PATENT DOCUMENTS

| | | |
|---|---|---|
| WO | WO-9117271 A1 | 11/1991 |
| WO | WO-9201047 A1 | 1/1992 |
| WO | WO-9210092 A1 | 6/1992 |
| WO | WO-9215679 A1 | 9/1992 |
| WO | WO-9218619 A1 | 10/1992 |
| WO | WO-9220791 A1 | 11/1992 |
| WO | WO-9209690 A3 | 12/1992 |
| WO | WO-9301288 A1 | 1/1993 |
| WO | WO-9322684 A1 | 11/1993 |
| WO | WO-9511995 A1 | 5/1995 |
| WO | WO-9820019 A1 | 5/1998 |
| WO | WO-2006091254 A1 | 8/2006 |
| WO | WO-2006116873 A1 | 11/2006 |
| WO | WO-2009038684 A1 | 3/2009 |
| WO | WO-2010124101 A2 | 10/2010 |
| WO | WO-2015131078 A1 | 9/2015 |

OTHER PUBLICATIONS

Carles Vilario-Guell et al.,"VPS35 Mutations in Parkinson Disease", American Journal of Human Genetics, vol. 89, No. 1, Jun. 1, 2011 p. 162-167.
Coro Paisa'n-Ruiz et al., "Parkinson's Disease and Low Frequency Alleles Found Together Throughout LRRK2", Annals of Human Genetics, Jul. 2009, vol. 73, No. Pt. 4, p. 391-403.
Eli Hatchwell, "Is there a (host) genetic predisposition to progressive multifocal leukoencephalopathy?", Frontiers in Immunology, vol. 6, May 11, 2015 p. 2-3.
Kishore R. Kumar et al., "Genetics of Parkinson disease and othermovement disorders", Current Opinion in Neurology, vol. 25, No. 4 Aug. 2012 p. 466-474.
Subhash Pokharel et al., "High-Throughput Screening for Functional Adenosine to Inosine R A Editing Systems", ACS Chemical Biology, vol. 1, No. 12 Dec. 1, 2006, p. 761-765.
Agami, R. RNAi and related mechanisms and their potential use for therapy. Curr Opin Chem Biol. Dec. 2002;6(6):829-34.
Agarwal et al., Novelty in the target landscape of the pharmaceutical. Nat. Rev. Drug Discovery 12(8):575-6 (2013).
Albertson, et al. Profiling breast cancer by array CGH. Breast Cancer Res Treat. Apr. 2003;78(3):289-98.
Altschul, et al. Gapped BLAST and PSI-BLAST: a new generation of protein database search programs. Nucleic Acids Res. Sep. 1, 1997;25(17):3389-402.
Amarzguioui, et al. Approaches for chemically synthesized siRNA and vector-mediated RNAi. FEBS Lett. Oct. 31, 2005;579(26):5974-81. Epub Sep. 20, 2005.
Antisense Drug Technology: Principles, Strategies, and Applications, Crooke, Marcel Dekker Inc., New York (2001) (Book).
Ausubel, et al. Current Protocols in Molecular Biology. John Wiley & Sons, New York, 1999.
Bennett, C. Efficiency of antisense oligonucleotide drug discovery. Antisense Nucleic Acid Drug Dev. Jun. 2002;12(3):215-24.
Berger, et al., Methods in Enzymology: Guide to Molecular Cloning Techniques vol. 152, Academic Press Inc., San Diego, USA (1987).
Bernstein, et al. Role for a bidentate ribonuclease in the initiation step of RNA interference. Nature. Jan. 18, 2001;409(6818):363-6.
Bier, et al. DNA microarrays. Adv Biochem Eng Biotechnol. 2008;109:433-53.
Bosher, et al. RNA interference: genetic wand and genetic watchdog. Nat Cell Biol. Feb. 2000;2(2):E31-6.
Brummelkamp, et al. A system for stable expression of short interfering RNAs in mammalian cells. Science. Apr. 19, 2002;296(5567):550-3. Epub Mar. 21, 2002.
Chan, et al., Identification of key residues essential for the structural fold and receptor selectivity within the A-chain of human gene-2 (H2) relaxin. The Journal of Biological Chemistry vol. 287, No. 49, pp. 41152-41164, Nov. 30, 2012.
Chen, et al., Identification of small molecule agonists of human relaxin family receptor 1 (RXFP1) by utilizing a homogenous cell-based cAMP assay.
Chen, et al. The evolution of gene regulation by transcription factors and microRNAs. Nat Rev Genet. Feb. 2007;8(2):93-103.
Chen, H. Clinical development of antisense oligonucleotides as anti-cancer therapeutics. Methods Mol Med. 2003;75:621-36.
Chi, et al. Genomewide view of gene silencing by small interfering RNAs. Proc Natl Acad Sci U S A. May 27, 2003;100(11):6343-6. Epub May 2, 2003.
Cole et al., Monoclonal Antibodies and Cancer Therapy, Alan R. Liss (1985) Inc., pp. 77-96.
Current Protocols in Immunology (1994) Coligan et al., (eds.) John Wiley & Sons, Inc., New York, NY.
Current Protocols in Protein Science (CPPS), 2009; (John E. Coligan, et al., ed., John Wiley and Sons, Inc.).
Davis et al., Basic Methods in Molecular Biology, Elsevier Science Publishing, Inc., New York, USA (1986).
Dias, et al. Antisense oligonucleotides: basic concepts and mechanisms. Mol Cancer Ther. Mar. 2002;1(5):347-55.
Elbashir, et al. RNA interference is mediated by 21- and 22-nucleotide RNAs. Genes Dev. Jan. 15, 2001;15(2):188-200.
Estivill, et al. Copy number variants and common disorders: filling the gaps and exploring complexity in genome-wide association studies. PLoS Genet. Oct. 2007;3(10):1787-99.
European Search Report dated Jun. 9, 2015 for European Patent Application No. 14192587.5.
Fan, et al. Illumina universal bead arrays. Methods Enzymol. 2006;410:57-73.
Fassbender, A., et al., "Biomarkers of endometriosis", Fertility and Sterility, 99(4), (Mar. 15, 2013), 1135-1145.
Fire et al. Potent and specific genetic interference by double-stranded RNA in Caenorhabditis elegans. Nature 391 (1998): 806-811.
Freshney, R. I., Culture of Animal Cells: A Manual of Basic Technique. Wiley-Liss; 5th edition (2005).
Fuchs et al., Targetting recombinant antibodies to the surface of *Escherichia coli*: Fusion to a peptidoglycan associated lipoprotein. Bio/Technology, 1991; 9: 1370-1372.
Galfre et al. Antibodies to major histocompatibility antigens produced by hybrid cell lines. Nature 266:550-552 (1977).
Griffiths, et al. Human anti-self antibodies with high specificity from phage display libraries. EMBO J. Feb. 1993;12(2):725-34.
Hay et al. Bacteriophage cloning and *Escherichia coli* expression of a human IgM Fab. Hum Antibodies Hybridomas 3(2):81-85 (1992).
Hegele, et al. "SNP Judgments and Freedom of Association", Arterioscler. Thromb. Vase. Biol. 22 (2002): 1058-1061.
Hoheisel, J. Microarray technology: beyond transcript profiling and genotype analysis. Nat Rev Genet. Mar. 2006;7(3):200-10.
Hunter, C. Genetics: a touch of elegance with RNAi. Curr Biol. Jun. 17, 1999;9(12):R440-2.
Huse, et al. Generation of a large combinatorial library of the immunoglobulin repertoire in phage lambda. Science. Dec. 8, 1989;246(4935):1275-81.
Hutvagner, et al. A microRNA in a multiple-turnover RNAi enzyme complex. Science. Sep. 20, 2002;297(5589):2056-60. Epub Aug. 1, 2002.
Juppner; Bone, vol. 17; 1995, pp. 39S-40S.
Kallioniemi, et al. Comparative genomic hybridization for molecular cytogenetic analysis of solid tumors. Science. Oct. 30, 1992;258(5083):818-21.
Karlin, et al. Applications and statistics for multiple high-scoring segments in molecular sequences. Proc Natl Acad Sci USA. Jun. 15, 1993;90(12):5873-7.
Kendrew et al. (eds.), The Encyclopedia of Molecular Biology, published by Blackwell Science Ltd., 1994 (ISBN 0-632-02182-9).
Kenneth, R.H., in Monoclonal Antibodies: A New Dimension In Biological Analyses, Plenum Publishing Corp., New York, New York (1980).

(56) References Cited

OTHER PUBLICATIONS

Kim, et al. Strategies for silencing human disease using RNA interference. Nat Rev Genet. Mar. 2007;8(3):173-84.
Kim, et al., Synthetic dsRNA dicer substrates enhance RNAi potency and efficacy. Nature biotechnology. 2005; 23(2): 222-226.
Klein, et al. Comparative genomic hybridization, loss of heterozygosity, and DNA sequence analysis of single cells. Proc Natl Acad Sci USA. Apr. 13, 1999;96(8):4494-9.
Kohler, et al. Continuous cultures of fused cells secreting antibody of predefined specificity. Nature. Aug. 7, 1975;256(5517):495-7.
Kozbor, et al. The production of monoclonal antibodies from human lymphocytes. Immunol. Today. 1983; 4(3): 72-79.
Kraus, et al. Detection and isolation of novel protein-tyrosine kinase genes employing reduced stringency hybridization. Methods Enzymol. 1991;200:546-56.
Kurreck, J. Antisense technologies. Improvement through novel chemical modifications. Eur J Biochem. Apr. 2003;270(8):1628-44.
Kutyavin, et al. A novel endonuclease IV post-PCR genotyping system. Nucleic Acids Res. 2006;34(19):e128. Epub Sep. 29, 2006.
Lakowicz, J. (1983) Principles of fluorescence spectroscopy. Plenum Press, New York.
Lavery, et al. Antisense and RNAi: powerful tools in drug target discovery and validation. Curr Opin Drug Discov Devel. Jul. 2003;6(4):561-9.
Lerner. How to make a hybridoma. Yale J Biol Med. 54(5):387-402 (1981).
Lewin, B., Genes IX, published by Jones & Bartlett Publishing, 2007 (ISBN-13:9780763740634).
Lucentini. Gene Association Studies Typically Wrong. The Scientist, 18(24):20 (2004).
Maniatis, et al. Molecular Cloning: A Laboratory Manual, Cold Spring Harbor Laboratory Press, Cold Spring Harbor, N.Y., USA (1982).
Margulies, et al. Genome sequencing in microfabricated high-density picolitre reactors. Nature. Sep. 15, 2005;437(7057):376-80. Epub Jul. 31, 2005.
Marques, et al. A structural basis for discriminating between self and nonself double-stranded RNAs in mammalian cells. Nat Biotechnol. May 2006;24(5):559-65. Epub Apr. 30, 2006.
Martinez et al. Single-stranded antisense siRNAs guide target RNA cleavage in RNAi. Cell 110(5):563-574 (2002).
Mather, J.P. et al., Animal Cell Culture Methods (Methods in Cell Biology, vol. 57, Academic Press, 1st edition, 1998.
May et al., Endometrial alterations in endometriosis: a systematic review of putative biomarkers. Hum. Reprod. Update, 17(5); 637-53:2011.
Mcmanus, et al. Gene silencing in mammals by small interfering RNAs. Nat Rev Genet. Oct. 2002;3(10):737-47.
Mockler, et al. Applications of DNA tiling arrays for whole-genome analysis. Genomics. Jan. 2005;85(1):1-15.
National Center for Biotechnology Information. NCBI. Available at: https://www.ncbi.nlm.nih.gov/. Accessed on: Jun. 8, 2017.
Nielsen, et al. Sequence-selective recognition of DNA by strand displacement with a thymine-substituted polyamide. Science. 254: 1497-1500 (1991).
Nykanen, et al. ATP requirements and small interfering RNA structure in the RNA interference pathway. Cell. Nov. 2, 2001;107(3):309-21.
Office Action dated Apr. 7, 2017 for U.S. Appl. No. 14/538,404.
Perkel, J. SNP genotyping: six technologies that keyed a revolution. Nature Methods. 2008; 5:447-453.
Plasterk, et al. The silence of the genes. Curr Opin Genet Dev. Oct. 2000;10(5):562-7.
Probe Reports from the NIH Molecular Libraries Program [Internet], Bethesda (MD): National Center for Biotechnology Information (US); 2010. Available from: https://www.ncbi.nlm.nih.gov/books/NBK47352/.
Provost, et al. Ribonuclease activity and RNA binding of recombinant human Dicer. EMBO J. Nov. 1, 2002;21(21):5864-74.
Ragoussis, et al. Affymetrix GeneChip system: moving from research to the clinic. Expert Rev Mol Diagn. Mar. 2006;6(2):145-52.
Redon, et al. Global variation in copy number in the human genome. Nature. Nov. 23, 2006;444(7118):444-54.
Revised American society for reproductive medicine classification of endometriosis: 1996. Fertility and Sterility. 67: 1997; 817-21.
Reynold, et al. Rational siRNA design for RNA interference. Nat Biotechnol. Mar. 2004;22(3):326-30. Epub Feb. 1, 2004.
Robert A. Meyers (ed.), Molecular Biology and Biotechnology: a Comprehensive Desk Reference, published by VCH Publishers, Inc., 1995 (ISBN 1-56081-569-8).
Sambrook et al., Molecular Cloning: A Laboratory Manual (2 ed.), Cold Spring Harbor Laboratory Press, Cold Spring Harbor, N.Y., USA (1989).
Santa Cruz Human Genome Browser Gateway. 2017. Available at: http://genome.ucsc.edu/cgi-bin/hgGateway. Accessed on: Jun. 8, 2017.
Schwarz, et al. Asymmetry in the assembly of the RNAi enzyme complex. Cell. Oct. 17, 2003;115(2):199-208.
Seshan VE and Olshen A (2017). DNAcopy: DNA copy number data analysis. R package version 1.50.1. Available at: http://www.bioconductor.org/packages/release/bioc/html/DNAcopy.html.
Sharp. RNA interference-2001. Genes Dev 15(5):485-490 (2001).
Shi, Y. Mammalian RNAi for the masses. Trends Genet. Jan. 2003;19(1):9-12.
Shuey, et al. RNAi: gene-silencing in therapeutic intervention. Drug Discov Today. Oct. 15, 2002;7(20):1040-6.
Siolas, et al. Synthetic shRNAs as potent RNAi triggers. Nat Biotechnol. Feb. 2005;23(2):227-31. Epub Dec. 26, 2004.
Smith, et al. A high-density admixture map for disease gene discovery in african americans. Am J Hum Genet. May 2004;74(5):1001-13. Epub Apr. 14, 2004.
Snijders, et al. Assembly of microarrays for genome-wide measurement of DNA copy number Nat Genet. Nov. 2001;29(3):263-4.
Snijders, et al. BAC microarray-based comparative genomic hybridization. Methods Mol Biol. 2004;256:39-56.
Stephens, et al. Antisense oligonucleotide therapy in cancer. Curr Opin Mol Ther. Apr. 2003;5(2):118-22.
String. Search single protein by name/identifier. String consortium 2017. Available at:https://string-db.org/.
Suryawanshi, S., et al., "Plasma microRNAs as novel biomarkers for endometriosis and endometriosis-associated ovarian cancer", Clin Cancer Res., 19(5), (Mar. 1, 2013), 1213-24.
Tabara, et al. The dsRNA binding protein RDE-4 interacts with RDE-1, DCR-1, and a DExH-box helicase to direct RNAi in C. elegans. Cell. Jun. 28, 2002;109(7):861-71.
The Merck Manual of Diagnosis and Therapy, 18th Edition, published by Merck Research Laboratories, 2006 (ISBN 0-911910-18-2).
Thompson. Applications of antisense and siRNAs during preclinical drug development. Drug Discov Today. Sep. 1, 2002;7(17):912-7.
Thorpe, et al. Improved antitumor effects of immunotoxins prepared with deglycosylated ricin A-chain and hindered disulfide linkages. Cancer Res. Nov. 15, 1988;48(22):6396-403.
U.S. Appl. No. 14/538,404 Notice of Allowance dated Aug. 23, 2018.
U.S. Appl. No. 14/538,404 Notice of Allowance dated May 18, 2018.
U.S. Appl. No. 14/538,404 Office Action dated Dec. 29, 2017.
Vickers, et al. Efficient reduction of target RNAs by small interfering RNA and RNase H-dependent antisense agents. A comparative analysis. J Biol Chem. Feb. 28, 2003;278(9):7108-18. Epub Dec. 23, 2002.
Wang, et al. Antisense anticancer oligonucleotide therapeutics. Curr Cancer Drug Targets. Nov. 2001;1(3):177-96.
Xia, et al. siRNA-mediated gene silencing in vitro and in vivo. Nat Biotechnol. Oct. 2002;20(10):1006-10. Epub Sep. 16, 2002.
Xiao, et al., Identification and optimization of small-molecule agonists of the human relaxin hormone receptor RXFP1. Nat Commun. 2013;4:1953. doi:10.1038/ncomms2953.

(56) References Cited

OTHER PUBLICATIONS

Zhao et al. (eds), Bacterial Artificial Chromosomes: Methods Protocols Methods in Molecular Biology, Humana Press, 2004.

* cited by examiner

| Chromosome | Original CNV Start | Original CNV Stop | Original CNV Size | CNV Type | Endo Cases ID | RefSeq Gene Symbol | SEQ ID |
|---|---|---|---|---|---|---|---|
| 1 | 92013987 | 92020793 | 6806 | loss | 2883 | TGFBR3 | 1 |
| 1 | 92013987 | 92020793 | 6806 | loss | 2922 | TGFBR3 | 1 |
| 1 | 92013987 | 92020793 | 6806 | loss | 2971 | TGFBR3 | 1 |
| 23 | 149901706 | 149904265 | 2559 | gain | 2898 | HMGB3 | 2 |
| 23 | 149901706 | 149904265 | 2559 | gain | 2899 | HMGB3 | 2 |
| 23 | 149901706 | 149904265 | 2559 | gain | 2907 | HMGB3 | 2 |
| 23 | 149901706 | 149904265 | 2559 | gain | 2909 | HMGB3 | 2 |
| 23 | 149902703 | 149904265 | 1563 | gain | 2883 | HMGB3 | 3 |
| 23 | 149901706 | 149904265 | 2559 | gain | 2896 | HMGB3 | 2 |
| 23 | 149901706 | 149904265 | 2559 | gain | 2899 | HMGB3 | 2 |
| 23 | 149901706 | 149904265 | 2559 | gain | 2907 | HMGB3 | 2 |
| 23 | 149901706 | 149904265 | 2559 | gain | 2909 | HMGB3 | 2 |
| 6 | 966106680 | 966625609 | 14929 | gain | 2905 | FUT9 | 4 |
| 6 | 966106680 | 966639872 | 19192 | gain | 2910 | FUT9 | 5 |
| 6 | 966106680 | 966625609 | 14929 | gain | 2916 | FUT9 | 4 |
| 6 | 966106680 | 966625609 | 14929 | gain | 2924 | FUT9 | 4 |
| 7 | 31844434 | 31851158 | 6724 | gain | 2883 | PDE1C | 6 |
| 7 | 31844434 | 31851158 | 6724 | gain | 2973 | PDE1C | 6 |
| 7 | 31844434 | 31851158 | 6724 | gain | 2978 | PDE1C | 6 |
| 10 | 596180 47 | 596304 93 | 12446 | gain | 2955 | IPMK | 7 |
| 10 | 596180 47 | 596304 93 | 12446 | gain | 2977 | IPMK | 7 |
| 10 | 596180 47 | 596304 93 | 12446 | gain | 2978 | IPMK | 7 |
| 2 | 23285559 | 231298735 | 12676 | gain | 2924 | GIGYF2 | 8 |
| 2 | 233285559 | 233300736 | 15177 | gain | 2950 | GIGYF2 | 9 |
| 2 | 233285559 | 233311246 | 25687 | gain | 2899 | GIGYF2 | 10 |
| 6 | 1385216944 | 1385228800 | 5856 | gain | 2968 |   | 11 |
| 6 | 1385216944 | 1385220155 | 3211 | gain | 2971 |   | 12 |
| 6 | 1385216944 | 1385222680 | 5856 | gain | 2978 |   | 11 |
| 11 | 44056561 | 44062111 | 5850 | loss | 2883 | ACCS | 13 |
| 11 | 44056561 | 44058123 | 1562 | loss | 2948 | ACCS | 14 |
| 11 | 44056561 | 44058123 | 1562 | loss | 2950 | ACCS | 14 |
| 7 | 153645525 | 153647352 | 1827 | loss | 2931 | DPP6 | 15 |
| 7 | 153645525 | 153647352 | 1827 | loss | 2976 | DPP6 | 15 |
| 7 | 153645525 | 153647352 | 1827 | loss | 2977 | DPP6 | 15 |
| 6 | 120674750 | 120685561 | 11191 | loss | 2882 |   | 16 |

FIG. 1

| Chromosome | Original_CNV_Start | Original_CNV_Stop | Original_CNV_Size | CNV_Type | Endo_Case_ID | RefSeq_Gene_Symbol | SEQ_ID |
|---|---|---|---|---|---|---|---|
| 6 | 120674750 | 120685941 | 11191 | loss | 2922 | | 16 |
| 6 | 120678750 | 120680729 | 5979 | loss | 2951 | | 17 |
| 16 | 31356033 | 31434641 | 78603 | gain | 2925 | TGFB1I1,SLC5A2,ZNF843,C16orf58,ARMC5 | 18 |
| 8 | 142060703 | 142065735 | 5032 | loss | 2954 | PTK2 | 19 |
| 4 | 128995909 | 129451283 | 455374 | gain | 3001 | LARP1B,PGRMC2 | 20 |
| 19 | 41532062 | 41538649 | 6587 | gain | 2885 | ZFP14 | 21 |
| 19 | 41532062 | 41538649 | 6587 | gain | 2925 | ZFP14 | 21 |
| 19 | 41532062 | 41538649 | 6587 | gain | 2969 | ZFP14 | 21 |
| 19 | 41532062 | 41538649 | 6587 | gain | 2977 | ZFP14 | 21 |
| 19 | 41532062 | 41538649 | 6587 | gain | 3000 | ZFP14 | 21 |
| 1 | 65627570 | 65727987 | 100417 | gain | 2942 | DNAJC6,LEPR,LEPROT | 22 |
| 3 | 196906225 | 197063388 | 75163 | gain | 2957 | MUC4 | 23 |
| 23 | 148575584 | 148653616 | 78032 | gain | 2901 | MAGEA11 | 24 |
| 2 | 242109898 | 242169452 | 59554 | gain | 2959 | BOK,BOK-AS1 | 25 |
| 14 | 80613390 | 80649676 | 36486 | gain | 2981 | TSHR | 26 |
| 23 | 64731495 | 64818228 | 86733 | gain | 2932 | MSN | 27 |
| 2 | 337738800 | 339034646 | 1295836 | loss | 2913 | MYADML | 28 |
| 10 | 104414630 | 104810431 | 395751 | gain | 2921 | CNNM2,C10orf32,ARL3,CYP17A1,WBP1L,SFXN2,C10orf26-AS3MT,AS3MT | 29 |
| 4 | 159674853 | 159663362 | 8709 | loss | 2934 | RXFP1 | 30 |
| 7 | 30668143 | 30681882 | 13739 | loss | 2968 | CRHR2 | 31 |
| 19 | 53252457 | 53257305 | 4848 | loss | 2985 | PLA2G4C | 32 |
| 2 | 247981930 | 248806680 | 8490 | gain | 2971 | NCOA1 | 33 |
| 7 | 139722619 | 139853019 | 130400 | gain | 2946 | RAB19,SLC37A3,MKRN1 | 34 |
| 9 | 16567785 | 16576265 | 8430 | gain | 2968 | BNC2 | 35 |
| 1 | 16713074 | 17148592 | 435518 | gain | 2887 | NBPF1 | 36 |
| 1 | 16713074 | 17148592 | 435518 | gain | 2913 | NBPF1 | 36 |
| 1 | 16713074 | 16926444 | 213370 | gain | 2920 | NBPF1 | 37 |
| 1 | 16713074 | 17127039 | 413965 | gain | 2925 | NBPF1 | 38 |
| 1 | 16713074 | 16926444 | 213370 | gain | 2930 | NBPF1 | 37 |
| 1 | 16713074 | 17148592 | 435518 | gain | 2933 | NBPF1 | 36 |
| 1 | 16713074 | 16926444 | 213370 | gain | 2936 | NBPF1 | 37 |
| 1 | 16713074 | 17148592 | 435518 | gain | 2941 | NBPF1 | 36 |
| 1 | 16713074 | 17148592 | 435518 | gain | 2943 | NBPF1 | 36 |
| 1 | 16713074 | 17148592 | 435518 | gain | 2968 | NBPF1 | 36 |

FIG. 1 (CONTINUED)

| Chromosome | Original CNV Start | Original CNV Stop | Original CNV Size | CNV Type | Endo Case ID | RefSeq Gene Symbol | SEQ ID |
|---|---|---|---|---|---|---|---|
| 1 | 16713074 | 16926444 | 213370 | gain | 2969 | NBPF1 | 37 |
| 1 | 16713074 | 171270039 | 4139365 | gain | 2978 | NBPF1 | 38 |
| 1 | 16713074 | 171485592 | 435518 | gain | 2981 | NBPF1 | 36 |
| 1 | 16713074 | 171485592 | 435518 | gain | 2991 | NBPF1 | 36 |
| 1 | 16713074 | 171270039 | 413965 | gain | 2994 | NBPF1 | 38 |
| 1 | 16713074 | 16926444 | 213370 | gain | 2996 | NBPF1 | 37 |
| 1 | 16713074 | 171485592 | 435518 | gain | 2998 | NBPF1 | 36 |
| 1 | 16704522 | 16963812 | 259290 | loss | 3011 | NBPF1 | 39 |
| 1 | 16713074 | 171485592 | 435518 | gain | 3002 | NBPF1 | 36 |
| 1 | 16713074 | 171270039 | 413965 | gain | 3003 | NBPF1 | 38 |
| 15 | 86941339 | 86944414 | 3075 | gain | 2901 | | 40 |
| 15 | 86943691 | 86944414 | 723 | gain | 2913 | | 41 |
| 15 | 86941339 | 86944968 | 3629 | gain | 2923 | | 42 |
| 15 | 86941339 | 86944414 | 3075 | gain | 2926 | | 40 |
| 15 | 86941339 | 86944414 | 3075 | gain | 2937 | | 40 |
| 15 | 86943691 | 86944414 | 723 | gain | 2946 | | 41 |
| 15 | 86941339 | 86944414 | 3075 | gain | 2975 | | 40 |
| 15 | 86941339 | 86944414 | 3075 | gain | 2976 | | 40 |
| 15 | 86941339 | 86944414 | 3075 | gain | 2982 | | 40 |
| 15 | 86941339 | 86944968 | 3629 | gain | 2995 | | 42 |
| 15 | 86941339 | 86944968 | 3629 | gain | 2996 | | 42 |
| 15 | 86941339 | 86944414 | 3075 | gain | 3002 | | 40 |
| 15 | 86941339 | 86944414 | 3075 | gain | 2901 | | 40 |
| 15 | 86941339 | 86944968 | 3629 | gain | 2923 | | 42 |
| 15 | 86941339 | 86944414 | 3075 | gain | 2926 | | 40 |
| 15 | 86941339 | 86944414 | 3075 | gain | 2937 | | 40 |
| 15 | 86941339 | 86944414 | 3075 | gain | 2975 | | 40 |
| 15 | 86941339 | 86944414 | 3075 | gain | 2976 | | 40 |
| 15 | 86941339 | 86944414 | 3075 | gain | 2982 | | 40 |
| 15 | 86941339 | 86944963 | 3629 | gain | 2995 | | 42 |
| 15 | 86941339 | 86944968 | 3629 | gain | 2996 | | 42 |
| 15 | 86941339 | 86944414 | 3075 | gain | 3002 | | 40 |
| 2 | 191869063 | 191874236 | 5173 | loss | 2883 | MYO1B | 43 |
| 2 | 191869063 | 191874236 | 5173 | loss | 2899 | MYO1B | 43 |
| 2 | 191869063 | 191874236 | 5173 | loss | 2903 | MYO1B | 43 |

FIG. 1 (CONTINUED)

| Chromosome | Original CNV Start | Original CNV Stop | Original CNV Size | CNV Type | Endo_Case_ID | RefSeq_Gene_Symbol | SEQ_ID |
|---|---|---|---|---|---|---|---|
| 2 | 1918690063 | 1918742236 | 5173 | loss | 2915 | MYO1B | 43 |
| 2 | 1918690063 | 1918742236 | 5173 | loss | 2922 | MYO1B | 43 |
| 2 | 1918690063 | 1918742236 | 5173 | loss | 2926 | MYO1B | 43 |
| 2 | 1918690063 | 1918742236 | 5173 | loss | 2938 | MYO1B | 43 |
| 2 | 1918690063 | 1918742236 | 5173 | loss | 2945 | MYO1B | 43 |
| 2 | 1918690063 | 1918742236 | 5173 | loss | 2953 | MYO1B | 43 |
| 2 | 1918690063 | 1918742236 | 5173 | loss | 2954 | MYO1B | 43 |
| 2 | 1918690063 | 1918742236 | 5173 | loss | 2962 | MYO1B | 43 |
| 2 | 1918677698 | 1918742236 | 6538 | loss | 2965 | MYO1B | 44 |
| 2 | 1918690063 | 1918742236 | 5173 | loss | 2966 | MYO1B | 43 |
| 2 | 1918690063 | 1918742236 | 5173 | loss | 2973 | MYO1B | 43 |
| 2 | 1918690063 | 1918742236 | 5173 | loss | 2974 | MYO1B | 43 |
| 2 | 1918690063 | 1918759965 | 6902 | loss | 2978 | MYO1B | 45 |
| 2 | 1918690063 | 1918742236 | 5173 | loss | 2979 | MYO1B | 43 |
| 2 | 1918690063 | 1918742236 | 5173 | loss | 2986 | MYO1B | 43 |
| 2 | 1918690063 | 1918742236 | 5173 | loss | 2999 | MYO1B | 43 |
| 2 | 1918690063 | 1918742236 | 5173 | loss | 3003 | MYO1B | 43 |
| 2 | 1918690063 | 1918742236 | 5173 | loss | 2883 | MYO1B | 43 |
| 2 | 1918690063 | 1918742236 | 5173 | loss | 2899 | MYO1B | 43 |
| 2 | 1918690063 | 1918742236 | 5173 | loss | 2903 | MYO1B | 43 |
| 2 | 1918690063 | 1918742236 | 5173 | loss | 2915 | MYO1B | 43 |
| 2 | 1918690063 | 1918742236 | 5173 | loss | 2922 | MYO1B | 43 |
| 2 | 1918690063 | 1918742236 | 5173 | loss | 2926 | MYO1B | 43 |
| 2 | 1918690063 | 1918742236 | 5173 | loss | 2938 | MYO1B | 43 |
| 2 | 1918690063 | 1918742236 | 5173 | loss | 2945 | MYO1B | 43 |
| 2 | 1918690063 | 1918742236 | 5173 | loss | 2953 | MYO1B | 43 |
| 2 | 1918690063 | 1918742236 | 5173 | loss | 2954 | MYO1B | 43 |
| 2 | 1918690063 | 1918742236 | 5173 | loss | 2962 | MYO1B | 43 |
| 2 | 1918677698 | 1918742236 | 6538 | loss | 2965 | MYO1B | 44 |
| 2 | 1918690063 | 1918742236 | 5173 | loss | 2966 | MYO1B | 43 |
| 2 | 1918690063 | 1918742236 | 5173 | loss | 2973 | MYO1B | 43 |
| 2 | 1918690063 | 1918742236 | 5173 | loss | 2974 | MYO1B | 43 |
| 2 | 1918690063 | 1918742236 | 5173 | loss | 2978 | MYO1B | 43 |
| 2 | 1918690063 | 1918759965 | 6902 | loss | 2979 | MYO1B | 45 |
| 2 | 1918690063 | 1918742236 | 5173 | loss | 2986 | MYO1B | 43 |

FIG. 1 (CONTINUED)

| Chromosome | Original_CNV_Start | Original_CNV_Stop | Original_CNV_Size | CNV_Type | Endo_Case_ID | RefSeq_Gene_Symbol | SEQ_ID |
|---|---|---|---|---|---|---|---|
| 2 | 191869063 | 191874236 | 5173 | loss | 2999 | MYO1B | 43 |
| 2 | 191869063 | 191874236 | 5173 | loss | 3003 | MYO1B | 43 |
| 6 | 47731384 | 47734315 | 2931 | loss | 2905 | GPR111 | 46 |
| 6 | 47731384 | 47734315 | 2931 | loss | 2909 | GPR111 | 46 |
| 6 | 47731384 | 47734315 | 2931 | loss | 2915 | GPR111 | 46 |
| 6 | 47731384 | 47734315 | 2931 | loss | 2917 | GPR111 | 46 |
| 6 | 47731384 | 47734315 | 2931 | loss | 2919 | GPR111 | 46 |
| 6 | 47731384 | 47734315 | 2931 | loss | 2924 | GPR111 | 46 |
| 6 | 47731384 | 47734315 | 2931 | loss | 2926 | GPR111 | 46 |
| 6 | 47731384 | 47734315 | 2931 | loss | 2930 | GPR111 | 46 |
| 6 | 47731384 | 47734315 | 2931 | loss | 2933 | GPR111 | 46 |
| 6 | 47731384 | 47734315 | 2931 | loss | 2946 | GPR111 | 46 |
| 6 | 47731384 | 47734315 | 2931 | loss | 2951 | GPR111 | 46 |
| 6 | 47731384 | 47734315 | 2931 | loss | 2961 | GPR111 | 46 |
| 6 | 47731384 | 47734315 | 2931 | loss | 2976 | GPR111 | 46 |
| 6 | 47731384 | 47734315 | 2931 | loss | 2983 | GPR111 | 46 |
| 6 | 47731384 | 47734315 | 2931 | loss | 2985 | GPR111 | 46 |
| 6 | 70290311 | 70295413 | 5102 | gain | 2910 | | 47 |
| 6 | 70290311 | 70295413 | 5102 | gain | 2914 | | 47 |
| 6 | 70290311 | 70295413 | 5102 | gain | 2919 | | 47 |
| 6 | 70290311 | 70295413 | 5102 | gain | 2921 | | 47 |
| 6 | 70290311 | 70295413 | 5102 | gain | 2923 | | 47 |
| 6 | 70290311 | 70295413 | 5102 | gain | 2924 | | 47 |
| 6 | 70290311 | 70295413 | 5102 | gain | 2937 | | 47 |
| 6 | 70290311 | 70295413 | 5102 | gain | 2943 | | 47 |
| 6 | 70290311 | 70295413 | 5102 | gain | 2944 | | 47 |
| 6 | 70290311 | 70295413 | 5102 | gain | 2948 | | 47 |
| 6 | 70290311 | 70295413 | 5102 | gain | 2959 | | 47 |
| 6 | 70290311 | 70295413 | 5102 | gain | 2979 | | 47 |
| 6 | 70290311 | 70295413 | 5102 | gain | 2981 | | 47 |
| 6 | 70290311 | 70295413 | 5102 | gain | 2982 | | 47 |
| 6 | 70290311 | 70295413 | 5102 | gain | 2983 | | 47 |
| 6 | 70290311 | 70295413 | 5102 | gain | 2985 | | 47 |

FIG. 1 (CONTINUED)

| SRN | Chromosome | CNV_Subregion_Start | CNV_Subregion_Stop | CNV_Subregion_Size | CNV_Type | Endo_Case_ID(s) | RefSeq_Gene_Symbol | Exon_overlap | NVE_cases | End_cases | FET | OR | Category |
|---|---|---|---|---|---|---|---|---|---|---|---|---|---|
| 1 | 1 | 92013987 | 92020793 | 6806 | loss | 2883 | TGFBR3 | N | 0 | 3 | 6.80E-05 | 72.19 | stats_biology |
| 2 | 1 | 92013987 | 92020793 | 6806 | loss | 2923 | TGFBR3 | N | 0 | 3 | 6.80E-05 | 72.19 | stats_biology |
| 3 | 1 | 92013987 | 92020793 | 6806 | loss | 2971 | TGFBR3 | N | 0 | 3 | 6.80E-05 | 72.19 | stats_biology |
| 4 | 23 | 149901706 | 149902701 | 995 | gain | 2898 | HMGB3 | Y | 0 | 4 | 6.32E-05 | 93.78 | stats_biology |
| 5 | 23 | 149901706 | 149902701 | 995 | gain | 2899 | HMGB3 | Y | 0 | 4 | 6.32E-05 | 93.78 | stats_biology |
| 6 | 23 | 149901706 | 149902701 | 995 | gain | 2907 | HMGB3 | Y | 0 | 4 | 6.32E-05 | 93.78 | stats_biology |
| 7 | 23 | 149901706 | 149902701 | 995 | gain | 2909 | HMGB3 | Y | 0 | 4 | 6.32E-05 | 93.78 | stats_biology |
| 8 | 23 | 149902702 | 149904265 | 1563 | gain | 2883 | HMGB3 | N | 2 | 5 | 1.00E-04 | 26.39 | biology |
| 9 | 23 | 149902702 | 149904265 | 1563 | gain | 2898 | HMGB3 | N | 2 | 5 | 1.00E-04 | 26.39 | biology |
| 10 | 23 | 149902702 | 149904265 | 1563 | gain | 2899 | HMGB3 | N | 2 | 5 | 1.00E-04 | 26.39 | biology |
| 11 | 23 | 149902702 | 149904265 | 1563 | gain | 2907 | HMGB3 | N | 2 | 5 | 1.00E-04 | 26.39 | biology |
| 12 | 23 | 149902702 | 149904265 | 1563 | gain | 2909 | HMGB3 | N | 2 | 5 | 1.00E-04 | 26.39 | biology |
| 13 | 6 | 96610680 | 96625609 | 14929 | gain | 2905 | FUT9 | N | 0 | 4 | 6.32E-05 | 93.78 | stats_biology |
| 14 | 6 | 96610680 | 96625609 | 14929 | gain | 2910 | FUT9 | N | 0 | 4 | 6.32E-05 | 93.78 | stats_biology |
| 15 | 6 | 96610680 | 96625609 | 14929 | gain | 2916 | FUT9 | N | 0 | 4 | 6.32E-05 | 93.78 | stats_biology |
| 16 | 6 | 96610680 | 96625609 | 14929 | gain | 2924 | FUT9 | N | 0 | 4 | 6.32E-05 | 93.78 | stats_biology |
| 17 | 7 | 31844434 | 31851158 | 6724 | gain | 2883 | PDE1C | N | 0 | 3 | 6.80E-05 | 72.19 | stats_biology |
| 18 | 7 | 31844434 | 31851158 | 6724 | gain | 2973 | PDE1C | N | 0 | 3 | 6.80E-05 | 72.19 | stats_biology |
| 19 | 7 | 31844434 | 31851158 | 6724 | gain | 2978 | PDE1C | N | 0 | 3 | 6.80E-05 | 72.19 | stats |

FIG. 2

| SRN | Chromosome | CNV_Subregion_Start | CNV_Subregion_Stop | CNV_Subregion_Size | CNV_Type | Endo_Case_ID(s) | RefSeq_Gene_Symbol | Exon_overlap | NVE_cases | End_cases | FET | OR | Category |
|---|---|---|---|---|---|---|---|---|---|---|---|---|---|
| 20 | 10 | 59620764 | 59630493 | 9729 | gain | 2955 | IPMK | Y | 0 | 3 | 6.80E-05 | 72.19 | stats_biology |
| 21 | 10 | 59620764 | 59630493 | 9729 | gain | 2977 | IPMK | Y | 0 | 3 | 6.80E-05 | 72.19 | stats_biology |
| 22 | 10 | 59620764 | 59630493 | 9729 | gain | 2978 | IPMK | Y | 0 | 3 | 6.80E-05 | 72.19 | stats_biology |
| 23 | 2 | 233285559 | 233298235 | 12676 | gain | 2924 | GIGYF2 | N | 0 | 3 | 6.80E-05 | 72.19 | stats_biology |
| 24 | 2 | 233285559 | 233298235 | 12676 | gain | 2950 | GIGYF2 | N | 0 | 3 | 6.80E-05 | 72.19 | stats_biology |
| 25 | 2 | 233285559 | 233298235 | 12676 | gain | 2999 | GIGYF2 | N | 0 | 3 | 6.80E-05 | 72.19 | stats_biology |
| 26 | 6 | 138516944 | 138520155 | 3211 | gain | 2968 |  | N | 0 | 3 | 6.80E-05 | 72.19 | stats_biology |
| 27 | 6 | 138516944 | 138520155 | 3211 | gain | 2971 |  | N | 0 | 3 | 6.80E-05 | 72.19 | stats_biology |
| 28 | 6 | 138516944 | 138520155 | 3211 | gain | 2978 |  | N | 0 | 3 | 6.80E-05 | 72.19 | stats_biology |
| 29 | 11 | 44056561 | 44058123 | 1562 | loss | 2883 | ACCS | Y | 0 | 3 | 6.80E-05 | 72.19 | stats |
| 30 | 11 | 44056561 | 44058123 | 1562 | loss | 2948 | ACCS | Y | 0 | 3 | 6.80E-05 | 72.19 | stats |
| 31 | 11 | 44056561 | 44058123 | 1562 | loss | 2950 | ACCS | Y | 0 | 3 | 6.80E-05 | 72.19 | stats |
| 32 | 7 | 153645525 | 153647352 | 1827 | loss | 2923 | DPP6 | N | 0 | 3 | 6.80E-05 | 72.19 | stats |
| 33 | 7 | 153645525 | 153647352 | 1827 | loss | 2976 | DPP6 | N | 0 | 3 | 6.80E-05 | 72.19 | stats |
| 34 | 7 | 153645525 | 153647352 | 1827 | loss | 2977 | DPP6 | N | 0 | 3 | 6.80E-05 | 72.19 | stats |
| 35 | 6 | 120674750 | 120680729 | 5979 | loss | 2882 |  | N | 0 | 3 | 6.80E-05 | 72.19 | stats |
| 36 | 6 | 120674750 | 120680729 | 5979 | loss | 2922 |  | N | 0 | 3 | 6.80E-05 | 72.19 | stats |
| 37 | 6 | 120674750 | 120680729 | 5979 | loss | 2951 |  | N | 0 | 3 | 6.80E-05 | 72.19 | stats |
| 38 | 16 | 31356038 | 31434641 | 78603 | gain | 2975 | ARMC5, C16orf58, SLC5A2, | Y | 0 | 1 | 8.40E-03 | 30.32 | biology |

FIG. 2 (CONTINUED)

| SRN | Chromo some | CNV_ Subregion_ Start | CNV_ Subregion_ Stop | CNV_Sub region_Si ze | CNV_ Type | Endo_ Case_ ID(s) | RefSeq_ Gene_ Symbol | Exon_ over- lap | NVE_ cases | End_ cases | FET | OR | Category |
|---|---|---|---|---|---|---|---|---|---|---|---|---|---|
| 39 | 8 | 142060703 | 142065735 | 5032 | loss | 2954 | TGFB11 1,ZNF 843 PTK2 | Y | 0 | 1 | 8.40E-03 | 30.32 | biology |
| 40 | 4 | 129189476 | 129451283 | 261807 | gain | 3001 | LARP1B, PGR MC2 | Y | 0 | 1 | 8.40E-03 | 30.32 | biology |
| 41 | 19 | 41532062 | 41533404 | 1342 | gain | 2885 | ZFP14 | N | 1 | 5 | 3.08E-05 | 52.84 | stats |
| 42 | 19 | 41532062 | 41533404 | 1342 | gain | 2925 | ZFP14 | N | 1 | 5 | 3.08E-05 | 52.84 | stats |
| 43 | 19 | 41532062 | 41533404 | 1342 | gain | 2969 | ZFP14 | N | 1 | 5 | 3.08E-05 | 52.84 | stats |
| 44 | 19 | 41532062 | 41533404 | 1342 | gain | 2977 | ZFP14 | N | 1 | 5 | 3.08E-05 | 52.84 | stats |
| 45 | 19 | 41532062 | 41533404 | 1342 | gain | 3000 | ZFP14 | N | 1 | 5 | 3.08E-05 | 52.84 | stats |
| 46 | 1 | 65627570 | 65696043 | 68473 | gain | 2942 | DNAJC6 ,LEPR,L EPROT | Y | 1 | 1 | 1.73E-01 | 10.14 | biology |
| 47 | 3 | 197001562 | 197065388 | 63826 | gain | 2997 | MUC4 | Y | 1 | 1 | 1.73E-01 | 10.14 | biology |
| 48 | 23 | 148575584 | 148608166 | 32582 | gain | 2901 | MAGEA1 1 | Y | 1 | 1 | 1.73E-01 | 10.14 | biology |
| 49 | 2 | 242109998 | 242153935 | 43937 | gain | 2959 | BOK,BO K-AS1 | Y | 0 | 1 | 8.40E-03 | 30.32 | biology |
| 50 | 14 | 80613390 | 80649876 | 36486 | gain | 2981 | TSHR | Y | 0 | 1 | 8.40E-03 | 30.32 | biology |
| 51 | 23 | 64731495 | 64811828 | 80333 | gain | 2932 | MSN | Y | 0 | 1 | 8.40E-03 | 30.32 | biology |
| 52 | 2 | 33773800 | 33903436 | 129636 | loss | 2913 | MYADM L | Y | 0 | 1 | 8.40E-03 | 30.32 | biology |

FIG. 2 (CONTINUED)

| SRN | Chromo some | CNV_ Subregion_ Start | CNV_ Subregion_ Stop | CNV_Sub region_Si ze | CNV_ Type | Endo_ Case_ ID(s) | RefSeq_ Gene_ Symbol | Exon_ over- lap | NVE_ cases | End_ cases | FET | OR | Category |
|---|---|---|---|---|---|---|---|---|---|---|---|---|---|
| 53 | 10 | 104571485 | 104810431 | 238946 | gain | 2921 | AS3MT, C10orf3 2,C10orf 32- AS3MT, CNN M2,CYP 17A1 | Y | 0 | 1 | 8.40E-03 | 30.32 | biology |
| 54 | 4 | 159674653 | 159683362 | 8709 | loss | 2934 | RXFP1 | N | 0 | 1 | 0.00839 913 | 30.32 | biology |
| 55 | 7 | 30668143 | 30681882 | 13739 | loss | 2968 | CRHR2 | Y | 0 | 1 | 0.00839 913 | 30.32 | biology |
| 56 | 19 | 53252457 | 53257305 | 4848 | loss | 2985 | PLA2G4 C | Y | 0 | 1 | 0.00839 913 | 30.32 | biology |
| 57 | 2 | 24798190 | 24806680 | 8490 | gain | 2971 | NCOA1 | Y | 0 | 1 | 0.00839 913 | 30.32 | biology |
| 58 | 7 | 139757225 | 139828667 | 71442 | gain | 2946 | MKRN1, RAB19 | Y | 0 | 1 | 0.00839 913 | 30.32 | biology |
| 59 | 9 | 16567785 | 16576265 | 8480 | gain | 2968 | BNC2 | Y | 0 | 1 | 0.00839 913 | 30.32 | biology |
| 60 | 1 | 16713074 | 16799710 | 86636 | gain | 2887 | NBPF1 | Y | 42 | 20 | 8.70E-08 | 5.73 | stats_ biology |
| 61 | 1 | 16713074 | 16799710 | 86636 | gain | 2913 | NBPF1 | Y | 42 | 20 | 8.70E-08 | 5.73 | stats_ biology |
| 62 | 1 | 16713074 | 16799710 | 86636 | gain | 2920 | NBPF1 | Y | 42 | 20 | 8.70E-08 | 5.73 | stats_ biology |
| 63 | 1 | 16713074 | 16799710 | 86636 | gain | 2925 | NBPF1 | Y | 42 | 20 | 8.70E-08 | 5.73 | stats_ biology |
| 64 | 1 | 16713074 | 16799710 | 86636 | gain | 2930 | NBPF1 | Y | 42 | 20 | 8.70E-08 | 5.73 | stats_ biology |
| 65 | 1 | 16713074 | 16799710 | 86636 | gain | 2933 | NBPF1 | Y | 42 | 20 | 8.70E-08 | 5.73 | stats_ biology |
| 66 | 1 | 16713074 | 16799710 | 86636 | gain | 2936 | NBPF1 | Y | 42 | 20 | 8.70E-08 | 5.73 | stats_ |

FIG. 2 (CONTINUED)

| SRN | Chromosome | CNV_Subregion_Start | CNV_Subregion_Stop | CNV_Sub region_Size | CNV_Type | Endo_Case_ID(s) | RefSeq_Gene_Symbol | Exon_overlap | NVE_cases | Endo_cases | FET | OR | Category |
|---|---|---|---|---|---|---|---|---|---|---|---|---|---|
| 67 | 1 | 16713074 | 16799710 | 86636 | gain | 2941 | NBPF1 | Y | 42 | 20 | 8.70E-08 | 5.73 | stats_biology |
| 68 | 1 | 16713074 | 16799710 | 86636 | gain | 2943 | NBPF1 | Y | 42 | 20 | 8.70E-08 | 5.73 | stats_biology |
| 69 | 1 | 16713074 | 16799710 | 86636 | gain | 2968 | NBPF1 | Y | 42 | 20 | 8.70E-08 | 5.73 | stats_biology |
| 70 | 1 | 16713074 | 16799710 | 86636 | gain | 2969 | NBPF1 | Y | 42 | 20 | 8.70E-08 | 5.73 | stats_biology |
| 71 | 1 | 16713074 | 16799710 | 86636 | gain | 2978 | NBPF1 | Y | 42 | 20 | 8.70E-08 | 5.73 | stats_biology |
| 72 | 1 | 16713074 | 16799710 | 86636 | gain | 2981 | NBPF1 | Y | 42 | 20 | 8.70E-08 | 5.73 | stats_biology |
| 73 | 1 | 16713074 | 16799710 | 86636 | gain | 2991 | NBPF1 | Y | 42 | 20 | 8.70E-08 | 5.73 | stats_biology |
| 74 | 1 | 16713074 | 16799710 | 86636 | gain | 2994 | NBPF1 | Y | 42 | 20 | 8.70E-08 | 5.73 | stats_biology |
| 75 | 1 | 16713074 | 16799710 | 86636 | gain | 2996 | NBPF1 | Y | 42 | 20 | 8.70E-08 | 5.73 | stats_biology |
| 76 | 1 | 16713074 | 16799710 | 86636 | gain | 2998 | NBPF1 | Y | 42 | 20 | 8.70E-08 | 5.73 | stats_biology |
| 77 | 1 | 16713074 | 16799710 | 86636 | gain | 3001 | NBPF1 | Y | 42 | 20 | 8.70E-08 | 5.73 | stats_biology |
| 78 | 1 | 16713074 | 16799710 | 86636 | gain | 3002 | NBPF1 | Y | 42 | 20 | 8.70E-08 | 5.73 | stats_biology |
| 79 | 1 | 16713074 | 16799710 | 86636 | gain | 3003 | NBPF1 | Y | 42 | 20 | 8.70E-08 | 5.73 | stats_biology |
| 80 | 15 | 86943691 | 86944414 | 723 | gain | 2901 |  | N | 20 | 12 | 7.73E-06 | 6.72 | stats_biology |
| 81 | 15 | 86943691 | 86944414 | 723 | gain | 2913 |  | N | 20 | 12 | 7.73E-06 | 6.72 | stats_biology |
| 82 | 15 | 86943691 | 86944414 | 723 | gain | 2923 |  | N | 20 | 12 | 7.73E-06 | 6.72 | stats_biology |

FIG. 2 (CONTINUED)

| SRN | Chromo some | CNV_ Subregion_ Start | CNV_ Subregion_ Stop | CNV_Sub region_Si ze | CNV_ Type | Endo_ Case_ ID(s) | RefSeq_ Gene_ Symbol | Exon_ over- lap | NVE_ cases | End_ cases | FET | OR | Category |
|---|---|---|---|---|---|---|---|---|---|---|---|---|---|
| 83 | 15 | 86943691 | 86944414 | 723 | gain | 2926 | | N | 20 | 12 | 7.73E-06 | 6.72 | stats_ biology |
| 84 | 15 | 86943691 | 86944414 | 723 | gain | 2937 | | N | 20 | 12 | 7.73E-06 | 6.72 | stats_ biology |
| 85 | 15 | 86943691 | 86944414 | 723 | gain | 2946 | | N | 20 | 12 | 7.73E-06 | 6.72 | stats_ biology |
| 86 | 15 | 86943691 | 86944414 | 723 | gain | 2975 | | N | 20 | 12 | 7.73E-06 | 6.72 | stats_ biology |
| 87 | 15 | 86943691 | 86944414 | 723 | gain | 2976 | | N | 20 | 12 | 7.73E-06 | 6.72 | stats_ biology |
| 88 | 15 | 86943691 | 86944414 | 723 | gain | 2982 | | N | 20 | 12 | 7.73E-06 | 6.72 | stats_ biology |
| 89 | 15 | 86943691 | 86944414 | 723 | gain | 2995 | | N | 20 | 12 | 7.73E-06 | 6.72 | stats_ biology |
| 90 | 15 | 86943691 | 86944414 | 723 | gain | 2996 | | N | 20 | 12 | 7.73E-06 | 6.72 | stats_ biology |
| 91 | 15 | 86943691 | 86944414 | 723 | gain | 3002 | | N | 20 | 12 | 7.73E-06 | 6.72 | stats_ biology |
| 92 | 15 | 86941339 | 86943690 | 2351 | gain | 2901 | | N | 17 | 10 | 5.43E-05 | 6.46 | stats_ biology |
| 93 | 15 | 86941339 | 86943690 | 2351 | gain | 2923 | | N | 17 | 10 | 5.43E-05 | 6.46 | stats_ biology |
| 94 | 15 | 86941339 | 86943690 | 2351 | gain | 2926 | | N | 17 | 10 | 5.43E-05 | 6.46 | stats_ biology |
| 95 | 15 | 86941339 | 86943690 | 2351 | gain | 2937 | | N | 17 | 10 | 5.43E-05 | 6.46 | stats_ biology |
| 96 | 15 | 86941339 | 86943690 | 2351 | gain | 2975 | | N | 17 | 10 | 5.43E-05 | 6.46 | stats_ biology |
| 97 | 15 | 86941339 | 86943690 | 2351 | gain | 2976 | | N | 17 | 10 | 5.43E-05 | 6.46 | stats_ biology |
| 98 | 15 | 86941339 | 86943690 | 2351 | gain | 2982 | | N | 17 | 10 | 5.43E-05 | 6.46 | stats_ biology |
| 99 | 15 | 86941339 | 86943690 | 2351 | gain | 2995 | | N | 17 | 10 | 5.43E-05 | 6.46 | stats_ |

FIG. 2 (CONTINUED)

| SRN | Chromo some | CNV_ Subregion_ Start | CNV_ Subregion_ Stop | CNV_Sub region_Si ze | CNV_ Type | Endo_ Case_ ID(s) | RefSeq_ Gene_ Symbol | Exon_ over- lap | NVE_ cases | End_ cases | FET | OR | Category |
|---|---|---|---|---|---|---|---|---|---|---|---|---|---|
|  |  |  |  |  |  |  |  |  |  |  |  |  | biology |
| 100 | 15 | 86941339 | 86943690 | 2351 | gain | 2996 |  | N | 17 | 10 | 5.43E-05 | 6.46 | stats_ biology |
| 101 | 15 | 86941339 | 86943690 | 2351 | gain | 3002 |  | N | 17 | 10 | 5.43E-05 | 6.46 | stats_ biology |
| 102 | 2 | 191869063 | 191873037 | 3974 | loss | 2883 | MYO1B | Y | 22 | 20 | 2.15E-11 | 11.17 | stats |
| 103 | 2 | 191869063 | 191873037 | 3974 | loss | 2899 | MYO1B | Y | 22 | 20 | 2.15E-11 | 11.17 | stats |
| 104 | 2 | 191869063 | 191873037 | 3974 | loss | 2903 | MYO1B | Y | 22 | 20 | 2.15E-11 | 11.17 | stats |
| 105 | 2 | 191869063 | 191873037 | 3974 | loss | 2915 | MYO1B | Y | 22 | 20 | 2.15E-11 | 11.17 | stats |
| 106 | 2 | 191869063 | 191873037 | 3974 | loss | 2922 | MYO1B | Y | 22 | 20 | 2.15E-11 | 11.17 | stats |
| 107 | 2 | 191869063 | 191873037 | 3974 | loss | 2926 | MYO1B | Y | 22 | 20 | 2.15E-11 | 11.17 | stats |
| 108 | 2 | 191869063 | 191873037 | 3974 | loss | 2938 | MYO1B | Y | 22 | 20 | 2.15E-11 | 11.17 | stats |
| 109 | 2 | 191869063 | 191873037 | 3974 | loss | 2945 | MYO1B | Y | 22 | 20 | 2.15E-11 | 11.17 | stats |
| 110 | 2 | 191869063 | 191873037 | 3974 | loss | 2953 | MYO1B | Y | 22 | 20 | 2.15E-11 | 11.17 | stats |
| 111 | 2 | 191869063 | 191873037 | 3974 | loss | 2954 | MYO1B | Y | 22 | 20 | 2.15E-11 | 11.17 | stats |
| 112 | 2 | 191869063 | 191873037 | 3974 | loss | 2962 | MYO1B | Y | 22 | 20 | 2.15E-11 | 11.17 | stats |
| 113 | 2 | 191869063 | 191873037 | 3974 | loss | 2965 | MYO1B | Y | 22 | 20 | 2.15E-11 | 11.17 | stats |
| 114 | 2 | 191869063 | 191873037 | 3974 | loss | 2966 | MYO1B | Y | 22 | 20 | 2.15E-11 | 11.17 | stats |
| 115 | 2 | 191869063 | 191873037 | 3974 | loss | 2973 | MYO1B | Y | 22 | 20 | 2.15E-11 | 11.17 | stats |
| 116 | 2 | 191869063 | 191873037 | 3974 | loss | 2974 | MYO1B | Y | 22 | 20 | 2.15E-11 | 11.17 | stats |
| 117 | 2 | 191869063 | 191873037 | 3974 | loss | 2978 | MYO1B | Y | 22 | 20 | 2.15E-11 | 11.17 | stats |
| 118 | 2 | 191869063 | 191873037 | 3974 | loss | 2979 | MYO1B | Y | 22 | 20 | 2.15E-11 | 11.17 | stats |
| 119 | 2 | 191869063 | 191873037 | 3974 | loss | 2996 | MYO1B | Y | 22 | 20 | 2.15E-11 | 11.17 | stats |
| 120 | 2 | 191869063 | 191873037 | 3974 | loss | 2999 | MYO1B | Y | 22 | 20 | 2.15E-11 | 11.17 | stats |
| 121 | 2 | 191869063 | 191873037 | 3974 | loss | 3003 | MYO1B | Y | 22 | 20 | 2.15E-11 | 11.17 | stats |
| 122 | 2 | 191873038 | 191874236 | 1198 | loss | 2883 | MYO1B | N | 28 | 20 | 4.49E-10 | 8.72 | stats |
| 123 | 2 | 191873038 | 191874236 | 1198 | loss | 2899 | MYO1B | N | 28 | 20 | 4.49E-10 | 8.72 | stats |
| 124 | 2 | 191873038 | 191874236 | 1198 | loss | 2903 | MYO1B | N | 28 | 20 | 4.49E-10 | 8.72 | stats |
| 125 | 2 | 191873038 | 191874236 | 1198 | loss | 2915 | MYO1B | N | 28 | 20 | 4.49E-10 | 8.72 | stats |
| 126 | 2 | 191873038 | 191874236 | 1198 | loss | 2922 | MYO1B | N | 28 | 20 | 4.49E-10 | 8.72 | stats |

FIG. 2 (CONTINUED)

| SRN | Chromosome | CNV_Subregion_Start | CNV_Subregion_Stop | CNV_Subregion_Size | CNV_Type | Endo_Case_ID(s) | RefSeq_Gene_Symbol | Exon_overlap | NVE_cases | End_cases | FET | OR | Category |
|---|---|---|---|---|---|---|---|---|---|---|---|---|---|
| 127 | 2 | 191873038 | 191874236 | 1198 | loss | 2926 | MYO1B | N | 28 | 20 | 4.49E-10 | 8.72 | stats |
| 128 | 2 | 191873038 | 191874236 | 1198 | loss | 2938 | MYO1B | N | 28 | 20 | 4.49E-10 | 8.72 | stats |
| 129 | 2 | 191873038 | 191874236 | 1198 | loss | 2945 | MYO1B | N | 28 | 20 | 4.49E-10 | 8.72 | stats |
| 130 | 2 | 191873038 | 191874236 | 1198 | loss | 2953 | MYO1B | N | 28 | 20 | 4.49E-10 | 8.72 | stats |
| 131 | 2 | 191873038 | 191874236 | 1198 | loss | 2954 | MYO1B | N | 28 | 20 | 4.49E-10 | 8.72 | stats |
| 132 | 2 | 191873038 | 191874236 | 1198 | loss | 2962 | MYO1B | N | 28 | 20 | 4.49E-10 | 8.72 | stats |
| 133 | 2 | 191873038 | 191874236 | 1198 | loss | 2965 | MYO1B | N | 28 | 20 | 4.49E-10 | 8.72 | stats |
| 134 | 2 | 191873038 | 191874236 | 1198 | loss | 2966 | MYO1B | N | 28 | 20 | 4.49E-10 | 8.72 | stats |
| 135 | 2 | 191873038 | 191874236 | 1198 | loss | 2973 | MYO1B | N | 28 | 20 | 4.49E-10 | 8.72 | stats |
| 136 | 2 | 191873038 | 191874236 | 1198 | loss | 2974 | MYO1B | N | 28 | 20 | 4.49E-10 | 8.72 | stats |
| 137 | 2 | 191873038 | 191874236 | 1198 | loss | 2978 | MYO1B | N | 28 | 20 | 4.49E-10 | 8.72 | stats |
| 138 | 2 | 191873038 | 191874236 | 1198 | loss | 2979 | MYO1B | N | 28 | 20 | 4.49E-10 | 8.72 | stats |
| 139 | 2 | 191873038 | 191874236 | 1198 | loss | 2996 | MYO1B | N | 28 | 20 | 4.49E-10 | 8.72 | stats |
| 140 | 2 | 191873038 | 191874236 | 1198 | loss | 2999 | MYO1B | N | 28 | 20 | 4.49E-10 | 8.72 | stats |
| 141 | 2 | 191873038 | 191874236 | 1198 | loss | 3003 | MYO1B | N | 28 | 20 | 4.49E-10 | 8.72 | stats |
| 142 | 6 | 47731384 | 47734315 | 2931 | loss | 2905 | GPR111 | Y | 23 | 15 | 2.18E-07 | 7.53 | stats |
| 143 | 6 | 47731384 | 47734315 | 2931 | loss | 2909 | GPR111 | Y | 23 | 15 | 2.18E-07 | 7.53 | stats |
| 144 | 6 | 47731384 | 47734315 | 2931 | loss | 2915 | GPR111 | Y | 23 | 15 | 2.18E-07 | 7.53 | stats |
| 145 | 6 | 47731384 | 47734315 | 2931 | loss | 2917 | GPR111 | Y | 23 | 15 | 2.18E-07 | 7.53 | stats |
| 146 | 6 | 47731384 | 47734315 | 2931 | loss | 2919 | GPR111 | Y | 23 | 15 | 2.18E-07 | 7.53 | stats |
| 147 | 6 | 47731384 | 47734315 | 2931 | loss | 2924 | GPR111 | Y | 23 | 15 | 2.18E-07 | 7.53 | stats |
| 148 | 6 | 47731384 | 47734315 | 2931 | loss | 2926 | GPR111 | Y | 23 | 15 | 2.18E-07 | 7.53 | stats |
| 149 | 6 | 47731384 | 47734315 | 2931 | loss | 2930 | GPR111 | Y | 23 | 15 | 2.18E-07 | 7.53 | stats |
| 150 | 6 | 47731384 | 47734315 | 2931 | loss | 2933 | GPR111 | Y | 23 | 15 | 2.18E-07 | 7.53 | stats |
| 151 | 6 | 47731384 | 47734315 | 2931 | loss | 2946 | GPR111 | Y | 23 | 15 | 2.18E-07 | 7.53 | stats |
| 152 | 6 | 47731384 | 47734315 | 2931 | loss | 2951 | GPR111 | Y | 23 | 15 | 2.18E-07 | 7.53 | stats |
| 153 | 6 | 47731384 | 47734315 | 2931 | loss | 2961 | GPR111 | Y | 23 | 15 | 2.18E-07 | 7.53 | stats |
| 154 | 6 | 47731384 | 47734315 | 2931 | loss | 2976 | GPR111 | Y | 23 | 15 | 2.18E-07 | 7.53 | stats |
| 155 | 6 | 47731384 | 47734315 | 2931 | loss | 2983 | GPR111 | Y | 23 | 15 | 2.18E-07 | 7.53 | stats |
| 156 | 6 | 47731384 | 47734315 | 2931 | loss | 2985 | GPR111 | Y | 23 | 15 | 2.18E-07 | 7.53 | stats |

FIG. 2 (CONTINUED)

| SRN | Chromo some | CNV_ Subregion_ Start | CNV_ Subregion_ Stop | CNV_Sub region_Si ze | CNV_ Type | Endo_ Case_ ID(s) | RefSeq_ Gene_ Symbol | Exon_ over- lap | NVE_ cases | End_ cases | FET | OR | Category |
|---|---|---|---|---|---|---|---|---|---|---|---|---|---|
| 157 | 6 | 70290311 | 70295413 | 5102 | gain | 2910 | | N | 45 | 16 | 4.16E-05 | 4.06 | stats |
| 158 | 6 | 70290311 | 70295413 | 5102 | gain | 2914 | | N | 45 | 16 | 4.16E-05 | 4.06 | stats |
| 159 | 6 | 70290311 | 70295413 | 5102 | gain | 2919 | | N | 45 | 16 | 4.16E-05 | 4.06 | stats |
| 160 | 6 | 70290311 | 70295413 | 5102 | gain | 2921 | | N | 45 | 16 | 4.16E-05 | 4.06 | stats |
| 161 | 6 | 70290311 | 70295413 | 5102 | gain | 2923 | | N | 45 | 16 | 4.16E-05 | 4.06 | stats |
| 162 | 6 | 70290311 | 70295413 | 5102 | gain | 2924 | | N | 45 | 16 | 4.16E-05 | 4.06 | stats |
| 163 | 6 | 70290311 | 70295413 | 5102 | gain | 2937 | | N | 45 | 16 | 4.16E-05 | 4.06 | stats |
| 164 | 6 | 70290311 | 70295413 | 5102 | gain | 2943 | | N | 45 | 16 | 4.16E-05 | 4.06 | stats |
| 165 | 6 | 70290311 | 70295413 | 5102 | gain | 2944 | | N | 45 | 16 | 4.16E-05 | 4.06 | stats |
| 166 | 6 | 70290311 | 70295413 | 5102 | gain | 2948 | | N | 45 | 16 | 4.16E-05 | 4.06 | stats |
| 167 | 6 | 70290311 | 70295413 | 5102 | gain | 2959 | | N | 45 | 16 | 4.16E-05 | 4.06 | stats |
| 168 | 6 | 70290311 | 70295413 | 5102 | gain | 2979 | | N | 45 | 16 | 4.16E-05 | 4.06 | stats |
| 169 | 6 | 70290311 | 70295413 | 5102 | gain | 2981 | | N | 45 | 16 | 4.16E-05 | 4.06 | stats |
| 170 | 6 | 70290311 | 70295413 | 5102 | gain | 2982 | | N | 45 | 16 | 4.16E-05 | 4.06 | stats |
| 171 | 6 | 70290311 | 70295413 | 5102 | gain | 2983 | | N | 45 | 16 | 4.16E-05 | 4.06 | stats |
| 172 | 6 | 70290311 | 70295413 | 5102 | gain | 2985 | | N | 45 | 16 | 4.16E-05 | 4.06 | stats |

FIG. 2 (CONTINUED)

| RefSeq Gene Symbol | Exon_o verlap | NCBI_Gene ID | Gene_Description | RefSeq_Summary |
|---|---|---|---|---|
| ACCS | exonic | 84680 | 1-aminocyclopropane-1-carboxylate synthase-like protein 1 | N/A |
| ARMC5 | exonic | 79798 | armadillo repeat-containing protein 5 isoform a precursor | N/A |
| AS3MT | exonic | 57412 | arsenite methyltransferase | AS3MT catalyzes the transfer of a methyl group from S-adenosyl-L-methionine (AdoMet) to trivalent arsenical and may play a role in arsenic metabolism . Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: BC119637.1, BC119637.1 [ECO:0000332] RNAseq introns :: single sample supports all introns ERS025084, ERS025085 [ECO:0000348] ##Evidence-Data-END## |
| BNC2 | exonic | 54796 | zinc finger protein basonuclin-2 | N/A |

FIG. 3

| RefSeq Gene Symbol | Exon_overlap | NCBI_Gene ID | Gene_Description | RefSeq_Summary |
|---|---|---|---|---|
| BOK | exonic | 666 | bcl-2-related ovarian killer protein | The protein encoded by this gene belongs to the BCL2 family, members of which form homo- or heterodimers, and act as anti- or proapoptotic regulators that are involved in a wide variety of cellular processes. Studies in rat show that this protein has restricted expression in reproductive tissues, interacts strongly with some antiapoptotic BCL2 proteins, not at all with proapoptotic BCL2 proteins, and induces apoptosis in transfected cells. Thus, this protein represents a proapoptotic member of the BCL2 family. ##Evidence-Data-START## Transcript exon combination :: BX460019.2, BX334491.2 [ECO:0000332] RNAseq introns :: single sample supports all introns ERS025081, ERS025082 [ECO:0000348] ##Evidence-Data-END## |
| BOK-AS1 | exonic | 100379249 | N/A | N/A |
| C10orf32 | exonic | 119032 | UPF0693 protein C10orf32 | N/A |

FIG. 3 (CONTINUED)

| RefSeq Gene Symbol | Exon_overlap | NCBI_Gene ID | Gene_Description | RefSeq_Summary |
|---|---|---|---|---|
| C10orf32-AS3MT | exonic | 100528007 | This locus represents naturally occurring read-through transcription between the neighboring C10orf32 (chromosome 10 open reading frame 32) and AS3MT (arsenic, +3 oxidation state, methyltransferase) genes. The read-through transcript is a candidate for nonsense-mediated mRNA decay (NMD), and is therefore unlikely to produce a protein product. [provided by RefSeq, Dec 2010]. Sequence Note: This RefSeq record was created from transcript and genomic sequence data to make the sequence consistent with the reference genome assembly. The genomic coordinates used for the transcript record were based on transcript alignments. ##RefSeq-Attributes-START## readthrough transcript :: | This locus represents naturally occurring read-through transcription between the neighboring C10orf32 (chromosome 10 open reading frame 32) and AS3MT (arsenic, +3 oxidation state, methyltransferase) genes. The read-through transcript is a candidate for nonsense-mediated mRNA decay (NMD), and is therefore unlikely to produce a protein product. Sequence Note: This RefSeq record was created from transcript and genomic sequence data to make the sequence consistent with the reference genome assembly. The genomic coordinates used for the transcript record were based on transcript alignments. ##RefSeq-Attributes-START## readthrough transcript :: includes exons from GeneID 57412, 119032 ##RefSeq-Attributes-END## ##Evidence-Data-START## Transcript exon combination :: BC040069.1 [ECO:0000332] RNAseq introns :: mixed/partial sample support ERS025083, ERS025084 [ECO:0000350] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| C16orf58 | exonic | 64755 | UPF0420 protein C16orf58 | This gene encodes a putative transmembrane protein containing a conserved DUF647 domain that may be involved in protein-protein interaction. The encoded protein is related to a plant protein that participates in ultraviolet B light-sensing during root morphogenesis. ##Evidence-Data-START## Transcript exon combination :: AK023930.1, AK222913.1 [ECO:0000332] RNAseq introns :: mixed/partial sample support ERS025081, ERS025082 [ECO:0000350] ##Evidence-Data-END## |
| CNNM2 | exonic | 54805 | metal transporter CNNM2 isoform 1 | This gene encodes a member of the ancient conserved domain containing protein family. Members of this protein family contain a cyclin box motif and have structural similarity to the cyclins. The encoded protein may play an important role in magnesium homeostasis by mediating the epithelial transport and renal reabsorption of Mg2+. Mutations in this gene are associated with renal hypomagnesemia. Alternatively spliced transcript variants encoding multiple isoforms have been observed for this gene. Transcript Variant: This variant (1) represents the longest transcript and encodes the longest isoform (1). ##Evidence-Data-START## Transcript exon combination :: AF216962.1, AK023066.1 [ECO:0000332] RNAseq introns :: single sample supports all introns ERS025081, ERS025082 [ECO:0000348] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| CRHR2 | exonic | 1395 | corticotropin-releasing factor receptor 2 isoform 1 | The protein encoded by this gene belongs to the G-protein coupled receptor 2 family, and the subfamily of corticotropin releasing hormone receptor. This receptor shows high affinity for corticotropin releasing hormone (CRH), and also binds CRH related peptides such as urocortin. CRH is synthesized in the hypothalamus, and plays an important role in coordinating the endocrine, autonomic, and behavioral responses to stress and immune challenge. Studies in mice suggest that this receptor maybe involved in mediating cardiovascular homeostasis. Alternatively spliced transcript variants encoding different isoforms have been described for this gene. Transcript Variant: This variant (1) represents the predominant transcript, and encodes isoform 1 (also known as alpha isoform). ##Evidence-Data-START## Transcript exon combination :: U34587.1, AK313661.1 [ECO:0000332] RNAseq introns :: mixed/partial sample support ERS025082, ERS025083 [ECO:0000350] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| CYP17A1 | exonic | 1586 | steroid 17-alpha-hydroxylase/17,20 lyase precursor | This gene encodes a member of the cytochrome P450 superfamily of enzymes. The cytochrome P450 proteins are monooxygenases which catalyze many reactions involved in drug metabolism and synthesis of cholesterol, steroids and other lipids. This protein localizes to the endoplasmic reticulum. It has both 17alpha-hydroxylase and 17,20-lyase activities and is a key enzyme in the steroidogenic pathway that produces progestins, mineralocorticoids, glucocorticoids, androgens, and estrogens. Mutations in this gene are associated with isolated steroid-17 alpha-hydroxylase deficiency, 17-alpha-hydroxylase/17,20-lyase deficiency, pseudohermaphroditism, and adrenal hyperplasia. ##Evidence-Data-START## Transcript exon combination :: BC062997.1, AK289898.1 [ECO:0000332] RNAseq introns :: single sample supports all introns ERS025098 [ECO:0000348] ##Evidence-Data-END## |

FIG. 3 (CONTINUED)

| RefSeq Gene Symbol | Exon_o verlap | NCBI_Gene ID | Gene Description | RefSeq Summary |
|---|---|---|---|---|
| DNAJC6 | exonic | 9829 | putative tyrosine-protein phosphatase auxilin isoform 1 | DNAJC6 belongs to the evolutionarily conserved DNAJ/HSP40 family of proteins, which regulate molecular chaperone activity by stimulating ATPase activity. DNAJ proteins may have up to 3 distinct domains: a conserved 70-amino acid J domain, usually at the N terminus, a glycine/phenylalanine (G/F)-rich region, and a cysteine-rich domain containing 4 motifs resembling a zinc finger domain. Transcript Variant: This variant (1) represents the longest transcript and encodes the longest isoform (1). Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: BX647203.1, BC109280.1 [ECO:0000332] ##Evidence-Data-END## |

FIG. 3 (CONTINUED)

| RefSeq Gene Symbol | Exon_overlap | NCBI_Gene_ID | Gene Description | RefSeq_Summary |
|---|---|---|---|---|
| DPP6 | intronic | 1804 | dipeptidyl aminopeptidase-like protein 6 isoform 1 | This gene encodes a single-pass type II membrane protein that is a member of the S9B family in clan SC of the serine proteases. This protein has no detectable protease activity, most likely due to the absence of the conserved serine residue normally present in the catalytic domain of serine proteases. However, it does bind specific voltage-gated potassium channels and alters their expression and biophysical properties. Alternate transcriptional splice variants, encoding different isoforms, have been characterized. Transcript Variant: This variant (1) encodes the longest isoform (1, also referred to as L). Sequence Note: This RefSeq record was created from transcript and genomic sequence data to make the sequence consistent with the reference genome assembly. The genomic coordinates used for the transcript record were based on transcript alignments. |

FIG. 3 (CONTINUED)

| RefSeq Gene Symbol | Exon_overlap | NCBI_Gene ID | Gene_Description | RefSeq_Summary |
|---|---|---|---|---|
| FUT9 | intronic | 10690 | alpha-(1,3)-fucosyltransferase | The protein encoded by this gene belongs to the glycosyltransferase family. It is localized to the golgi, and catalyzes the last step in the biosynthesis of Lewis X (LeX) antigen, the addition of a fucose to precursor polysaccharides. This protein is one of the few fucosyltransferases that synthesizes the LeX oligosaccharide (CD15) expressed in the organ buds progressing in mesenchyma during embryogenesis. It is also responsible for the expression of CD15 in mature granulocytes. A common haplotype of this gene has also been associated with susceptibility to placental malaria infection. The RefSeq was created from transcript and genomic sequence data because no single transcript was available for the full length of the gene. The extent of this transcript is supported by transcript alignments. ##Evidence-Data-START## Transcript exon combination :: CK904220.1, AB023021.1 [ECO:0000332] RNAseq introns :: single sample supports all introns ERS025082, ERS025098 [ECO:0000348] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| GIGYF2 | intronic | 26058 | PERQ amino acid-rich with GYF domain-containing protein 2 isoform a | This gene contains CAG trinucleotide repeats and encodes a protein containing several stretches of polyglutamine residues. The encoded protein may be involved in the regulation of tyrosine kinase receptor signaling. This gene is located in a chromosomal region that was genetically linked to Parkinson disease type 11, and mutations in this gene were thought to be causative for this disease. However, more recent studies in different populations have been unable to replicate this association. Alternative splicing results in multiple transcript variants. Transcript Variant: This variant (1) encodes the longest isoform (a). Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: BC145775.1, AB014542.2 [ECO:0000332] RNAseq introns :: single sample supports all introns ERS025084, ERS025088 [ECO:0000348] ##Evidence-Data-END## |
| GPR111 | exonic | 222611 | probable G-protein coupled receptor 111 precursor | N/A |

FIG. 3 (CONTINUED)

| RefSeq Gene Symbol | Exon_overlap | NCBI_Gene ID | Gene Description | RefSeq_Summary |
|---|---|---|---|---|
| HMGB3 | both | 3149 | high mobility group protein B3 | HMGB3 belongs to the high mobility group (HMG) protein superfamily. Like HMG1 (MIM 163905) and HMG2 (MIM 163906), HMGB3 contains DNA-binding HMG box domains and is classified into the HMG box subfamily. Members of the HMG box subfamily are thought to play a fundamental role in DNA replication, nucleosome assembly and transcription. ##Evidence-Data-START## Transcript exon combination :: Y10043.1, BG176733.1 [ECO:0000332] RNAseq introns :: single sample supports all introns ERS025081, ERS025082 [ECO:0000348] ##Evidence-Data-END## |
| IPMK | exonic | 253430 | inositol polyphosphate multikinase | This gene encodes a member of the inositol phosphokinase family. The encoded protein has 3-kinase, 5-kinase and 6-kinase activities on phosphorylated inositol substrates. The encoded protein plays an important role in the biosynthesis of inositol 1,3,4,5,6-pentakisphosphate, and has a preferred 5-kinase activity. This gene may play a role in nuclear mRNA export. Pseudogenes of this gene are located on the long arm of chromosome 13 and the short arm of chromosome 19. [provided by RefSeq, Dec 2010] Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: BC065709.1, BC016612.1 [ECO:0000332] RNAseq introns :: single sample supports all introns ERS025081, ERS025084 [ECO:0000348] ##Evidence-Data-END## |

FIG. 3 (CONTINUED)

| RefSeq Gene Symbol | Exon_o verlap | NCBI_Gene ID | Gene_Description | RefSeq_Summary |
|---|---|---|---|---|
| LARP1B | exonic | 55132 | la-related protein 1B isoform 1 | This gene encodes a protein containing domains found in the La related protein of Drosophila melanogaster. La motif-containing proteins are thought to be RNA-binding proteins, where the La motif and adjacent amino acids fold into an RNA recognition motif. The La motif is also found in proteins unrelated to the La protein. Alternative splicing has been observed at this locus and multiple variants, encoding distinct isoforms, are described. Additional splice variation has been identified but the full-length nature of these transcripts has not been determined. Transcript Variant: This variant (1) represents the longest transcript and encodes the longest isoform (1). ##Evidence-Data-START## RNAseq introns :: mixed/partial sample support ERS025085 [ECO:0000350] ##Evidence-Data-END## |

FIG. 3 (CONTINUED)

| RefSeq Gene Symbol | Exon_o verlap | NCBI_Gene ID | Gene_Description | RefSeq_Summary |
|---|---|---|---|---|
| LEPR | exonic | 3953 | leptin receptor isoform 1 precursor | The protein encoded by this gene belongs to the gp130 family of cytokine receptors that are known to stimulate gene transcription via activation of cytosolic STAT proteins. This protein is a receptor for leptin (an adipocyte-specific hormone that regulates body weight), and is involved in the regulation of fat metabolism, as well as in a novel hematopoietic pathway that is required for normal lymphopoiesis. Mutations in this gene have been associated with obesity and pituitary dysfunction. Alternatively spliced transcript variants encoding different isoforms have been described for this gene. It is noteworthy that this gene and LEPROT gene (GeneID:54741) share the same promoter and the first 2 exons, however, encode distinct proteins (PMID:9207021).{provided by RefSeq, Nov 2010}.Transcript Variant: This variant (1) encodes the longest isoform (1). ##Evidence-Data-START## Transcript exon combination :: U43168.1 [ECO:0000332] RNAseq introns :: single sample supports all introns ERS025084, ERS025088 [ECO:0000348] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| LEPROT | exonic | 54741 | leptin receptor gene-related protein isoform 1 | LEPROT is associated with the Golgi complex and endosomes and has a role in cell surface expression of growth hormone receptor (GHR; MIM 600946) and leptin receptor (OBR, or LEPR; MIM 601007), thereby altering receptor-mediated cell signaling. Transcript Variant: This variant (1) is dominant and encodes the shorter isoform (1). Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: Y12670.1, AK074841.1 [ECO:0000332] RNAseq introns :: single sample supports all introns ERS025081, ERS025082 [ECO:0000348] ##Evidence-Data-END## |
| MAGEA11 | exonic | 4110 | melanoma-associated antigen 11 isoform a | This gene is a member of the MAGEA gene family. The members of this family encode proteins with 50 to 80% sequence identity to each other. The promoters and first exons of the MAGEA genes show considerable variability, suggesting that the existence of this gene family enables the same function to be expressed under different transcriptional controls. The MAGEA genes are clustered at chromosomal location Xq28. They have been implicated in some hereditary disorders, such as dyskeratosis congenita. Two transcript variants encoding different isoforms have been found for this gene. Transcript Variant: This variant (1) encodes the longer isoform (a). ##Evidence-Data-END## |

FIG. 3 (CONTINUED)

| RefSeq Gene Symbol | Exon_o verlap | NCBI_Gene ID | Gene_Description | RefSeq_Summary |
|---|---|---|---|---|
| MKRN1 | exonic | 23608 | E3 ubiquitin-protein ligase makorin-1 isoform 1 | The Makorin ring finger protein-1 gene (MKRN1) is a highly transcribed, intron-containing source for a family of intronless mammalian genes encoding a novel class of zinc finger proteins. Phylogenetic analyses indicate that the MKRN1 gene is the ancestral founder of this gene family. Transcript Variant: This variant (1) represents the longer transcript and encodes the longer isoform (1). ##Evidence-Data-START## Transcript exon combination :: BC025955.1, AL136812.1 [ECO:0000332] RNAseq introns :: mixed/partial sample support ERS025081, ERS025082 [ECO:0000350] ##Evidence-Data-END## |
| MSN | exonic | 4478 | moesin | Moesin (for membrane-organizing extension spike protein) is a member of the ERM family which includes ezrin and radixin. ERM proteins appear to function as cross-linkers between plasma membranes and actin-based cytoskeletons. Moesin is localized to filopodia and other membranous protrusions that are important for cell-cell recognition and signaling and for cell movement. ##Evidence-Data-START## Transcript exon combination :: M69066.1, BC017293.2 [ECO:0000332] RNAseq introns :: single sample supports all introns ERS025081, ERS025082 [ECO:0000348] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| MUC4 | exonic | 4585 | mucin-4 isoform a precursor | The major constituents of mucus, the viscous secretion that covers epithelial surfaces such as those in the trachea, colon, and cervix, are highly glycosylated proteins called mucins. These glycoproteins play important roles in the protection of the epithelial cells and have been implicated in epithelial renewal and differentiation. This gene encodes an integral membrane glycoprotein found on the cell surface, although secreted isoforms may exist. At least two dozen transcript variants of this gene have been found, although for many of them the full-length transcript has not been determined or they are found only in tumor tissues. This gene contains a region in the coding sequence which has a variable number (>100) of 48 nt tandem repeats. [provided by RefSeq, Jul 2008]. Transcript Variant: This variant (1), also called sv0, is the longest transcript and encodes the full-length isoform (a). Isoform a is thought to be a membrane-bound protein. ##Evidence-Data-START## RNAseq introns :: mixed/partial sample support ERS025084, ERS025085 [ECO:0000350] ##Evidence-Data-END## |
| MYADML | exonic | 151325 | N/A | N/A |
| MYO1B | both | 4430 | unconventional myosin-Ib isoform 1 | N/A |

FIG. 3 (CONTINUED)

| RefSeq Gene Symbol | Exon_o verlap | NCBI_Gene ID | Gene_Description | RefSeq_Summary |
|---|---|---|---|---|
| NBPF1 | exonic | 55672 | neuroblastoma breakpoint family member 1 | This gene is a member of the neuroblastoma breakpoint family (NBPF) which consists of dozens of recently duplicated genes primarily located in segmental duplications on human chromosome 1. This gene family has experienced its greatest expansion within the human lineage and has expanded, to a lesser extent, among primates in general. Members of this gene family are characterized by tandemly repeated copies of DUF1220 protein domains. Gene copy number variations in the human chromosomal region 1q21.1, where most DUF1220 domains are located, have been implicated in a number of developmental and neurogenetic diseases such as microcephaly, macrocephaly, autism, schizophrenia, mental retardation, congenital heart disease, neuroblastoma, and congenital kidney and urinary tract anomalies. Altered expression of some gene family members is associated with several types of cancer. This gene family contains numerous pseudogenes. ##Evidence-Data-START## RNAseq introns :: mixed/partial sample support ERS025081, ERS025082 [ECO:0000350] ##Evidence-Data-END## |

FIG. 3 (CONTINUED)

| RefSeq Gene Symbol | Exon_overlap | NCBI_Gene ID | Gene_Description | RefSeq_Summary |
|---|---|---|---|---|
| NCOA1 | exonic | 8648 | nuclear receptor coactivator 1, isoform 1 | The protein encoded by this gene acts as a transcriptional coactivator for steroid and nuclear hormone receptors. It is a member of the p160/steroid receptor coactivator (SRC) family and like other family members has histone acetyltransferase activity and contains a nuclear localization signal, as well as bHLH and PAS domains. The product of this gene binds nuclear receptors directly and stimulates the transcriptional activities in a hormone-dependent fashion. Alternatively spliced transcript variants encoding different isoforms have been identified. [provided by RefSeq, Jul 2008]. Transcript Variant: This variant (1), also known as SRC1a, encodes the longest isoform (1). ##Evidence-Data-START## CDS exon combination :: AJ000883.1, U90661.1 [ECO:0000331] RNAseq introns :: single sample supports all introns ERS025081, ERS025082 [ECO:00003481] ##Evidence-Data-END## |

FIG. 3 (CONTINUED)

| RefSeq Gene Symbol | Expn_o verlap | NCBI_Gene ID | Gene_Description | RefSeq_Summary |
|---|---|---|---|---|
| PDE1C | intronic | 5137 | calcium/calmodulin-dependent 3',5'-cyclic nucleotide phosphodiesterase 1C isoform 1 | Cyclic nucleotide phosphodiesterases (PDEs) catalyze hydrolysis of the cyclic nucleotides cAMP and cGMP to the corresponding nucleoside 5-prime-monophosphates. Mammalian PDEs have been classified into several families based on their biochemical properties. Members of the PDE1 family, such as PDE1C, are calmodulin (see MIM 114180)-dependent PDEs (CaM-PDEs) that are stimulated by a calcium-calmodulin complex (Repaske et al., 1992 [PubMed 1326532]).[supplied by OMIM, Oct 2009]. Transcript Variant: This variant (1) differs in the 5' and 3' UTR and has multiple coding region differences, compared to variant 3. These differences result in an isoform (1) with distinct N- and C-termini, compared to isoform 3. Variants 1 and 4 encode the same protein. Isoform 1 is also known as HCam-3B. This record was created from transcript and genomic sequence data to make the sequence consistent with the reference genome assembly. The genomic coordinates used for the transcript record were based on transcript alignments. ##Evidence-Data-START## Transcript exon combination :: BC022479.1 [ECO:0000332] RNAseq introns :: mixed/partial sample support ERS025081, ERS025082 [ECO:0000350] ##Evidence-Data-END## |
| PGRMC2 | exonic | 10424 | membrane-associated progesterone receptor component 2 | N/A |

FIG. 3 (CONTINUED)

| RefSeq Gene Symbol | Exon_overlap | NCBI_Gene ID | Gene_Description | RefSeq_Summary |
|---|---|---|---|---|
| PLA2G4C | exonic | 8605 | cytosolic phospholipase A2 gamma isoform 1 precursor | This gene encodes a protein which is a member of the phospholipase A2 enzyme family which hydrolyzes glycerophospholipids to produce free fatty acids and lysophospholipids, both of which serve as precursors in the production of signaling molecules. The encoded protein has been shown to be a calcium-independent and membrane bound enzyme. Multiple transcript variants encoding different isoforms have been found for this gene.Transcript Variant: This variant (1) encodes the predominant isoform (1). ##Evidence-Data-START## Transcript exon combination :: AF065214.1, AF065214.1, AF058921.1 [ECO:0000332] RNAseq introns :: single sample supports all introns ERS025084, ERS025088 [ECO:0000348] ##Evidence-Data-END## |

FIG. 3 (CONTINUED)

| RefSeq Gene Symbol | Exon_overlap | NCBI_Gene ID | Gene Description | RefSeq_Summary |
|---|---|---|---|---|
| | | | | This gene encodes a cytoplasmic protein tyrosine kinase which is found concentrated in the focal adhesions that form between cells growing in the presence of extracellular matrix constituents. The encoded protein is a member of the FAK subfamily of protein tyrosine kinases but lacks significant sequence similarity to kinases from other subfamilies. Activation of this gene may be an important early step in cell growth and intracellular signal transduction pathways triggered in response to certain neural peptides or to cell interactions with the extracellular matrix. Several transcript variants encoding different isoforms have been found for this gene, but the full-length natures of only three of them have been determined. Transcript Variant: This variant (1) differs in the 5' UTR and coding sequence compared to variant 2. The resulting isoform (a) is shorter at the N-terminus compared to isoform b. ##Evidence-Data-START## Transcript exon combination :: L13616.1 [ECO:0000332] RNAseq introns :: mixed/partial sample support ERS025081, ERS025082 |
| PTK2 | both | 5747 | focal adhesion kinase 1 isoform a | [ECO:0000350] ##Evidence-Data-END## |
| RAB19 | exonic | 401409 | ras-related protein Rab-19 | N/A |

FIG. 3 (CONTINUED)

| RefSeq_Gene_Symbol | Exon_overlap | NCBI_Gene_ID | Gene_Description | RefSeq_Summary |
|---|---|---|---|---|
| RXFP1 | intronic | 59350 | This gene encodes a member of the leucine-rich repeat-containing subgroup of the G protein-coupled 7-transmembrane receptor superfamily. The encoded protein plays a critical role in sperm motility, pregnancy and parturition as a receptor for the protein hormone relaxin. Decreased expression of this gene may play a role in endometriosis. Alternatively spliced transcript variants encoding multiple isoforms have been observed for this gene. [provided by RefSeq, Dec 2011]. Transcript Variant: This variant (10) uses an alternate internal splice site, compared to variant 1. This variant is represented as non-coding due to the presence of an upstream ORF that is predicted to interfere with translation of the longest ORF; translation of | This gene encodes a member of the leucine-rich repeat-containing subgroup of the G protein-coupled 7-transmembrane receptor superfamily. The encoded protein plays a critical role in sperm motility, pregnancy and parturition as a receptor for the protein hormone relaxin. Decreased expression of this gene may play a role in endometriosis. Alternatively spliced transcript variants encoding multiple isoforms have been observed for this gene. Transcript Variant: This variant (10) uses an alternate internal splice site, compared to variant 1. This variant is represented as non-coding due to the presence of an upstream ORF that is predicted to interfere with translation of the longest ORF; translation of the upstream ORF renders the transcript a candidate for nonsense-mediated mRNA decay (NMD). ##Evidence-Data-START## RNAseq introns :: mixed/partial sample support ERS025081, ERS025082 [ECO:0000350] ##Evidence-Data-END## |

FIG. 3 (CONTINUED)

| RefSeq Gene Symbol | Exon_o verlap | NCBI_Gene ID | Gene_Description | RefSeq_Summary |
|---|---|---|---|---|
| SLC5A2 | exonic | 6524 | sodium/glucose cotransporter 2 | This gene encodes a member of the sodium glucose cotransporter family which are sodium-dependent glucose transport proteins. The encoded protein is the major cotransporter involved in glucose reabsorption in the kidney. Mutations in this gene are associated with renal glucosuria. ##Evidence-Data-START## Transcript exon combination :: M95549.1 [ECO:0000332] RNAseq introns :: single sample supports all introns ERS025084, ERS025038 [ECO:0000348] ##Evidence-Data-END## |
| TGFB1I1 | exonic | 7041 | transforming growth factor beta-1-induced transcript 1 protein isoform 1 | This gene encodes a coactivator of the androgen receptor, a transcription factor which is activated by androgen and has a key role in male sexual differentiation. The encoded protein is thought to regulate androgen receptor activity and may have a role to play in the treatment of prostate cancer. Multiple transcript variants encoding different isoforms have been found for this gene. Transcript Variant: This variant (1) represents the longest transcript and encodes the longer protein (isoform 1). Sequence Note: This RefSeq record was created from transcript and genomic sequence data to make the sequence consistent with the reference genome assembly. The genomic coordinates used for the transcript record were based on transcript alignments. ##Evidence-Data-START## Transcript exon combination :: AK313327.1, AB007836.1 [ECO:0000332] RNAseq introns :: single sample supports all introns ERS025081, ERS025083 [ECO:0000348] ##Evidence-Data-END## |

FIG. 3 (CONTINUED)

| RefSeq Gene Symbol | Exon_overlap | NCBI Gene ID | Gene Description | RefSeq_Summary |
|---|---|---|---|---|
| TGFBR3 | intronic | 7049 | This locus encodes the transforming growth factor (TGF)-beta type III receptor. The encoded receptor is a membrane proteoglycan that often functions as a co-receptor with other TGF-beta receptor superfamily members. Ectodomain shedding produces soluble TGFBR3, which may inhibit TGFB signaling. Decreased expression of this receptor has been observed in various cancers. Alternatively spliced transcript variants encoding different isoforms have been identified for this gene. [provided by RefSeq, Sep 2010]. Transcript Variant: This variant (4) contains an alternate internal exon, compared to variant 1. This variant is represented as non-coding because the use of the 5'-most supported | This locus encodes the transforming growth factor (TGF)-beta type III receptor. The encoded receptor is a membrane proteoglycan that often functions as a co-receptor with other TGF-beta receptor superfamily members. Ectodomain shedding produces soluble TGFBR3, which may inhibit TGFB signaling. Decreased expression of this receptor has been observed in various cancers. Alternatively spliced transcript variants encoding different isoforms have been identified for this gene. Transcript Variant: This variant (4) contains an alternate internal exon, compared to variant 1. This variant is represented as non-coding because the use of the 5'-most supported translational start codon, as used in variant 1, renders the transcript a candidate for nonsense-mediated mRNA decay (NMD). Sequence Note: This RefSeq record was created from transcript and genomic sequence data to make the sequence consistent with the reference genome assembly. The genomic coordinates used for the transcript record were based on transcript alignments. ##Evidence-Data-START## RNAseq introns :: mixed/partial sample support ERS025081, ERS025082 [ECO:0000350] ##Evidence-Data-END## |

FIG. 3 (CONTINUED)

| RefSeq Gene Symbol | Exon_o verlap | NCBI_Gene ID | Gene Description | RefSeq_Summary |
|---|---|---|---|---|
| TSHR | exonic | 7253 | thyrotropin receptor isoform 1 precursor | The protein encoded by this gene is a membrane protein and a major controller of thyroid cell metabolism. The encoded protein is a receptor for thyrotropin and thyrostimulin, and its activity is mediated by adenylate cyclase. Defects in this gene are a cause of several types of hyperthyroidism. Three transcript variants encoding different isoforms have been found for this gene. Transcript Variant: This variant (1) represents the longer transcript and it encodes the longer protein (isoform 1). ##Evidence-Data-START## Transcript exon combination :: AB209207.1, M31774.1 [ECO:0000332] RNAseq introns :: single sample supports all introns ERS025084, ERS025088 [ECO:0000348] ##Evidence-Data-END## |
| ZFP14 | intronic | 57677 | zinc finger protein 14 homolog | N/A |
| ZNF843 | exonic | 283933 | zinc finger protein 843 | N/A |

FIG. 3 (CONTINUED)

| RefSeq_Gene_Symbol | Exon_overlap | RefSeq_Accession Number | mRNA_Description | SEQ ID |
|---|---|---|---|---|
| TGFBR3 | intronic | NM_001195683 | Homo sapiens transforming growth factor, beta receptor III (TGFBR3), transcript variant 2, mRNA. | 48 |
| TGFBR3 | intronic | NM_003243 | Homo sapiens transforming growth factor, beta receptor III (TGFBR3), transcript variant 1, mRNA. | 49 |
| TGFBR3 | intronic | NR_036634 | Homo sapiens transforming growth factor, beta receptor III (TGFBR3), transcript variant 4, non-coding RNA. | 50 |
| TGFBR3 | intronic | NM_001195684 | Homo sapiens transforming growth factor, beta receptor III (TGFBR3), transcript variant 3, mRNA. | 51 |
| HMGB3 | both | NM_005342 | Homo sapiens high mobility group box 3 (HMGB3), mRNA. | 52 |
| FUT9 | intronic | NM_006581 | Homo sapiens fucosyltransferase 9 (alpha (1,3) fucosyltransferase) (FUT9), mRNA. | 53 |
| PDE1C | intronic | NM_001191057 | Homo sapiens phosphodiesterase 1C, calmodulin-dependent 70kDa (PDE1C), transcript variant 2, mRNA. | 54 |
| PDE1C | intronic | NM_001191059 | Homo sapiens phosphodiesterase 1C, calmodulin-dependent 70kDa (PDE1C), transcript variant 5, mRNA. | 55 |
| PDE1C | intronic | NM_001191058 | Homo sapiens phosphodiesterase 1C, calmodulin-dependent 70kDa (PDE1C), transcript variant 3, mRNA. | 56 |

FIG. 4

| RefSeq_Gene_Symbol | Exon_overlap | RefSeq_Accession Number | mRNA_Description | SEQ ID |
|---|---|---|---|---|
| PDE1C | intronic | NM_001191056 | Homo sapiens phosphodiesterase 1C, calmodulin-dependent 70kDa (PDE1C), transcript variant 1, mRNA. | 57 |
| PDE1C | intronic | NM_005020 | Homo sapiens phosphodiesterase 1C, calmodulin-dependent 70kDa (PDE1C), transcript variant 4, mRNA. | 58 |
| IPMK | exonic | NM_152230 | Homo sapiens inositol polyphosphate multikinase (IPMK), mRNA. | 59 |
| GIGYF2 | intronic | NM_001103146 | Homo sapiens GRB10 interacting GYF protein 2 (GIGYF2), transcript variant 3, mRNA. | 60 |
| GIGYF2 | intronic | NM_001103147 | Homo sapiens GRB10 interacting GYF protein 2 (GIGYF2), transcript variant 1, mRNA. | 61 |
| GIGYF2 | intronic | NM_001103148 | Homo sapiens GRB10 interacting GYF protein 2 (GIGYF2), transcript variant 4, mRNA. | 62 |
| GIGYF2 | intronic | NM_015575 | Homo sapiens GRB10 interacting GYF protein 2 (GIGYF2), transcript variant 2, mRNA. | 63 |
| ACCS | exonic | NM_001127219 | Homo sapiens 1-aminocyclopropane-1-carboxylate synthase homolog (Arabidopsis)(non-functional) (ACCS), transcript variant 2, mRNA. | 64 |
| ACCS | exonic | NM_032592 | Homo sapiens 1-aminocyclopropane-1-carboxylate synthase homolog (Arabidopsis)(non-functional) (ACCS), transcript variant 1, mRNA. | 65 |
| DPP6 | intronic | NM_001039350 | Homo sapiens dipeptidyl-peptidase 6 (DPP6), transcript variant 3, mRNA. | 66 |

FIG. 4 (CONTINUED)

| RefSeq_Gene_Symbol | Exon_overlap | RefSeq_Accession Number | mRNA_Description | SEQ ID |
|---|---|---|---|---|
| DPP6 | intronic | NM_130797 | Homo sapiens dipeptidyl-peptidase 6 (DPP6), transcript variant 1, mRNA. | 67 |
| DPP6 | intronic | NM_001936 | Homo sapiens dipeptidyl-peptidase 6 (DPP6), transcript variant 2, mRNA. | 68 |
| ZNF843 | exonic | NM_001136509 | Homo sapiens zinc finger protein 843 (ZNF843), mRNA. | 69 |
| ARMC5 | exonic | NM_001105247 | Homo sapiens armadillo repeat containing 5 (ARMC5), transcript variant 1, mRNA. | 70 |
| ARMC5 | exonic | NM_024742 | Homo sapiens armadillo repeat containing 5 (ARMC5), transcript variant 2, mRNA. | 71 |
| TGFB1I1 | exonic | NM_001042454 | Homo sapiens transforming growth factor beta 1 induced transcript 1 (TGFB1I1), transcript variant 1, mRNA. | 72 |
| TGFB1I1 | exonic | NM_001164719 | Homo sapiens transforming growth factor beta 1 induced transcript 1 (TGFB1I1), transcript variant 3, mRNA. | 73 |
| TGFB1I1 | exonic | NM_015927 | Homo sapiens transforming growth factor beta 1 induced transcript 1 (TGFB1I1), transcript variant 2, mRNA. | 74 |
| SLC5A2 | exonic | NM_003041 | Homo sapiens solute carrier family 5 (sodium/glucose cotransporter), member 2 (SLC5A2), mRNA. | 75 |
| C16orf58 | exonic | NM_022744 | Homo sapiens chromosome 16 open reading frame 58 (C16orf58), mRNA. | 76 |
| PTK2 | intronic | NM_001199649 | Homo sapiens protein tyrosine kinase 2 (PTK2), transcript variant 3, mRNA. | 77 |

FIG. 4 (CONTINUED)

| RefSeq_Gene_Symbol | exon overlap | RefSeq_Accession Number | mRNA_Description | SEQ ID |
|---|---|---|---|---|
| PTK2 | exonic | NM_005607 | Homo sapiens protein tyrosine kinase 2 (PTK2), transcript variant 2, mRNA. | 78 |
| PTK2 | intronic | NM_153831 | Homo sapiens protein tyrosine kinase 2 (PTK2), transcript variant 1, mRNA. | 79 |
| LARP1B | exonic | NM_032239 | Homo sapiens La ribonucleoprotein domain family, member 1B (LARP1B), transcript variant 3, mRNA. | 80 |
| LARP1B | exonic | NM_178043 | Homo sapiens La ribonucleoprotein domain family, member 1B (LARP1B), transcript variant 2, mRNA. | 81 |
| LARP1B | exonic | NM_018078 | Homo sapiens La ribonucleoprotein domain family, member 1B (LARP1B), transcript variant 1, mRNA. | 82 |
| PGRMC2 | exonic | NM_006320 | Homo sapiens progesterone receptor membrane component 2 (PGRMC2), mRNA. | 83 |
| ZFP14 | intronic | NM_020917 | Homo sapiens ZFP14 zinc finger protein (ZFP14), mRNA. | 84 |
| DNAJC6 | exonic | NM_001258865 | Homo sapiens DnaJ (Hsp40) homolog, subfamily C, member 6 (DNAJC6), transcript variant 3, mRNA. | 85 |
| DNAJC6 | exonic | NM_014787 | Homo sapiens DnaJ (Hsp40) homolog, subfamily C, member 6 (DNAJC6), transcript variant 2, mRNA. | 86 |
| DNAJC6 | exonic | NM_001256864 | Homo sapiens DnaJ (Hsp40) homolog, subfamily C, member 6 (DNAJC6), transcript variant 1, mRNA. | 87 |

FIG. 4 (CONTINUED)

| RefSeq_Gene_Symbol | Exon_overlap | RefSeq_Accession Number | mRNA_Description | SEQ ID |
|---|---|---|---|---|
| LEPROT | exonic | NM_001198683 | Homo sapiens leptin receptor overlapping transcript (LEPROT), transcript variant 3, mRNA. | 88 |
| LEPROT | exonic | NM_017526 | Homo sapiens leptin receptor overlapping transcript (LEPROT), transcript variant 1, mRNA. | 89 |
| LEPR | exonic | NM_001003680 | Homo sapiens leptin receptor (LEPR), transcript variant 2, mRNA. | 90 |
| LEPR | exonic | NM_001003679 | Homo sapiens leptin receptor (LEPR), transcript variant 3, mRNA. | 91 |
| LEPR | exonic | NM_002303 | Homo sapiens leptin receptor (LEPR), transcript variant 1, mRNA. | 92 |
| LEPROT | exonic | NM_001198681 | Homo sapiens leptin receptor overlapping transcript (LEPROT), transcript variant 2, mRNA. | 93 |
| LEPR | intronic | NM_001198688 | Homo sapiens leptin receptor (LEPR), transcript variant 5, mRNA. | 94 |
| LEPR | intronic | NM_001198687 | Homo sapiens leptin receptor (LEPR), transcript variant 4, mRNA. | 95 |
| LEPR | intronic | NM_001198689 | Homo sapiens leptin receptor (LEPR), transcript variant 6, mRNA. | 96 |
| MUC4 | exonic | NM_004532 | Homo sapiens mucin 4, cell surface associated (MUC4), transcript variant 4, mRNA. | 97 |
| MUC4 | exonic | NM_018406 | Homo sapiens mucin 4, cell surface associated (MUC4), transcript variant 1, mRNA. | 98 |
| MUC4 | exonic | NM_138297 | Homo sapiens mucin 4, cell surface associated (MUC4), transcript variant 5, mRNA. | 99 |
| MAGEA11 | exonic | NM_005366 | Homo sapiens melanoma antigen family A, 11 (MAGEA11), transcript variant 1, mRNA. | 100 |

FIG. 4 (CONTINUED)

| RefSeq_Gene_Symbol | Exon_overlap | RefSeq_Accession Number | mRNA_Description | SEQ ID |
|---|---|---|---|---|
| MAGEA11 | exonic | NM_001011544 | Homo sapiens melanoma antigen family A, 11 (MAGEA11), transcript variant 2, mRNA. | 101 |
| BOK-AS1 | exonic | NR_033346 | Homo sapiens BOK antisense RNA 1 (BOK-AS1), antisense RNA. | 102 |
| BOK | exonic | NM_032515 | Homo sapiens BCL2-related ovarian killer (BOK), mRNA. | 103 |
| TSHR | exonic | NM_001018036 | Homo sapiens thyroid stimulating hormone receptor (TSHR), transcript variant 2, mRNA. | 104 |
| TSHR | exonic | NM_001142626 | Homo sapiens thyroid stimulating hormone receptor (TSHR), transcript variant 3, mRNA. | 105 |
| TSHR | exonic | NM_000369 | Homo sapiens thyroid stimulating hormone receptor (TSHR), transcript variant 1, mRNA. | 106 |
| MSN | exonic | NM_002444 | Homo sapiens moesin (MSN), mRNA. | 107 |
| MYADML | exonic | NR_003143 | Homo sapiens myeloid-associated differentiation marker-like (pseudogene) (MYADML), non-coding RNA. | 108 |
| CYP17A1 | exonic | NM_000102 | Homo sapiens cytochrome P450, family 17, subfamily A, polypeptide 1 (CYP17A1), mRNA. | 109 |
| C10orf32 | exonic | NM_001136200 | Homo sapiens chromosome 10 open reading frame 32 (C10orf32), transcript variant 1, mRNA. | 110 |
| C10orf32 | exonic | NM_144591 | Homo sapiens chromosome 10 open reading frame 32 (C10orf32), transcript variant 2, mRNA. | 111 |
| C10orf32-AS3MT | exonic | NR_037644 | Homo sapiens C10orf32-AS3MT readthrough (C10orf32-AS3MT), non-coding RNA. | 112 |

FIG. 4 (CONTINUED)

| RefSeq_Gene_Symbol | Exon_overlap | RefSeq_Accession Number | mRNA_Description | SEQ ID |
|---|---|---|---|---|
| AS3MT | exonic | NM_020682 | Homo sapiens arsenic (+3 oxidation state) methyltransferase (AS3MT), mRNA. | 113 |
| CNNM2 | exonic | NM_199077 | Homo sapiens cyclin M2 (CNNM2), transcript variant 3, mRNA. | 114 |
| CNNM2 | exonic | NM_017649 | Homo sapiens cyclin M2 (CNNM2), transcript variant 1, mRNA. | 115 |
| CNNM2 | exonic | NM_199076 | Homo sapiens cyclin M2 (CNNM2), transcript variant 2, mRNA. | 116 |
| RXFP1 | intronic | NR_045584 | Homo sapiens relaxin/insulin-like family peptide receptor 1 (RXFP1), transcript variant 13, non-coding RNA. | 117 |
| RXFP1 | intronic | NM_001253727 | Homo sapiens relaxin/insulin-like family peptide receptor 1 (RXFP1), transcript variant 2, mRNA. | 118 |
| RXFP1 | intronic | NM_001253728 | Homo sapiens relaxin/insulin-like family peptide receptor 1 (RXFP1), transcript variant 3, mRNA. | 119 |
| RXFP1 | intronic | NM_001253729 | Homo sapiens relaxin/insulin-like family peptide receptor 1 (RXFP1), transcript variant 4, mRNA. | 120 |
| RXFP1 | intronic | NM_001253730 | Homo sapiens relaxin/insulin-like family peptide receptor 1 (RXFP1), transcript variant 5, mRNA. | 121 |
| RXFP1 | intronic | NM_001253732 | Homo sapiens relaxin/insulin-like family peptide receptor 1 (RXFP1), transcript variant 6, mRNA. | 122 |

| RefSeq_Gene_Symbol | Exon_overlap | RefSeq_Accession_Number | mRNA_Description | SEQ ID |
|---|---|---|---|---|
| RXFP1 | intronic | NM_001253733 | Homo sapiens relaxin/insulin-like family peptide receptor 1 (RXFP1), transcript variant 7, mRNA. | 123 |
| RXFP1 | intronic | NM_021634 | Homo sapiens relaxin/insulin-like family peptide receptor 1 (RXFP1), transcript variant 1, mRNA. | 124 |
| RXFP1 | intronic | NR_045579 | Homo sapiens relaxin/insulin-like family peptide receptor 1 (RXFP1), transcript variant 8, non-coding RNA. | 125 |
| RXFP1 | intronic | NR_045580 | Homo sapiens relaxin/insulin-like family peptide receptor 1 (RXFP1), transcript variant 9, non-coding RNA. | 126 |
| RXFP1 | intronic | NR_045581 | Homo sapiens relaxin/insulin-like family peptide receptor 1 (RXFP1), transcript variant 10, non-coding RNA. | 127 |
| RXFP1 | intronic | NR_045582 | Homo sapiens relaxin/insulin-like family peptide receptor 1 (RXFP1), transcript variant 11, non-coding RNA. | 128 |
| RXFP1 | intronic | NR_045583 | Homo sapiens relaxin/insulin-like family peptide receptor 1 (RXFP1), transcript variant 12, non-coding RNA. | 129 |
| CRHR2 | exonic | NM_001202482 | Homo sapiens corticotropin releasing hormone receptor 2 (CRHR2), transcript variant 4, mRNA. | 130 |
| CRHR2 | exonic | NM_001202483 | Homo sapiens corticotropin releasing hormone receptor 2 (CRHR2), transcript variant 5, mRNA. | 131 |
| CRHR2 | exonic | NM_001883 | Homo sapiens corticotropin releasing hormone receptor 2 (CRHR2), transcript variant 1, mRNA. | 132 |

| RefSeq_Gene_Symbol | Exon_overlap | RefSeq_Accession Number | mRNA_Description | SEQ ID |
|---|---|---|---|---|
| CRHR2 | exonic | NM_001202475 | Homo sapiens corticotropin releasing hormone receptor 2 (CRHR2), transcript variant 2, mRNA. | 133 |
| CRHR2 | exonic | NM_001202481 | Homo sapiens corticotropin releasing hormone receptor 2 (CRHR2), transcript variant 3, mRNA. | 134 |
| PLA2G4C | exonic | NM_001159322 | Homo sapiens phospholipase A2, group IVC (cytosolic, calcium-independent) (PLA2G4C), transcript variant 2, mRNA. | 135 |
| PLA2G4C | exonic | NM_001159323 | Homo sapiens phospholipase A2, group IVC (cytosolic, calcium-independent) (PLA2G4C), transcript variant 3, mRNA. | 136 |
| PLA2G4C | exonic | NM_003706 | Homo sapiens phospholipase A2, group IVC (cytosolic, calcium-independent) (PLA2G4C), transcript variant 1, mRNA. | 137 |
| NCOA1 | exonic | NM_003743 | Homo sapiens nuclear receptor coactivator 1 (NCOA1), transcript variant 1, mRNA. | 138 |
| NCOA1 | exonic | NM_147223 | Homo sapiens nuclear receptor coactivator 1 (NCOA1), transcript variant 2, mRNA. | 139 |
| NCOA1 | exonic | NM_147233 | Homo sapiens nuclear receptor coactivator 1 (NCOA1), transcript variant 3, mRNA. | 140 |
| RAB19 | exonic | NM_001008749 | Homo sapiens RAB19, member RAS oncogene family (RAB19), mRNA. | 141 |
| MKRN1 | exonic | NM_013446 | Homo sapiens makorin ring finger protein 1 (MKRN1), transcript variant 1, mRNA. | 142 |
| MKRN1 | exonic | NM_001145125 | Homo sapiens makorin ring finger protein 1 (MKRN1), transcript variant 2, mRNA. | 143 |
| BNC2 | exonic | NM_017637 | Homo sapiens basonuclin 2 (BNC2), mRNA. | 144 |

FIG. 4 (CONTINUED)

| RefSeq_Gene_Symbol | Exon_overlap | RefSeq_Accession_Number | mRNA_Description | SEQ ID |
|---|---|---|---|---|
| NBPF1 | exonic | NM_017940 | Homo sapiens neuroblastoma breakpoint family, member 1 (NBPF1), mRNA. | 145 |
| MYO1B | both | NM_001130158 | Homo sapiens myosin IB (MYO1B), transcript variant 1, mRNA. | 146 |
| MYO1B | both | NM_012223 | Homo sapiens myosin IB (MYO1B), transcript variant 2, mRNA. | 147 |
| MYO1B | both | NM_001161819 | Homo sapiens myosin IB (MYO1B), transcript variant 3, mRNA. | 148 |
| GPR111 | exonic | NM_153839 | Homo sapiens G protein-coupled receptor 111 (GPR111), mRNA. | 149 |

FIG. 4 (CONTINUED)

| Category | Gene | Latest Phase | Competition |
|---|---|---|---|
| Novel | AADAT | Preclinical | 1 |
| Novel | ABCA4 | Phase II Clinical Trial | 1 |
| Novel | ABCC1 | Preclinical | 1 |
| Novel | ABCD1 | Phase II Clinical Trial | 1 |
| Novel | ACACB | Preclinical | 1 |
| Proven | ACE | Launched | 5+ |
| Novel | ACE2 | Phase II Clinical Trial | 2 |
| Proven | ACHE | Launched | 5+ |
| Novel | ACLY | Phase II Clinical Trial | 1 |
| Proven | ACPP | Launched | 1 |
| Novel | ACVR2A | Phase II Clinical Trial | 1 |
| Novel | ACVR2B | Preclinical | 2 |
| Novel | ACVRL1 | Phase II Clinical Trial | 3 |
| Proven | ADA | Launched | 5+ |
| Novel | ADAM15 | Phase II Clinical Trial | 1 |
| Novel | ADAM17 | Preclinical | 1 |
| Novel | ADAM8 | Preclinical | 1 |
| Novel | ADAMTS13 | Preclinical | 1 |
| Novel | ADM | Preclinical | 1 |
| Novel | ADNP | Preclinical | 1 |
| Proven | ADORA1 | Launched | 5+ |
| Proven | ADORA2A | Launched | 5+ |
| Novel | ADORA2B | Preclinical | 2 |
| Novel | ADORA3 | Phase III Clinical Trial | 5+ |
| Proven | ADRA1A | Launched | 5+ |
| Proven | ADRA2A | Launched | 5+ |
| Proven | ADRB1 | Launched | 5+ |
| Proven | ADRB2 | Launched | 5+ |
| Proven | ADRB3 | Launched | 5+ |
| Novel | AFP | Preclinical | 1 |
| Novel | AGER | Phase II Clinical Trial | 3 |
| Novel | AGRN | Preclinical | 1 |
| Novel | AGT | Preclinical | 3 |
| Proven | AGTR1 | Launched | 5+ |
| Novel | AGTR2 | Phase II Clinical Trial | 2 |
| Novel | AHR | Preclinical | 1 |
| Novel | AIFM1 | Phase II Clinical Trial | 1 |
| Proven | AKR1B1 | Launched | 3 |
| Novel | AKR1C3 | Preclinical | 1 |
| Novel | AKT1 | Phase II Clinical Trial | 5+ |
| Novel | AKT2 | Phase I Clinical Trial | 2 |
| Novel | ALAS1 | Preclinical | 1 |
| Novel | ALDH1A1 | Preclinical | 1 |
| Novel | ALDH2 | Phase II Clinical Trial | 2 |
| Proven | ALK | Launched | 5+ |
| Proven | ALOX5 | Launched | 4 |
| Novel | ALOX5AP | Phase II Clinical Trial | 2 |
| Novel | ALPL | Phase III Clinical Trial | 1 |

FIG. 10

| | | | |
|---|---|---|---|
| Novel | ALS3 | Phase I Clinical Trial | 1 |
| Novel | AMHR2 | Preclinical | 1 |
| Novel | ANGPT1 | Preclinical | 2 |
| Novel | ANGPT2 | Phase II Clinical Trial | 5+ |
| Novel | ANPEP | Phase III Clinical Trial | 1 |
| Novel | ANXA5 | Preclinical | 2 |
| Novel | AOC3 | Phase I Clinical Trial | 5+ |
| Novel | APCS | Phase II Clinical Trial | 3 |
| Novel | APEX1 | Phase I Clinical Trial | 1 |
| Novel | APOA1 | Phase II Clinical Trial | 5+ |
| Novel | APOA4 | Preclinical | 1 |
| Novel | APOB | Phase III Clinical Trial | 4 |
| Novel | APOC3 | Phase II Clinical Trial | 2 |
| Novel | APOE | Preclinical | 1 |
| Proven | APP | Launched | 5+ |
| Proven | AR | Launched | 5+ |
| Novel | ARG1 | Phase II Clinical Trial | 1 |
| Novel | ARSA | Phase II Clinical Trial | 2 |
| Proven | ARSB | Launched | 1 |
| Novel | ASIC1 | Phase I Clinical Trial | 1 |
| Novel | ASIC3 | Preclinical | 1 |
| Novel | ATOH1 | Preclinical | 1 |
| Proven | ATP1A1 | Launched | 5+ |
| Novel | ATP2A2 | Phase II Clinical Trial | 3 |
| Proven | ATP4A | Launched | 5+ |
| Novel | ATR | Preclinical | 2 |
| Novel | AURKA | Phase III Clinical Trial | 4 |
| Novel | AURKB | Phase II Clinical Trial | 2 |
| Proven | AVPR2 | Launched | 5+ |
| Novel | AXL | Preclinical | 5+ |
| Novel | BACE1 | Phase III Clinical Trial | 5+ |
| Novel | BAGE | Preclinical | 1 |
| Proven | BBOX1 | Launched | 1 |
| Novel | BCL2 | Phase II Clinical Trial | 5+ |
| Novel | BCL2L1 | Preclinical | 1 |
| Novel | BDKRB1 | Phase I Clinical Trial | 5+ |
| Proven | BDKRB2 | Launched | 4 |
| Novel | BGN | Preclinical | 1 |
| Novel | BIRC3 | Phase I Clinical Trial | 1 |
| Novel | BIRC5 | Phase II Clinical Trial | 4 |
| Novel | BMP1 | Preclinical | 1 |
| Proven | BMP2 | Launched | 4 |
| Proven | BMP7 | Launched | 1 |
| Novel | BPI | Phase I Clinical Trial | 1 |
| Proven | BRAF | Launched | 5+ |
| Novel | BRD4 | Phase II Clinical Trial | 1 |
| Novel | BST2 | Preclinical | 2 |
| Novel | BTK | Phase III Clinical Trial | 5+ |
| Novel | C3 | Phase II Clinical Trial | 4 |
| Proven | C5 | Launched | 3 |

FIG. 10 (CONTINUED)

| | | | |
|---|---|---|---|
| Novel | C5AR1 | Phase II Clinical Trial | 5+ |
| Proven | CA2 | Launched | 5+ |
| Novel | CA9 | Phase III Clinical Trial | 5+ |
| Proven | CACNA1B | Launched | 5+ |
| Proven | CACNA1C | Launched | 5+ |
| Proven | CACNA1G | Launched | 4 |
| Proven | CACNA2D1 | Launched | 5+ |
| Novel | CACNB3 | Preclinical | 1 |
| Proven | CALCA | Launched | 3 |
| Proven | CALCR | Launched | 5+ |
| Novel | CALCRL | Phase II Clinical Trial | 3 |
| Novel | CAPRIN1 | Preclinical | 1 |
| Novel | CASP1 | Preclinical | 1 |
| Novel | CASP2 | Phase I Clinical Trial | 2 |
| Novel | CASP3 | Phase II Clinical Trial | 2 |
| Novel | CASP6 | Preclinical | 2 |
| Novel | CASP8 | Phase II Clinical Trial | 2 |
| Novel | CASP9 | Phase I Clinical Trial | 2 |
| Proven | CASR | Launched | 5+ |
| Novel | CBLB | Preclinical | 2 |
| Proven | CCKAR | Launched | 1 |
| Proven | CCKBR | Launched | 3 |
| Novel | CCL11 | Phase II Clinical Trial | 1 |
| Novel | CCL2 | Phase II Clinical Trial | 1 |
| Proven | CCNG1 | Launched | 1 |
| Novel | CCR1 | Phase II Clinical Trial | 3 |
| Novel | CCR2 | Phase II Clinical Trial | 5+ |
| Novel | CCR3 | Phase II Clinical Trial | 2 |
| Proven | CCR4 | Launched | 5+ |
| Proven | CCR5 | Launched | 5+ |
| Novel | CCR6 | Preclinical | 1 |
| Novel | CCR9 | Phase III Clinical Trial | 2 |
| Novel | CD163 | Preclinical | 1 |
| Novel | CD19 | Phase II Clinical Trial | 5+ |
| Novel | CD200 | Phase II Clinical Trial | 3 |
| Novel | CD209 | Preclinical | 1 |
| Novel | CD22 | Phase III Clinical Trial | 5+ |
| Novel | CD248 | Phase II Clinical Trial | 1 |
| Novel | CD27 | Phase I Clinical Trial | 3 |
| Novel | CD274 | Phase I Clinical Trial | 3 |
| Novel | CD276 | Phase I Clinical Trial | 2 |
| Novel | CD28 | Phase II Clinical Trial | 3 |
| Proven | CD33 | Launched | 5+ |
| Novel | CD36 | Preclinical | 2 |
| Novel | CD37 | Phase II Clinical Trial | 2 |
| Novel | CD38 | Phase II Clinical Trial | 5+ |
| Novel | CD3E | Phase III Clinical Trial | 3 |
| Novel | CD4 | Phase II Clinical Trial | 5+ |
| Novel | CD40 | Phase II Clinical Trial | 5+ |
| Novel | CD40LG | Phase I Clinical Trial | 2 |

FIG. 10 (CONTINUED)

| | | | |
|---|---|---|---|
| Proven | CD44 | Launched | 5+ |
| Novel | CD47 | Preclinical | 1 |
| Novel | CD52 | Phase III Clinical Trial | 3 |
| Novel | CD55 | Phase II Clinical Trial | 2 |
| Novel | CD6 | Phase III Clinical Trial | 1 |
| Novel | CD70 | Phase I Clinical Trial | 4 |
| Novel | CD74 | Phase II Clinical Trial | 3 |
| Novel | CD79B | Phase II Clinical Trial | 1 |
| Novel | CD83 | Preclinical | 1 |
| Novel | CD8A | Preclinical | 1 |
| Novel | CDC7 | Preclinical | 4 |
| Novel | CDH11 | Preclinical | 1 |
| Novel | CDH5 | Phase III Clinical Trial | 1 |
| Novel | CDK4 | Phase I Clinical Trial | 2 |
| Novel | CDK5 | Preclinical | 1 |
| Novel | CDK7 | Preclinical | 1 |
| Novel | CDK9 | Preclinical | 2 |
| Novel | CDKN1A | Preclinical | 1 |
| Novel | CDKN1B | Preclinical | 1 |
| Novel | CDKN2A | Phase II Clinical Trial | 1 |
| Novel | CDNF | Preclinical | 1 |
| Novel | CEACAM1 | Preclinical | 1 |
| Proven | CEACAM5 | Launched | 5+ |
| Novel | CEL | Phase III Clinical Trial | 1 |
| Novel | CELA1 | Phase II Clinical Trial | 1 |
| Novel | CENPE | Phase I Clinical Trial | 1 |
| Novel | CETP | Phase III Clinical Trial | 5+ |
| Novel | CFB | Phase I Clinical Trial | 1 |
| Novel | CFD | Phase II Clinical Trial | 1 |
| Novel | CFH | Preclinical | 1 |
| Proven | CFTR | Launched | 5+ |
| Novel | CGB | Phase I Clinical Trial | 1 |
| Novel | CHAT | Phase II Clinical Trial | 2 |
| Novel | CHEK1 | Phase II Clinical Trial | 5+ |
| Novel | CHEK2 | Preclinical | 2 |
| Novel | CHKA | Phase I Clinical Trial | 3 |
| Proven | CHRM1 | Launched | 5+ |
| Proven | CHRM3 | Launched | 5+ |
| Novel | CHRNA7 | Phase III Clinical Trial | 5+ |
| Proven | CLCA1 | Launched | 1 |
| Proven | CLCN2 | Launched | 3 |
| Novel | CLU | Phase III Clinical Trial | 3 |
| Novel | CMA1 | Phase II Clinical Trial | 1 |
| Novel | CNGB3 | Preclinical | 1 |
| Proven | CNR1 | Launched | 5+ |
| Novel | CNTFR | Phase III Clinical Trial | 1 |
| Proven | COL18A1 | Launched | 4 |
| Novel | COL2A1 | Preclinical | 1 |
| Proven | COMT | Launched | 5+ |
| Novel | CPB2 | Phase I Clinical Trial | 3 |

FIG. 10 (CONTINUED)

| | | | |
|---|---|---|---|
| Proven | CPS1 | Launched | 1 |
| Novel | CPT1A | Phase I Clinical Trial | 4 |
| Novel | CR1 | Phase I Clinical Trial | 1 |
| Proven | CRAT | Launched | 1 |
| Novel | CRP | Phase II Clinical Trial | 2 |
| Proven | CSF1 | Launched | 4 |
| Novel | CSF1R | Phase I Clinical Trial | 5+ |
| Novel | CSF2 | Phase III Clinical Trial | 5+ |
| Proven | CSF2RA | Launched | 5+ |
| Proven | CSF3 | Launched | 5+ |
| Proven | CSF3R | Launched | 5+ |
| Novel | CSNK1D | Preclinical | 1 |
| Novel | CSNK2A1 | Preclinical | 1 |
| Novel | CSNK2B | Phase III Clinical Trial | 1 |
| Novel | CSPG4 | Preclinical | 2 |
| Novel | CTAG1B | Phase I Clinical Trial | 5+ |
| Novel | CTF1 | Phase I Clinical Trial | 1 |
| Novel | CTGF | Phase II Clinical Trial | 3 |
| Proven | CTLA4 | Launched | 3 |
| Novel | CTNNB1 | Phase II Clinical Trial | 1 |
| Novel | CTSC | Preclinical | 1 |
| Novel | CTSK | Phase III Clinical Trial | 3 |
| Novel | CTSS | Preclinical | 4 |
| Proven | CUBN | Launched | 2 |
| Novel | CXCL10 | Phase II Clinical Trial | 3 |
| Novel | CXCL12 | Phase II Clinical Trial | 2 |
| Novel | CXCL13 | Preclinical | 1 |
| Novel | CXCR2 | Phase I Clinical Trial | 1 |
| Proven | CXCR4 | Launched | 5+ |
| Novel | CXCR5 | Phase I Clinical Trial | 1 |
| Novel | CXCR6 | Preclinical | 1 |
| Novel | CXCR7 | Preclinical | 1 |
| Novel | CYBB | Preclinical | 1 |
| Novel | CYP11B2 | Phase II Clinical Trial | 3 |
| Proven | CYP17A1 | Launched | 5+ |
| Proven | CYP19A1 | Launched | 5+ |
| Novel | CYP24A1 | Preclinical | 1 |
| Novel | CYP2B6 | Phase II Clinical Trial | 1 |
| Novel | CYP51A1 | Preclinical | 1 |
| Proven | CYSLTR1 | Launched | 5+ |
| Novel | DAO | Preclinical | 2 |
| Novel | DCLRE1C | Preclinical | 1 |
| Novel | DCPS | Phase I Clinical Trial | 1 |
| Novel | DCT | Phase II Clinical Trial | 2 |
| Proven | DDC | Launched | 5+ |
| Novel | DDIT4 | Phase II Clinical Trial | 1 |
| Novel | DDX5 | Preclinical | 1 |
| Novel | DGAT1 | Phase III Clinical Trial | 5+ |
| Novel | DGAT2 | Preclinical | 1 |
| Proven | DHFR | Launched | 4 |

FIG. 10 (CONTINUED)

| | | | |
|---|---|---|---|
| Proven | DHODH | Launched | 4 |
| Novel | DIABLO | Phase II Clinical Trial | 1 |
| Novel | DKK1 | Phase II Clinical Trial | 3 |
| Novel | DKK2 | Preclinical | 1 |
| Novel | DLL4 | Phase I Clinical Trial | 4 |
| Novel | DMD | Phase III Clinical Trial | 5+ |
| Novel | DMPK | Preclinical | 1 |
| Proven | DNASE1 | Launched | 1 |
| Proven | DNMT1 | Launched | 5+ |
| Novel | DOT1L | Phase I Clinical Trial | 1 |
| Proven | DPP4 | Launched | 5+ |
| Novel | DPYD | Phase II Clinical Trial | 1 |
| Proven | DRD1 | Launched | 2 |
| Proven | DRD2 | Launched | 5+ |
| Proven | DRD3 | Launched | 5+ |
| Novel | DUT | Preclinical | 1 |
| Novel | DYRK1A | Preclinical | 2 |
| Novel | DYSF | Preclinical | 1 |
| Novel | EDA | Phase I Clinical Trial | 1 |
| Proven | EDNRA | Launched | 3 |
| Novel | EEF1A1 | Preclinical | 1 |
| Proven | EGF | Launched | 1 |
| Novel | EGFL7 | Phase II Clinical Trial | 1 |
| Proven | EGFR | Launched | 5+ |
| Novel | EGLN2 | Phase II Clinical Trial | 5+ |
| Novel | EGR1 | Phase II Clinical Trial | 1 |
| Novel | EIF4E | Phase II Clinical Trial | 1 |
| Novel | EIF5A | Phase II Clinical Trial | 1 |
| Proven | ELANE | Launched | 5+ |
| Novel | ELN | Preclinical | 1 |
| Novel | ENG | Phase II Clinical Trial | 1 |
| Novel | ENPEP | Phase I Clinical Trial | 1 |
| Novel | EPHA3 | Phase I Clinical Trial | 1 |
| Novel | EPHX2 | Phase I Clinical Trial | 1 |
| Novel | EPO | Preclinical | 2 |
| Proven | EPOR | Launched | 5+ |
| Proven | ERBB2 | Launched | 5+ |
| Novel | ERBB3 | Phase II Clinical Trial | 5+ |
| Novel | ERN1 | Preclinical | 1 |
| Novel | ERVW-1 | Phase II Clinical Trial | 2 |
| Proven | ESR1 | Launched | 5+ |
| Novel | ESRRA | Preclinical | 4 |
| Novel | EXOG | Phase II Clinical Trial | 1 |
| Novel | EZH2 | Preclinical | 4 |
| Proven | F10 | Launched | 5+ |
| Novel | F11 | Phase II Clinical Trial | 5+ |
| Proven | F13A1 | Launched | 3 |
| Proven | F2 | Launched | 5+ |
| Novel | F2RL1 | Preclinical | 2 |
| Novel | F3 | Phase II Clinical Trial | 5+ |

FIG. 10 (CONTINUED)

| | | | |
|---|---|---|---|
| Proven | F7 | Launched | 5+ |
| Proven | F8 | Launched | 5+ |
| Proven | F9 | Launched | 5+ |
| Novel | FAAH | Phase I Clinical Trial | 5+ |
| Novel | FAP | Preclinical | 2 |
| Novel | FAS | Phase II Clinical Trial | 3 |
| Novel | FASLG | Phase II Clinical Trial | 2 |
| Novel | FASN | Preclinical | 1 |
| Novel | FCAR | Preclinical | 1 |
| Novel | FCER2 | Preclinical | 1 |
| Novel | FCGR2B | Phase II Clinical Trial | 3 |
| Novel | FCGRT | Preclinical | 1 |
| Novel | FCRL5 | Preclinical | 1 |
| Novel | FDFT1 | Preclinical | 1 |
| Novel | FFAR1 | Phase III Clinical Trial | 5+ |
| Novel | FFAR2 | Phase I Clinical Trial | 2 |
| Novel | FFAR4 | Phase III Clinical Trial | 2 |
| Novel | FGF18 | Phase II Clinical Trial | 1 |
| Novel | FGF2 | Phase II Clinical Trial | 3 |
| Novel | FGF21 | Preclinical | 3 |
| Novel | FGF23 | Phase II Clinical Trial | 1 |
| Novel | FGF4 | Phase III Clinical Trial | 1 |
| Proven | FGFR1 | Launched | 5+ |
| Proven | FGFR2 | Launched | 3 |
| Novel | FIGF | Phase II Clinical Trial | 4 |
| Proven | FKBP1A | Launched | 5+ |
| Novel | FN1 | Phase II Clinical Trial | 1 |
| Proven | FNTA | Launched | 5+ |
| Proven | FOLH1 | Launched | 5+ |
| Novel | FOLR1 | Phase III Clinical Trial | 5+ |
| Novel | FOXA1 | Preclinical | 1 |
| Novel | FOXP3 | Preclinical | 1 |
| Novel | FPR2 | Preclinical | 1 |
| Novel | FRMD4A | Preclinical | 1 |
| Proven | FSHR | Launched | 5+ |
| Novel | FZD7 | Phase I Clinical Trial | 1 |
| Proven | GAA | Launched | 5+ |
| Proven | GABBR1 | Launched | 5+ |
| Proven | GABRA1 | Launched | 5+ |
| Novel | GAD1 | Preclinical | 1 |
| Novel | GALNS | Phase III Clinical Trial | 1 |
| Novel | GALR1 | Preclinical | 1 |
| Novel | GALR3 | Phase II Clinical Trial | 1 |
| Novel | GAPDH | Phase I Clinical Trial | 1 |
| Proven | GAST | Launched | 5+ |
| Novel | GATA3 | Phase II Clinical Trial | 2 |
| Proven | GBA | Launched | 5+ |
| Novel | GCG | Phase III Clinical Trial | 5+ |
| Proven | GCGR | Launched | 5+ |
| Novel | GCK | Phase II Clinical Trial | 5+ |

FIG. 10 (CONTINUED)

| | | | |
|---|---|---|---|
| Novel | GDE1 | Preclinical | 1 |
| Novel | GDF5 | Phase II Clinical Trial | 2 |
| Novel | GDNF | Preclinical | 5+ |
| Novel | GFRA1 | Preclinical | 2 |
| Novel | GFRA3 | Phase I Clinical Trial | 1 |
| Proven | GHR | Launched | 5+ |
| Novel | GHRH | Phase I Clinical Trial | 1 |
| Proven | GHRHR | Launched | 5+ |
| Novel | GHSR | Phase III Clinical Trial | 5+ |
| Proven | GLA | Launched | 5+ |
| Proven | GLP1R | Launched | 5+ |
| Proven | GLP2R | Launched | 3 |
| Novel | GNRH1 | Preclinical | 1 |
| Proven | GNRHR | Launched | 5+ |
| Novel | GP1BA | Phase II Clinical Trial | 1 |
| Novel | GP6 | Phase II Clinical Trial | 4 |
| Novel | GPBAR1 | Preclinical | 5+ |
| Novel | GPC3 | Phase II Clinical Trial | 2 |
| Novel | GPNMB | Phase II Clinical Trial | 1 |
| Novel | GPR119 | Phase II Clinical Trial | 5+ |
| Novel | GPR142 | Preclinical | 1 |
| Novel | GPR39 | Preclinical | 1 |
| Novel | GPR55 | Preclinical | 1 |
| Novel | GRB2 | Phase I Clinical Trial | 1 |
| Proven | GRIA1 | Launched | 5+ |
| Proven | GRIN1 | Launched | 5+ |
| Novel | GRIN2A | Preclinical | 1 |
| Novel | GRIN2B | Phase II Clinical Trial | 5+ |
| Novel | GRIN2D | Preclinical | 1 |
| Novel | GRM1 | Preclinical | 1 |
| Novel | GRM2 | Phase II Clinical Trial | 5+ |
| Novel | GRM3 | Preclinical | 2 |
| Novel | GRM4 | Preclinical | 5+ |
| Novel | GRM5 | Phase III Clinical Trial | 5+ |
| Novel | GRM7 | Preclinical | 1 |
| Novel | GRPR | Phase I Clinical Trial | 1 |
| Novel | GSG2 | Preclinical | 1 |
| Novel | GSK3B | Phase II Clinical Trial | 5+ |
| Novel | GSTP1 | Phase II Clinical Trial | 1 |
| Proven | GUCY2C | Launched | 5+ |
| Proven | GUSB | Launched | 2 |
| Novel | GZMB | Preclinical | 4 |
| Novel | HAMP | Phase II Clinical Trial | 3 |
| Novel | HAO2 | Preclinical | 1 |
| Novel | HAVCR1 | Preclinical | 1 |
| Novel | HBB | Phase II Clinical Trial | 2 |
| Novel | HBEGF | Phase I Clinical Trial | 2 |
| Proven | HCAR2 | Launched | 4 |
| Novel | HCRTR1 | Preclinical | 1 |
| Novel | HDAC10 | Phase II Clinical Trial | 1 |

FIG. 10 (CONTINUED)

| | | | |
|---|---|---|---|
| Novel | HDAC3 | Phase I Clinical Trial | 1 |
| Novel | HDAC4 | Preclinical | 1 |
| Novel | HDAC6 | Phase II Clinical Trial | 4 |
| Novel | HDAC8 | Preclinical | 1 |
| Novel | HDC | Phase II Clinical Trial | 1 |
| Novel | HDGFRP3 | Preclinical | 1 |
| Novel | HGF | Phase III Clinical Trial | 5+ |
| Novel | HIF1A | Phase I Clinical Trial | 5+ |
| Novel | HIST1H1D | Phase II Clinical Trial | 1 |
| Novel | HLA-B | Phase III Clinical Trial | 1 |
| Novel | HMBS | Phase I Clinical Trial | 1 |
| Novel | HMGB1 | Preclinical | 4 |
| Proven | HMGCR | Launched | 5+ |
| Novel | HMOX1 | Preclinical | 1 |
| Proven | HPD | Launched | 1 |
| Proven | HPGD | Launched | 1 |
| Proven | HPRT1 | Launched | 1 |
| Novel | HPSE | Phase III Clinical Trial | 3 |
| Novel | HRAS | Preclinical | 1 |
| Proven | HRH1 | Launched | 5+ |
| Proven | HRH2 | Launched | 5+ |
| Novel | HRH3 | Phase III Clinical Trial | 5+ |
| Novel | HRH4 | Phase II Clinical Trial | 5+ |
| Novel | HSD11B1 | Phase II Clinical Trial | 5+ |
| Novel | HSD17B3 | Preclinical | 1 |
| Novel | HSP90AA1 | Phase II Clinical Trial | 5+ |
| Novel | HSP90B1 | Preclinical | 1 |
| Novel | HSPA5 | Phase II Clinical Trial | 2 |
| Novel | HSPB1 | Phase II Clinical Trial | 3 |
| Novel | HSPD1 | Phase III Clinical Trial | 1 |
| Novel | HSPE1 | Phase I Clinical Trial | 1 |
| Proven | HTR1A | Launched | 5+ |
| Proven | HTR1D | Launched | 5+ |
| Proven | HTR2A | Launched | 5+ |
| Proven | HTR3A | Launched | 5+ |
| Proven | HTR4 | Launched | 5+ |
| Novel | HTT | Preclinical | 3 |
| Proven | HYAL1 | Launched | 3 |
| Novel | IAPP | Preclinical | 4 |
| Novel | ICAM1 | Phase III Clinical Trial | 2 |
| Novel | ICMT | Preclinical | 1 |
| Novel | ICOS | Phase I Clinical Trial | 1 |
| Novel | ICOSLG | Phase I Clinical Trial | 1 |
| Novel | IDH1 | Preclinical | 1 |
| Novel | IDH2 | Preclinical | 1 |
| Novel | IDO1 | Phase II Clinical Trial | 4 |
| Proven | IDS | Launched | 3 |
| Proven | IDUA | Launched | 2 |
| Novel | IFNA1 | Phase II Clinical Trial | 2 |
| Novel | IFNA2 | Phase II Clinical Trial | 4 |

FIG. 10 (CONTINUED)

| | | | |
|---|---|---|---|
| Proven | IFNAR1 | Launched | 5+ |
| Proven | IFNAR2 | Launched | 5+ |
| Novel | IFNB1 | Preclinical | 2 |
| Proven | IFNG | Launched | 4 |
| Proven | IFNGR1 | Launched | 5+ |
| Novel | IFNLR1 | Phase III Clinical Trial | 2 |
| Novel | IGF1 | Phase II Clinical Trial | 3 |
| Proven | IGF1R | Launched | 5+ |
| Novel | IGF2R | Phase II Clinical Trial | 1 |
| Novel | IGFBP3 | Phase II Clinical Trial | 1 |
| Proven | IGHE | Launched | 5+ |
| Novel | IKBKB | Phase II Clinical Trial | 2 |
| Novel | IL10 | Preclinical | 2 |
| Novel | IL10RA | Phase II Clinical Trial | 3 |
| Proven | IL11RA | Launched | 5+ |
| Novel | IL12A | Preclinical | 1 |
| Proven | IL12B | Launched | 4 |
| Novel | IL12RB1 | Phase II Clinical Trial | 1 |
| Novel | IL13 | Phase III Clinical Trial | 5+ |
| Novel | IL13RA2 | Phase II Clinical Trial | 1 |
| Novel | IL15RA | Preclinical | 3 |
| Novel | IL17A | Phase III Clinical Trial | 5+ |
| Novel | IL17RA | Phase III Clinical Trial | 1 |
| Novel | IL17RB | Preclinical | 1 |
| Novel | IL18 | Phase II Clinical Trial | 2 |
| Novel | IL1A | Phase III Clinical Trial | 1 |
| Proven | IL1B | Launched | 5+ |
| Proven | IL1R1 | Launched | 1 |
| Novel | IL1RAP | Preclinical | 1 |
| Proven | IL1RN | Launched | 2 |
| Proven | IL2 | Launched | 2 |
| Novel | IL20 | Phase II Clinical Trial | 2 |
| Novel | IL21R | Phase II Clinical Trial | 2 |
| Novel | IL22RA1 | Phase I Clinical Trial | 2 |
| Novel | IL23A | Phase III Clinical Trial | 4 |
| Novel | IL27 | Phase III Clinical Trial | 1 |
| Proven | IL2RA | Launched | 5+ |
| Novel | IL31 | Phase I Clinical Trial | 1 |
| Novel | IL3RA | Phase II Clinical Trial | 4 |
| Novel | IL4R | Preclinical | 1 |
| Novel | IL5 | Phase III Clinical Trial | 2 |
| Novel | IL5RA | Phase II Clinical Trial | 1 |
| Novel | IL6 | Phase III Clinical Trial | 5+ |
| Proven | IL6R | Launched | 5+ |
| Novel | IL7R | Phase II Clinical Trial | 3 |
| Proven | IL8 | Launched | 3 |
| Novel | ILK | Preclinical | 1 |
| Proven | IMPDH1 | Launched | 5+ |
| Novel | INPP5D | Phase II Clinical Trial | 4 |
| Novel | INS | Phase I Clinical Trial | 3 |

FIG. 10 (CONTINUED)

| | | | |
|---|---|---|---|
| Proven | INSR | Launched | 5+ |
| Novel | IRAK1 | Preclinical | 1 |
| Novel | IRAK4 | Preclinical | 2 |
| Novel | IRS1 | Phase III Clinical Trial | 1 |
| Novel | ITGA1 | Phase I Clinical Trial | 1 |
| Novel | ITGA2 | Phase II Clinical Trial | 1 |
| Novel | ITGAL | Phase II Clinical Trial | 2 |
| Novel | ITGB1BP2 | Preclinical | 1 |
| Novel | ITK | Phase I Clinical Trial | 1 |
| Novel | JAG1 | Preclinical | 1 |
| Novel | KCNA5 | Phase I Clinical Trial | 3 |
| Proven | KCNH2 | Launched | 1 |
| Proven | KCNMA1 | Launched | 2 |
| Novel | KCNN4 | Preclinical | 1 |
| Novel | KDM1A | Preclinical | 4 |
| Novel | KHK | Preclinical | 1 |
| Novel | KIF11 | Phase II Clinical Trial | 5+ |
| Novel | KIR3DL2 | Preclinical | 1 |
| Proven | KIT | Launched | 5+ |
| Novel | KLK1 | Preclinical | 1 |
| Novel | KLRC1 | Phase I Clinical Trial | 1 |
| Novel | KMO | Preclinical | 1 |
| Proven | KRAS | Launched | 3 |
| Novel | KSR1 | Preclinical | 1 |
| Novel | LAG3 | Phase II Clinical Trial | 3 |
| Novel | LCAT | Phase I Clinical Trial | 1 |
| Novel | LDLR | Preclinical | 1 |
| Novel | LEP | Preclinical | 1 |
| Novel | LEPR | Phase III Clinical Trial | 5+ |
| Novel | LGALS1 | Phase I Clinical Trial | 1 |
| Novel | LGALS3 | Phase III Clinical Trial | 4 |
| Proven | LHCGR | Launched | 5+ |
| Novel | LILRA4 | Preclinical | 1 |
| Novel | LIMK2 | Phase II Clinical Trial | 1 |
| Novel | LINGO1 | Phase II Clinical Trial | 1 |
| Novel | LIPA | Phase III Clinical Trial | 1 |
| Novel | LNPEP | Preclinical | 1 |
| Novel | LOXL2 | Phase II Clinical Trial | 1 |
| Novel | LPA | Preclinical | 1 |
| Novel | LPAR1 | Phase II Clinical Trial | 2 |
| Proven | LPL | Launched | 5+ |
| Novel | LRP1 | Preclinical | 1 |
| Novel | LRRK2 | Preclinical | 3 |
| Novel | LTA | Phase II Clinical Trial | 2 |
| Novel | LTA4H | Phase I Clinical Trial | 2 |
| Novel | LTBR | Preclinical | 1 |
| Novel | LTC4S | Preclinical | 1 |
| Novel | LTF | Phase II Clinical Trial | 2 |
| Novel | LY75 | Phase I Clinical Trial | 1 |
| Novel | MADCAM1 | Phase II Clinical Trial | 1 |

FIG. 10 (CONTINUED)

| | | | |
|---|---|---|---|
| Novel | MAG | Phase II Clinical Trial | 1 |
| Novel | MAGEA3 | Phase III Clinical Trial | 3 |
| Novel | MALAT1 | Preclinical | 1 |
| Novel | MAN2B1 | Phase III Clinical Trial | 1 |
| Novel | MANF | Preclinical | 1 |
| Proven | MAOA | Launched | 3 |
| Proven | MAOB | Launched | 5+ |
| Novel | MAP3K5 | Preclinical | 1 |
| Novel | MAPK8 | Preclinical | 1 |
| Novel | MAPK8IP1 | Phase II Clinical Trial | 1 |
| Novel | MAPKAPK2 | Preclinical | 1 |
| Novel | MAPT | Phase III Clinical Trial | 5+ |
| Novel | MARCKS | Phase II Clinical Trial | 1 |
| Novel | MAS1 | Phase II Clinical Trial | 3 |
| Novel | MASP2 | Preclinical | 1 |
| Proven | MBP | Launched | 3 |
| Novel | MC1R | Phase III Clinical Trial | 3 |
| Proven | MC2R | Launched | 1 |
| Novel | MC4R | Phase II Clinical Trial | 2 |
| Novel | MC5R | Phase II Clinical Trial | 1 |
| Novel | MCAM | Preclinical | 1 |
| Novel | MCHR1 | Preclinical | 1 |
| Novel | MCL1 | Preclinical | 2 |
| Novel | MDK | Preclinical | 2 |
| Novel | MDM2 | Phase I Clinical Trial | 5+ |
| Novel | MELK | Preclinical | 1 |
| Novel | METAP2 | Phase II Clinical Trial | 3 |
| Novel | MGEA5 | Preclinical | 1 |
| Novel | MGMT | Phase I Clinical Trial | 2 |
| Novel | MIA | Preclinical | 2 |
| Novel | MIEN1 | Preclinical | 1 |
| Novel | MIR10B | Preclinical | 1 |
| Novel | MIR122 | Phase II Clinical Trial | 2 |
| Novel | MIR145 | Preclinical | 1 |
| Novel | MIR195 | Preclinical | 1 |
| Novel | MIR206 | Preclinical | 1 |
| Novel | MIR21 | Preclinical | 1 |
| Novel | MIR29A | Preclinical | 1 |
| Novel | MIR33A | Preclinical | 1 |
| Novel | MIR34A | Preclinical | 1 |
| Novel | MIR378A | Preclinical | 1 |
| Novel | MIR451A | Preclinical | 1 |
| Novel | MIRLET7A1 | Preclinical | 1 |
| Novel | MLANA | Phase II Clinical Trial | 1 |
| Novel | MLNR | Phase II Clinical Trial | 4 |
| Proven | MME | Launched | 1 |
| Proven | MMP1 | Launched | 1 |
| Novel | MMP12 | Phase I Clinical Trial | 1 |
| Novel | MMP13 | Preclinical | 1 |
| Novel | MMP14 | Preclinical | 1 |

FIG. 10 (CONTINUED)

| | | | |
|---|---|---|---|
| Novel | MMP2 | Preclinical | 1 |
| Proven | MMP8 | Launched | 2 |
| Novel | MMP9 | Preclinical | 2 |
| Proven | MPL | Launched | 5+ |
| Novel | MPO | Phase II Clinical Trial | 3 |
| Novel | MRGPRD | Preclinical | 1 |
| Proven | MS4A1 | Launched | 5+ |
| Novel | MSLN | Phase II Clinical Trial | 3 |
| Novel | MSTN | Phase II Clinical Trial | 5+ |
| Novel | MTF1 | Phase I Clinical Trial | 2 |
| Proven | MTOR | Launched | 5+ |
| Proven | MTTP | Launched | 2 |
| Proven | MUC1 | Launched | 5+ |
| Novel | MUC16 | Phase III Clinical Trial | 1 |
| Novel | MYB | Preclinical | 1 |
| Novel | MYC | Preclinical | 2 |
| Novel | MYLIP | Preclinical | 1 |
| Novel | MYO7A | Phase II Clinical Trial | 1 |
| Novel | NAGLU | Preclinical | 3 |
| Novel | NAMPT | Preclinical | 1 |
| Novel | NCAM1 | Phase II Clinical Trial | 2 |
| Novel | NCL | Phase II Clinical Trial | 5+ |
| Novel | NCR1 | Preclinical | 2 |
| Novel | ND2 | Preclinical | 1 |
| Novel | NEDD4 | Preclinical | 1 |
| Proven | NFE2L2 | Launched | 3 |
| Proven | NFKB1 | Launched | 5+ |
| Novel | NFKBIA | Preclinical | 1 |
| Novel | NGF | Phase II Clinical Trial | 5+ |
| Novel | NGFR | Phase II Clinical Trial | 3 |
| Proven | NISCH | Launched | 2 |
| Novel | NLN | Preclinical | 1 |
| Novel | NOS1 | Phase II Clinical Trial | 3 |
| Novel | NOS2 | Phase II Clinical Trial | 2 |
| Novel | NOS3 | Phase II Clinical Trial | 1 |
| Novel | NOTCH1 | Phase I Clinical Trial | 4 |
| Proven | NPC1L1 | Launched | 3 |
| Proven | NPR1 | Launched | 5+ |
| Novel | NPY2R | Phase I Clinical Trial | 2 |
| Novel | NPY5R | Phase II Clinical Trial | 3 |
| Novel | NR1H2 | Preclinical | 1 |
| Novel | NR1H4 | Phase III Clinical Trial | 3 |
| Proven | NR3C1 | Launched | 5+ |
| Proven | NR3C2 | Launched | 5+ |
| Novel | NR4A2 | Preclinical | 1 |
| Novel | NR5A1 | Preclinical | 1 |
| Novel | NRG1 | Phase III Clinical Trial | 2 |
| Novel | NRP1 | Phase I Clinical Trial | 2 |
| Novel | NRTN | Phase II Clinical Trial | 1 |
| Novel | NTN1 | Preclinical | 1 |

FIG. 10 (CONTINUED)

| | | | |
|---|---|---|---|
| Novel | NTRK1 | Phase II Clinical Trial | 5+ |
| Novel | NTRK2 | Preclinical | 1 |
| Proven | ODC1 | Launched | 2 |
| Novel | OGFR | Preclinical | 1 |
| Proven | OPRK1 | Launched | 5+ |
| Novel | OPRL1 | Phase II Clinical Trial | 5+ |
| Proven | OPRM1 | Launched | 5+ |
| Proven | OXTR | Launched | 5+ |
| Novel | P2RX3 | Phase II Clinical Trial | 4 |
| Novel | P2RX7 | Phase I Clinical Trial | 5+ |
| Novel | P2RY1 | Preclinical | 1 |
| Proven | P2RY12 | Launched | 5+ |
| Proven | P2RY2 | Launched | 2 |
| Novel | P4HA1 | Phase II Clinical Trial | 2 |
| Novel | PABPN1 | Preclinical | 1 |
| Novel | PAK1 | Preclinical | 1 |
| Novel | PAK4 | Preclinical | 1 |
| Novel | PARK2 | Preclinical | 1 |
| Novel | PARP1 | Phase III Clinical Trial | 5+ |
| Novel | PASD1 | Preclinical | 1 |
| Novel | PAX2 | Preclinical | 2 |
| Novel | PCNA | Preclinical | 1 |
| Novel | PCSK6 | Preclinical | 1 |
| Novel | PCSK9 | Phase III Clinical Trial | 5+ |
| Novel | PDCD1 | Phase III Clinical Trial | 5+ |
| Proven | PDE1A | Launched | 1 |
| Novel | PDE2A | Preclinical | 1 |
| Proven | PDE3A | Launched | 5+ |
| Proven | PDE4A | Launched | 5+ |
| Proven | PDE5A | Launched | 5+ |
| Novel | PDE8B | Preclinical | 1 |
| Proven | PDGFRB | Launched | 5+ |
| Novel | PDHA1 | Phase II Clinical Trial | 1 |
| Novel | PDPK1 | Phase I Clinical Trial | 1 |
| Novel | PDX1 | Preclinical | 1 |
| Novel | PDYN | Phase II Clinical Trial | 1 |
| Novel | PECAM1 | Preclinical | 1 |
| Novel | PFKFB3 | Preclinical | 2 |
| Proven | PGR | Launched | 5+ |
| Novel | PHB | Phase I Clinical Trial | 1 |
| Novel | PI3 | Phase II Clinical Trial | 2 |
| Novel | PIK3C3 | Preclinical | 1 |
| Novel | PIK3CA | Phase III Clinical Trial | 5+ |
| Novel | PIK3CB | Phase II Clinical Trial | 2 |
| Novel | PIK3CD | Phase I Clinical Trial | 5+ |
| Novel | PIK3CG | Preclinical | 4 |
| Novel | PIKFYVE | Preclinical | 1 |
| Novel | PION | Preclinical | 1 |
| Novel | PKM | Preclinical | 4 |
| Novel | PKN3 | Phase I Clinical Trial | 1 |

FIG. 10 (CONTINUED)

| | | | |
|---|---|---|---|
| Novel | PLA2G10 | Preclinical | 1 |
| Novel | PLA2G4A | Phase I Clinical Trial | 1 |
| Novel | PLA2G7 | Phase III Clinical Trial | 4 |
| Proven | PLAT | Launched | 5+ |
| Proven | PLAU | Launched | 5+ |
| Novel | PLAUR | Preclinical | 2 |
| Proven | PLG | Launched | 5+ |
| Novel | PLK1 | Phase III Clinical Trial | 5+ |
| Novel | PLK2 | Preclinical | 2 |
| Novel | PMEL | Phase I Clinical Trial | 1 |
| Proven | PNLIP | Launched | 5+ |
| Novel | PNP | Phase II Clinical Trial | 2 |
| Novel | PORCN | Phase I Clinical Trial | 1 |
| Proven | PPARA | Launched | 5+ |
| Novel | PPARD | Phase I Clinical Trial | 2 |
| Proven | PPARG | Launched | 5+ |
| Proven | PPIA | Launched | 5+ |
| Novel | PPIB | Phase II Clinical Trial | 1 |
| Novel | PPID | Preclinical | 1 |
| Novel | PPP2CA | Phase I Clinical Trial | 2 |
| Novel | PPYR1 | Preclinical | 2 |
| Novel | PRAME | Phase II Clinical Trial | 1 |
| Novel | PRCP | Preclinical | 1 |
| Novel | PREP | Phase II Clinical Trial | 1 |
| Novel | PRKCA | Preclinical | 4 |
| Novel | PRKCB | Phase III Clinical Trial | 1 |
| Proven | PRKCD | Launched | 1 |
| Novel | PRKCQ | Preclinical | 1 |
| Novel | PRKDC | Phase I Clinical Trial | 1 |
| Novel | PRLR | Phase I Clinical Trial | 2 |
| Novel | PRMT5 | Preclinical | 1 |
| Novel | PRNP | Preclinical | 2 |
| Proven | PROC | Launched | 4 |
| Novel | PROM1 | Preclinical | 2 |
| Novel | PRSS12 | Preclinical | 1 |
| Novel | PRTN3 | Phase III Clinical Trial | 1 |
| Novel | PSCA | Preclinical | 2 |
| Proven | PTAFR | Launched | 5+ |
| Novel | PTCH1 | Preclinical | 1 |
| Novel | PTGDR | Phase III Clinical Trial | 2 |
| Novel | PTGDR2 | Phase II Clinical Trial | 5+ |
| Novel | PTGDS | Phase II Clinical Trial | 2 |
| Proven | PTGER1 | Launched | 5+ |
| Proven | PTGER2 | Launched | 5+ |
| Novel | PTGER4 | Phase II Clinical Trial | 5+ |
| Proven | PTGES | Launched | 5+ |
| Proven | PTGFR | Launched | 5+ |
| Proven | PTGIR | Launched | 5+ |
| Proven | PTGS1 | Launched | 5+ |
| Proven | PTGS2 | Launched | 5+ |

FIG. 10 (CONTINUED)

| | | | |
|---|---|---|---|
| Proven | PTH | Launched | 4 |
| Proven | PTH1R | Launched | 5+ |
| Novel | PTK2 | Phase II Clinical Trial | 5+ |
| Proven | PTMA | Launched | 2 |
| Novel | PTPRC | Phase II Clinical Trial | 2 |
| Novel | PVRL4 | Phase I Clinical Trial | 1 |
| Novel | PYGL | Preclinical | 4 |
| Novel | QPCT | Phase I Clinical Trial | 2 |
| Proven | RARB | Launched | 2 |
| Novel | RARRES3 | Preclinical | 2 |
| Novel | RASSF1 | Preclinical | 1 |
| Novel | RB1 | Phase I Clinical Trial | 1 |
| Novel | REG3A | Phase II Clinical Trial | 2 |
| Proven | REN | Launched | 5+ |
| Proven | RHD | Launched | 2 |
| Novel | RIPK2 | Preclinical | 1 |
| Novel | RLN1 | Phase I Clinical Trial | 1 |
| Novel | ROBO1 | Preclinical | 1 |
| Novel | ROCK1 | Phase III Clinical Trial | 2 |
| Novel | ROCK2 | Phase I Clinical Trial | 1 |
| Novel | RORA | Preclinical | 2 |
| Novel | RORC | Preclinical | 4 |
| Novel | RPE65 | Phase II Clinical Trial | 1 |
| Novel | RPS6KB1 | Preclinical | 2 |
| Novel | RTN4 | Phase II Clinical Trial | 3 |
| Novel | RUNX3 | Preclinical | 1 |
| Novel | RXFP1 | Phase III Clinical Trial | 5+ |
| Novel | RYR1 | Preclinical | 3 |
| Novel | RYR2 | Phase II Clinical Trial | 1 |
| Novel | S100A4 | Preclinical | 1 |
| Novel | S100A9 | Phase III Clinical Trial | 2 |
| Novel | SCD | Preclinical | 2 |
| Novel | SCGB1A1 | Phase II Clinical Trial | 1 |
| Novel | SCN10A | Phase I Clinical Trial | 3 |
| Proven | SCN5A | Launched | 5+ |
| Proven | SCN9A | Launched | 5+ |
| Proven | SCNN1A | Launched | 3 |
| Proven | SCTR | Launched | 4 |
| Novel | SDC1 | Phase II Clinical Trial | 1 |
| Novel | SELE | Preclinical | 1 |
| Novel | SELP | Phase II Clinical Trial | 2 |
| Novel | SELPLG | Phase I Clinical Trial | 2 |
| Novel | SEMA3A | Preclinical | 1 |
| Novel | SEMA4D | Phase I Clinical Trial | 1 |
| Proven | SERPINA1 | Launched | 5+ |
| Proven | SERPINC1 | Launched | 5+ |
| Novel | SERPINE1 | Preclinical | 1 |
| Novel | SERPINF1 | Preclinical | 1 |
| Proven | SERPING1 | Launched | 5+ |
| Novel | SGPL1 | Phase II Clinical Trial | 1 |

FIG. 10 (CONTINUED)

| | | | |
|---|---|---|---|
| Novel | SGSH | Phase II Clinical Trial | 2 |
| Proven | SI | Launched | 1 |
| Novel | SIGLEC15 | Preclinical | 1 |
| Novel | SIK2 | Preclinical | 1 |
| Novel | SIRPA | Preclinical | 1 |
| Novel | SIRT1 | Phase II Clinical Trial | 4 |
| Novel | SLAMF7 | Phase III Clinical Trial | 1 |
| Novel | SLC10A2 | Phase II Clinical Trial | 3 |
| Proven | SLC12A3 | Launched | 5+ |
| Novel | SLC16A1 | Preclinical | 1 |
| Proven | SLC18A2 | Launched | 5+ |
| Proven | SLC22A12 | Launched | 4 |
| Novel | SLC2A8 | Preclinical | 1 |
| Novel | SLC34A3 | Preclinical | 2 |
| Novel | SLC40A1 | Phase I Clinical Trial | 1 |
| Novel | SLC44A4 | Phase I Clinical Trial | 1 |
| Novel | SLC5A1 | Phase I Clinical Trial | 2 |
| Proven | SLC5A2 | Launched | 5+ |
| Novel | SLC5A5 | Preclinical | 1 |
| Proven | SLC6A1 | Launched | 1 |
| Proven | SLC6A2 | Launched | 5+ |
| Proven | SLC6A3 | Launched | 5+ |
| Proven | SLC6A4 | Launched | 5+ |
| Novel | SLC6A9 | Phase III Clinical Trial | 2 |
| Novel | SLC9A3 | Phase II Clinical Trial | 2 |
| Novel | SMN2 | Phase II Clinical Trial | 3 |
| Proven | SMO | Launched | 5+ |
| Novel | SMPD1 | Phase II Clinical Trial | 2 |
| Novel | SNCA | Phase I Clinical Trial | 5+ |
| Novel | SNRNP70 | Phase III Clinical Trial | 1 |
| Proven | SOAT1 | Launched | 1 |
| Novel | SOD1 | Phase III Clinical Trial | 5+ |
| Novel | SOST | Phase III Clinical Trial | 5+ |
| Novel | SPHK1 | Preclinical | 1 |
| Novel | SPHK2 | Phase I Clinical Trial | 2 |
| Proven | SRD5A2 | Launched | 1 |
| Novel | SREBF2 | Preclinical | 2 |
| Novel | ST13 | Preclinical | 1 |
| Novel | STAB1 | Preclinical | 2 |
| Novel | STAT3 | Phase II Clinical Trial | 5+ |
| Novel | STEAP1 | Phase I Clinical Trial | 1 |
| Novel | STMN1 | Phase I Clinical Trial | 1 |
| Novel | STS | Phase II Clinical Trial | 2 |
| Proven | SV2A | Launched | 2 |
| Novel | SYK | Phase II Clinical Trial | 5+ |
| Novel | SYVN1 | Preclinical | 1 |
| Novel | TAAR1 | Preclinical | 1 |
| Proven | TACR1 | Launched | 5+ |
| Novel | TACR2 | Phase II Clinical Trial | 3 |
| Novel | TACR3 | Preclinical | 1 |

FIG. 10 (CONTINUED)

| | | | |
|---|---|---|---|
| Novel | TACSTD2 | Preclinical | 3 |
| Novel | TAP1 | Phase I Clinical Trial | 2 |
| Novel | TARDBP | Preclinical | 2 |
| Proven | TBXA2R | Launched | 3 |
| Proven | TBXAS1 | Launched | 4 |
| Novel | TERC | Phase II Clinical Trial | 1 |
| Novel | TERT | Phase III Clinical Trial | 5+ |
| Novel | TFF1 | Preclinical | 1 |
| Novel | TFF3 | Preclinical | 1 |
| Proven | TFPI | Launched | 4 |
| Novel | TFRC | Preclinical | 1 |
| Proven | TGFB1 | Launched | 5+ |
| Novel | TGFB2 | Phase III Clinical Trial | 2 |
| Novel | TGFBR1 | Phase II Clinical Trial | 5+ |
| Novel | TGFBR2 | Phase I Clinical Trial | 1 |
| Novel | TGM2 | Preclinical | 3 |
| Proven | THBD | Launched | 2 |
| Novel | THRB | Phase I Clinical Trial | 2 |
| Novel | TIE1 | Preclinical | 1 |
| Novel | TLR2 | Phase II Clinical Trial | 1 |
| Novel | TLR3 | Phase III Clinical Trial | 5+ |
| Proven | TLR4 | Launched | 5+ |
| Novel | TLR5 | Phase I Clinical Trial | 1 |
| Novel | TLR7 | Phase II Clinical Trial | 5+ |
| Novel | TLR8 | Phase II Clinical Trial | 2 |
| Novel | TLR9 | Phase III Clinical Trial | 5+ |
| Novel | TMEFF2 | Preclinical | 1 |
| Novel | TMPRSS15 | Preclinical | 1 |
| Novel | TMPRSS6 | Preclinical | 1 |
| Novel | TMSB4X | Preclinical | 1 |
| Novel | TNC | Phase II Clinical Trial | 1 |
| Proven | TNF | Launched | 5+ |
| Novel | TNFRSF10A | Phase II Clinical Trial | 1 |
| Novel | TNFRSF10B | Phase II Clinical Trial | 2 |
| Novel | TNFRSF11B | Preclinical | 1 |
| Novel | TNFRSF12A | Phase II Clinical Trial | 5+ |
| Novel | TNFRSF13C | Phase I Clinical Trial | 1 |
| Novel | TNFRSF18 | Phase I Clinical Trial | 1 |
| Novel | TNFRSF4 | Phase II Clinical Trial | 2 |
| Proven | TNFRSF8 | Launched | 2 |
| Novel | TNFRSF9 | Phase II Clinical Trial | 2 |
| Novel | TNFSF10 | Preclinical | 5+ |
| Proven | TNFSF11 | Launched | 3 |
| Novel | TNFSF13 | Preclinical | 1 |
| Proven | TNFSF13B | Launched | 3 |
| Novel | TNFSF14 | Phase I Clinical Trial | 1 |
| Novel | TNFSF4 | Phase II Clinical Trial | 2 |
| Novel | TNFSF8 | Preclinical | 1 |
| Proven | TNNC1 | Launched | 1 |
| Proven | TOP1 | Launched | 5+ |

FIG. 10 (CONTINUED)

| | | | |
|---|---|---|---|
| Proven | TOP2A | Launched | 5+ |
| Novel | TOR1A | Preclinical | 1 |
| Proven | TP53 | Launched | 5+ |
| Novel | TPBG | Phase III Clinical Trial | 5+ |
| Novel | TPH1 | Phase III Clinical Trial | 2 |
| Proven | TPO | Launched | 1 |
| Novel | TPP1 | Preclinical | 1 |
| Novel | TPSAB1 | Preclinical | 1 |
| Novel | TRAF6 | Preclinical | 1 |
| Novel | TRBV6-2 | Phase II Clinical Trial | 1 |
| Novel | TREM1 | Preclinical | 1 |
| Proven | TRHR | Launched | 5+ |
| Novel | TRIM63 | Preclinical | 1 |
| Novel | TRPA1 | Phase II Clinical Trial | 4 |
| Novel | TRPC5 | Preclinical | 1 |
| Novel | TRPM7 | Preclinical | 1 |
| Novel | TRPM8 | Phase I Clinical Trial | 5+ |
| Proven | TRPV1 | Launched | 5+ |
| Novel | TRPV3 | Phase II Clinical Trial | 2 |
| Novel | TRPV4 | Preclinical | 3 |
| Novel | TRPV6 | Phase I Clinical Trial | 3 |
| Proven | TSHR | Launched | 1 |
| Novel | TSLP | Phase I Clinical Trial | 1 |
| Novel | TSPO | Phase I Clinical Trial | 2 |
| Novel | TTK | Preclinical | 1 |
| Proven | TTR | Launched | 4 |
| Proven | TUBB | Launched | 5+ |
| Novel | TUBB3 | Preclinical | 1 |
| Novel | TUSC2 | Phase I Clinical Trial | 1 |
| Novel | TXN | Phase II Clinical Trial | 2 |
| Novel | TYK2 | Preclinical | 2 |
| Novel | TYMP | Phase III Clinical Trial | 2 |
| Proven | TYMS | Launched | 5+ |
| Proven | TYR | Launched | 1 |
| Novel | UBA3 | Phase I Clinical Trial | 2 |
| Novel | UBE3A | Preclinical | 1 |
| Novel | UGCG | Phase III Clinical Trial | 3 |
| Novel | USP14 | Preclinical | 2 |
| Novel | USP19 | Preclinical | 1 |
| Novel | USP34 | Preclinical | 1 |
| Novel | USP7 | Preclinical | 2 |
| Novel | UTRN | Phase I Clinical Trial | 2 |
| Novel | UTS2R | Phase I Clinical Trial | 1 |
| Proven | VDR | Launched | 5+ |
| Proven | VEGFA | Launched | 5+ |
| Novel | VEGFB | Preclinical | 1 |
| Novel | VEGFC | Phase I Clinical Trial | 2 |
| Novel | VIM | Phase II Clinical Trial | 1 |
| Proven | VIPR1 | Launched | 4 |
| Novel | VKORC1 | Preclinical | 1 |

FIG. 10 (CONTINUED)

| | | | |
|---|---|---|---|
| Novel | VTCN1 | Preclinical | 1 |
| Proven | VWF | Launched | 5+ |
| Novel | WAS | Phase II Clinical Trial | 1 |
| Novel | WEE1 | Phase II Clinical Trial | 2 |
| Novel | WT1 | Phase II Clinical Trial | 5+ |
| Proven | XDH | Launched | 3 |
| Novel | XIAP | Phase II Clinical Trial | 2 |
| Novel | XPO1 | Phase II Clinical Trial | 5+ |
| Novel | YWHAH | Preclinical | 1 |
| Novel | ZP3 | Preclinical | 1 |
| Novel | ZYX | Preclinical | 1 |

FIG. 10 (CONTINUED)

| Location | Sample Description |
|---|---|
| A1 | Ladder |
| B1 | Heterozygous deletion carrier |
| C1 | Heterozygous deletion carrier |
| D1 | Heterozygous deletion carrier |
| E1 | Heterozygous deletion carrier |
| F1 | Heterozygous deletion carrier |
| G1 | Wild type – no deletion |

US 11,384,397 B2

METHODS AND COMPOSITIONS FOR DIAGNOSING, PROGNOSING, AND TREATING ENDOMETRIOSIS

CROSS-REFERENCE TO RELATED APPLICATIONS

This application claims the benefit of the filing date of U.S. application Ser. No. 61/903,286, filed on Nov. 12, 2013, the disclosure of which is incorporated by reference herein.

The instant application includes a file identified as follows: "3886001US1sequencelisting.txt", which is 22,601, 728 bytes in size. This file contains tabulated sequence information in non-delineated format. The aforementioned file was created on Nov. 3, 2014 and is hereby incorporated by reference in its entirely.

BACKGROUND

Endometriosis is an estrogen-dependent gynecologic disorder, defined as the presence of endometrial like tissue outside the uterine cavity, which affects 6% to 10% women of reproductive age from all ethnic and social groups. The degree of endometriosis is staged according to the classification system of the American Society of Reproductive Medicine (*Fertil. Steril.*, 67:81721 (1997)) into minimal, mild, moderate, and severe disease. At present, the gold standard for diagnosis of endometriosis is laparoscopic inspection with histologic confirmation after retrieval of lesions.

As endometriosis can be progressive in up to 50% of women, early noninvasive diagnosis has the potential to offer early treatment and prevent progression. A noninvasive test for endometriosis would be also useful for women with pelvic pain and/or subfertility with normal ultrasound results. The goal of a non-invasive test is that no women with endometriosis or other significant pelvic pathology are missed who might benefit from medical therapy or surgery. There are reports of biomarkers that maybe useful for early or noninvasive detection. For example, Fossbinder et al. (*Fertil. Steril.*, 99:1135-1145 (2013)) point out that cancer antigen 125 (CA-125) is the most used peripheral biomarker of endometriosis, and that out of 28 biomarkers, multivariate analysis of plasma samples, showed that annexin V, vascular endothelial growth factor (VEGF), CA-125, and soluble intercellular adhesion molecule-1 (sICAM-1)/or glycodelinin enabled the diagnosis of endometriosis in women who had disease undetected by ultrasound. Surprisingly, inflammatory molecules did not emerge as biomarkers in a panel with the best diagnostic performers.

May et al. (*Hum. Reprod. Update.* 17:637-53 (2011)) conducted a systematic review of published results that assessed over 200 potential biomarkers for endometriosis, including hormones and their receptors, cytokines, and factors identified using proteomics, and analyzed histological results from endometrial tissue. Some of those putative biomarkers related to nerve fiber growth or cell cycle control, while others were cytokines including IL-1β, IL-IR type II, IL-6, IL-8, IL-13, IL-15, tumor necrosis factor (TNF)-α, (MCP-1); macrophage-stimulating protein (RANTES); steroids and hormones, e.g., aromatase and hydroxysteroid dehydrogenase enzymes; growth factors; e.g., TGFβ family, insulin-like growth (IGF) factors, hepatocyte growth factor (HGF) and its receptor, annexin-1; cell adhesion and extracellular matrix molecules, e.g., the r33 integrin subunit $\alpha_3\beta_1$ integrin, $\alpha_v\beta_5$ and $\alpha_v\beta_5$ integrins, E-cadherin; extracellular matrix molecules (ECM), e.g., ICAM-1, focal adhesion kinase (FAK); tissue remodeling molecules, e.g., matrix metalloproteinase (MMP) family, tissue inhibitors of metalloproteinases (TIMPs), urokinase; angiogenesis, e.g., vascular endothelial growth factor (VEGF), angiopoeitin-1 and -2 molecules; associated with apoptosis and cell cycle control, e.g., calpain 5, MCL-1, Bak, Ki67, telomerase activity, proliferating cell nuclear antigen, Pak-1, phosphorylated ERK I 12, c-myc, survivin; reactive oxygen and nitrogen species, e.g., endothelial xanthine oxidase, WT-1, CCL16, CCL21, HOXA10 and COX-2.

SUMMARY OF THE INVENTION

The invention provides a method of screening one or more female subjects for those having endometriosis (EN), those with altered susceptibility to developing EN or those at risk of developing EN. The method comprises assaying at least one genetic sample of one or more subjects, nucleic acid sequence information from the one or more subjects, or providing that information, for at least one genetic variation in one or more loci associated with EN, e.g., gene variations associated with one or more genes in FIG. 3. The presence in the genetic sample of the at least one genetic variation is used to determine whether the one or more subjects have EN, have an altered susceptibility to EN or are at risk of EN. In some embodiments, determining whether the one or more subjects have EN, are at risk of EN or have an altered susceptibility to EN includes a gynecological examination and/or medical history analysis of the one or more subjects, e.g., in addition to the nucleic acid sequence information. In some embodiments, at least one genetic sample is collected from blood, e.g., peripheral blood mononuclear cells (PBMC) or peripheral blood lymphocytes (PBL), saliva, urine, serum, tears, skin, tissue, or hair from at least one subject. In some embodiments, assaying the at least one genetic sample of one or more subjects includes purifying the at least one genetic sample. In some embodiments, assaying the at least one genetic sample of the one or more subjects includes amplifying at least one nucleotide or a specific region of one or more chromosomes in the at least one genetic sample. In some embodiments, assaying the at least one genetic sample of the one or more subjects includes assaying an unamplified sample for at least one nucleotide or a specific region of one or more chromosomes in the at least one genetic sample. In some embodiments, assaying the at least one genetic sample for at least one genetic variation includes a microarray analysis of the at least one sample. In some embodiments, the microarray analysis comprises a comparative genomic hybridization (CGH) array analysis.

In one embodiment, the invention provides a method of diagnosing a susceptibility to endometriosis in a female subject. The method includes providing nucleic acid sequence information from the female subject on the presence or absence of at least genetic variation in one or more genes or regions in FIG. 1 or FIG. 2. A susceptibility to endometriosis in the subject is diagnosed if the subject has at least one genetic variation in the one or more genes or regions in FIG. 1, wherein the at least genetic variation occurs in the gene or region more frequently in a population of female subjects that have endometriosis than in a population of female subjects that does not have endometriosis. In one embodiment, the nucleic acid sequence information is for one or more genes or regions that include but are not limited to one or more of TGFBR3, FUT9, PDE1C, IMPK, GIGYF2, HMGB3, ZFP14, ACCS, or DPP6. In one embodiment, the nucleic acid sequence information is for one or more genes or regions that include but are not limited to one or more of MYO1B, MIR3675, NBPF1, or GPR111. In one embodiment, the nucleic acid sequence information is for one or more genes or regions that include but are not limited to one or more of TGFB1I1, PTK2, PGRMC2, LEPROT, LEPR, MUC4, MAGEA11, BOK, BOK-AS1, TSHR, MSN, MYADML, CYP17A1, RXFP1, CRHR2, PLA2G4C, NCOA1, BNC2, or MKRN1. In one embodiment, the nucleic acid sequence information is for one or more genes or regions that include but are not limited to one or more of ARMC5, C16orf58, SLC5A2, ZNF843, LARP1B, DNAJC6, AS3MT, C10orf32, AS3MT-C10orf32, CNNM2, or RAB19.

In one embodiment, the invention provides a method of diagnosing a susceptibility to endometriosis in a female subject. The method includes detecting in a sample of the subject nucleic acid sequence information on the presence or absence of at least one genetic variation in one or more regions in FIG. 2. A susceptibility to endometriosis is diagnosed in the subject if the subject has at least one genetic variation in the one or more genes or regions in FIG. 1 or FIG. 2, wherein the at least genetic variation occurs in the gene or region more frequently in a population of female subjects that have endometriosis than in a population of female subjects that does not have endometriosis. In one embodiment, the nucleic acid sequence information is for one or more genes or regions that include but are not limited to one or more of TGFBR3, FUT9, PDE1C, IMPK, GIGYF2, HMGB3, ZFP14, ACCS, or DPP6. In one embodiment, the nucleic acid sequence information is for one or more genes or regions that include but are not limited to one or more of MYO1B, MIR3675, NBPF1, or GPR111. In one embodiment, the nucleic acid sequence information is for one or more genes or regions that include but are not limited to one or more of TGFB1I1, PTK2, PGRMC2. LEPROT, LEPR, MUC4, MAGEA11, BOK, BOK-AS1, TSHR, MSN, MYADML, CYP17A1, RXFP1, CRHR2, PLA2G4C, NCOA1, BNC2, or MKRN1. In one embodiment, the nucleic acid sequence information is for one or more genes or regions that include but are not limited to one or more of ARMC5, C16orf58, SLC5A2, ZNF843, LARP1B, DNAJC6, AS3MT, C10orf32, AS3MT-C10orf32, CNNM2, or RAB19.

In one embodiment, the invention provides a method that includes providing nucleic acid sequence information from a female subject on the presence or absence of at least genetic variation in one or more genes or regions in FIG. 2. A susceptibility to endometriosis in the subject is diagnosed if the subject has at least one genetic variation in the one or more genes or regions in FIG. 2, wherein the at least genetic variation occurs in the gene or region more frequently in a population of female subjects that have endometriosis than in a population of female subjects that does not have endometriosis. In one embodiment, the nucleic acid sequence information is for one or more genes or regions that include but are not limited to one or more of TGFBR3, FUT9, PDE1C, IMPK, GIGYF2, HMGB3, ZFP14, ACCS, or DPP6. In one embodiment, the nucleic acid sequence information is for one or more genes or regions that include but are not limited to one or more of MYO1B, MIR3675, NBPF1, or GPR111. In one embodiment, the nucleic acid sequence information is for one or more genes or regions that include but are not limited to one or more of TGFB1I1, PTK2, PGRMC2, LEPROT, LEPR, MUC4, MAGEA11, BOK, BOK-AS1, TSHR, MSN, MYADML, CYP17A1, RXFP1, CRHR2, PLA2G4C, NCOA1, BNC2, or MKRN1. In one embodiment, the nucleic acid sequence information is for one or more genes or regions that include but are not limited to one or more of ARMC5, C16orf58, SLC5A2, ZNF843, LARP1B, DNAJC6, AS3MT, C10orf32, AS3MT-C10orf32, CNNM2, or RAB19.

In some embodiments, the method further comprises designing or preparing an array, e.g., a CGH array, to measure or detect one or more genetic variations in the regions shown in FIG. 1 or FIG. 2. In some embodiments, the method further comprises providing such a CGH array for the measuring or detecting of one or more genetic variations. In some embodiments, assaying at least one genetic sample comprises obtaining nucleic acid sequence information. In some embodiments, obtaining the nucleic acid sequence information is accomplished by one or more methods including but not limited to PCR, sequencing, Northern blots, multiplex ligation-dependent probe amplification (MLPA), molecular beacon, array. Comparative Genomic Hybridization, Invader assay, ligase chain reaction (LCR), fluorescence in situ hybridization, or any combination thereof. In some embodiments, sequencing comprises one or more high-throughput sequencing methods.

In some embodiments, determining whether one or more test subjects have EN, are at risk of EN or have an altered susceptibility to EN includes comparing the nucleic acid sequence information of the one or more test subjects, the at least one genetic variation identified in the one or more test subjects, or a combination thereof, to those of one or more control subjects, e.g., subjects that do not have EN, are not at risk of EN or do not have an enhanced susceptibility to EN. In some embodiments, the one more control subjects include one or more subjects not suspected of having EN and the one or more test subjects include one or more subjects suspected of having EN. In some embodiments, the one or more test subjects include one or more subjects with EN, and the one or more control subjects include one or more subjects without EN. In some embodiments, the one or more test subjects include one or more subjects who are symptomatic for EN, and the one or more control subjects include one or more subjects who are asymptomatic for EN. In some embodiments, the one or more test subjects include one or more subjects that do not present with pain as a major symptom. In some embodiments, the one or more test subjects have infertility issues (e.g., up to about 40% of women with EN have infertility issues but have no or little pain related to their EN lesions). In some embodiments, the one or more control subjects include one or more subjects that have increased or decreased susceptibility to EN. In some embodiments, the one or more control subjects include one or more subjects associated or unassociated with a treatment, therapeutic regimen, or any combination thereof.

In some embodiments, determining whether the one or more test subjects have EN, are at risk of EN or have an altered susceptibility to EN includes comparing a gynecological examination, a medical history analysis, or a combination thereof, of the one or more test subjects to the nucleic acid sequence information of the one or more test subjects, at least one genetic variation identified in the one or more test subjects, the nucleic acid sequence information of one or more control subjects, at least one genetic variation identified in the one or more control subjects, or a combination thereof.

In some embodiments, the at least one genetic variation comprises one or more point mutations, single nucleotide polymorphisms (SNPs), single nucleotide variants (SNVs), polymorphisms, translocations, insertions, deletions, amplifications, inversions, microsatellites, interstitial deletions, copy number variations (CNVs), loss of heterozygosity, or any combination thereof. For example, in some embodiments, the at least one genetic variation includes one or more genetic variations, e.g., CNVs in the genes listed in FIG. 1, e.g., genes having any one of SEQ ID NOs:1-47 or one or more genetic variations in CNV subregions listed in FIG. 2. In some embodiments, the genetic variation includes one or more genetic variations, e.g., CNVs, that disrupt or modulate one or more genes listed in FIG. 3. In some embodiments, the at least one genetic variation includes variations such as one or more CNVs that disrupt or modulate the expression or function of one or more RNA transcripts in FIG. 4, e.g., those having any one of SEQ ID NOs:48-149

In one aspect, the invention provides a method for screening for a therapeutic agent useful for preventing, inhibiting or treating EN. The method includes identifying an agent that modulates the function or expression of one or more genes listed in FIG. 3 or expression products therefrom, or one or more RNA transcripts mentioned in FIG. 4 or expression products thereof. In some embodiments, the expression products include one or more proteins expressed from a gene listed in FIG. 3 or encoded by one or more transcripts mentioned in FIG. 4. In some embodiments, modulating the function or activity of one or more RNA transcripts or proteins results in an increase in expression. In some embodiments, modulating the function or activity of one or more RNA transcripts or proteins results in a decrease in expression.

In one aspect, a method of preventing, inhibiting or treating EN in a subject is provided. The method includes administering one or more agents effective to modulate the function of one or more genes listed in FIG. 3, or expression products therefrom, or one or more RNA transcripts mentioned in FIG. 4, or expression products thereof, thereby preventing, inhibiting or treating the EN. In some embodiments, the expression products are one or more proteins expressed from a gene listed in FIG. 3, or encoded by one or more RNA transcripts mentioned in FIG. 4 or genes in the same pathway (see, e.g., FIG. 9). In some embodiments, the one or more agents include but are not limited to a protein, e.g., an antibody, a drug, a combination of drugs, a compound, a combination of compounds, radiation, a genetic sequence, a combination of genetic sequences, heat or cryogenics, or a combination of two or more of any combination thereof.

In one aspect, a method for screening for a therapeutic agent useful for treating EN is provided. The method includes identifying an agent that modulates the function or expression of one or more genes listed in FIG. 3 or expression products therefrom. In some embodiments, the expression products include one or more RNA transcripts in FIG. 4. In some embodiments, the expression products include one or more proteins expressed from a gene listed in FIG. 3 or encoded by one or more RNA transcripts in FIG. 4. In some embodiments, modulating the function or activity of one or more RNA transcripts or proteins includes an increase in expression. In some embodiments, modulating the function or activity of one or more RNA transcripts or proteins includes a decrease in expression. In some embodiments, screening the one or more subjects also includes selecting one or more therapies based on the presence or absence of the one or more genetic variations, e.g., the presence of a genetic variation in at least one gene listed in FIG. 3.

In one aspect, a method of treating a subject for EN is provided. The method includes administering one or more agents effective to modulate the function of one or more genes listed in FIG. 3, or expression products therefrom, thereby treating EN. In some embodiments, the expression products include one or more RNA transcripts in FIG. 4. In some embodiments, the expression products include one or more proteins expressed from a gene in FIG. 3, or encoded by one or more RNA transcripts in FIG. 4. In some embodiments, the agent may be an antibody, a compound, a combination of compounds, radiation, a genetic sequence, a combination of genetic sequences, heat, cryogenics, and a combination of two or more of any combination thereof.

As described in Examples 3 and 4, CNV analysis using methods described in Example 1 revealed the presence of a 4-probe spanning heterozygous TGFBR3 deletion in 3 individuals with endometriosis. Primer pairs specific for that region successfully generated a product of the expected size in the deletion carriers but not in either normal DNA or DNA from an endometriosis patient without the deletion. Thus, TGFBR3 genetic variations, e.g., the TGFBR3 CNV or others described herein, may be used in an assay that would facilitate rapid and low cost screening of endometriosis cohorts for the presence of the genetic variation, e.g., deletion, in order to obtain better estimates for the frequency of the variation in such cohorts and diagnose the cause of endometriosis in those who carry the variation.

The method comprises assaying at least one genetic sample of one or more subjects, nucleic acid sequence information from the one or more subjects, or providing that information, for at least one genetic variation impacting or encompassing TGFBR3. The presence in the genetic sample of the at least one genetic variation is used to determine whether the one or more subjects have EN, have an altered susceptibility to EN or are at risk of EN. In some embodiments, determining whether the one or more subjects have EN, are at risk of EN or have an altered susceptibility to EN includes a gynecological examination and/or medical history analysis of the one or more subjects, e.g., in addition to the nucleic acid sequence information. In some embodiments, at least one genetic sample is collected from blood, e.g., peripheral blood mononuclear cells (PBMC) or peripheral blood lymphocytes (PBL), saliva, urine, serum, tears, skin, tissue, or hair from at least one subject. In some embodiments, assaying the at least one genetic sample of one or more subjects includes purifying the at least one genetic sample. In some embodiments, assaying the at least one genetic sample of the one or more subjects includes amplifying at least one nucleotide or a specific region of one or more chromosomes in the at least one genetic sample. In some embodiments, assaying the at least one genetic sample of the one or more subjects includes assaying an unamplified sample for at least one nucleotide or a specific region of one or more chromosomes in the at least one genetic sample. In some embodiments, assaying the at least one genetic sample for at least one genetic variation includes a microarray analysis of the at least one sample. In some embodiments, the microarray analysis comprises a comparative genomic hybridization (CGH) array analysis. In one embodiment, the method includes detecting a deletion in TGFBR3, e.g., using a multiplex ligation-dependent probe amplification (MLPA), molecular beacon, aCGH, Invader assay, ligase chain reaction (LCR), or fluorescence in situ hybridization.

In one aspect, the invention provides a kit for screening for EN in a subject. The kit includes at least one component for assaying a genetic sample from the subject for the presence of at least one genetic variation in the genes listed in FIG. 1 or in FIG. 2 associated with EN. In one embodiment, a kit to screen for the TGFBR3 deletion, as described in Example 4, contains PCR primers such as Example 4 OUTER_FWD and OUTER_REV primers or similar primer pairs (see below) that yield a specific amplification product in genetic samples that contain the TGFBR3 deletion but do not yield an amplification product in genetic samples without the TGFBR3 deletion. In another embodiment, a kit to screen for the TGFBR3 deletion, as described in Example 4, contains an Invader oligonucleotide and primary probe that target the specific junction fragment of DNA sequence resulting from the deletion and produce a signal in genetic samples that contain the TGFBR3 deletion but do not produce a signal in genetic samples without the TGFBR3 deletion. In some embodiments, the at least one genetic variation is associated with a disruption or aberration of one or more RNA transcripts mentioned in FIG. 4. In some embodiments, the at least one genetic variation is associated with a disruption or aberration of one or more proteins expressed from one or more genes listed in FIG. 3, or encoded by one or more RNA transcripts mentioned in FIG. 4. One embodiment provides a kit for screening for endometriosis in one or more female subjects, the kit comprising reagents for assaying a genetic sample from the one or more subjects for the presence or absence of at least one genetic variation in one or more genes or regions in FIG. 1 or 3, or a combination thereof.

In some embodiments, screening the one or more subjects further comprises selecting one or more therapies based on the presence or absence of the one or more genetic variations. In some embodiments, the nucleic acid sequencing information is obtained for the whole genome or whole exome from the one or more subjects. In some embodiments, the nucleic acid sequencing information has already been obtained for the whole genome or whole exome from the one or more individuals and the nucleic acid information is obtained from in silico analysis. In other embodiments, the nucleic acid sequencing information is obtained for a selected portion of the whole genome or whole exome.

BRIEF DESCRIPTION OF THE DRAWINGS

FIG. 1 shows exemplary regions with genetic variations that are associated with EN, For each variation in each EN subject, the following are provided: chromosome for the variation, start and stop locations for original CNV; original CNV size; CNV type; subject case identifier (ID); gene symbol; and SEQ ID number corresponding to that region.

FIG. 2 shows exemplary CNV subregions with genetic variations that are associated with EN. For each variation in each EN case, the following are provided: chromosome for the variation; start and stop location of CNV subregion; CNV subregion size; CNV type; subject case ID(s); gene symbol; whether the CNV subregion overlaps an exon; the number of control (NVE) subjects with a CNV in that subregion, the number of EN cases with a CNV in that subregion; Fisher 2-tailed Exact Test (FET); odds ratio (OR); and whether the CNV subregion is of interest due to FET or OR, or a biological association with EN.

FIG. 3 summarizes the characteristics of genes in the regions associated with EN.

FIG. 4 summarizes transcripts in the regions associated with EN and corresponding SEQ ID Nos.

FIG. 10 provides a list of genes that are known drug targets as reported in Agarwal et al., *Nat. Rev. Drug Discov.* 12(8):575-6 (2013). Category defines the target as 'proven' if at least one drug selective for its protein product is approved and 'novel' if no drug has been approved yet. Gene lists the gene symbol for the drug target, latest phase lists the latest stage of drug development for the target, and competition lists the number of pharmaceutical companies that have a drug in development or launched for a given drug target.

DETAILED DESCRIPTION

Figure 5:
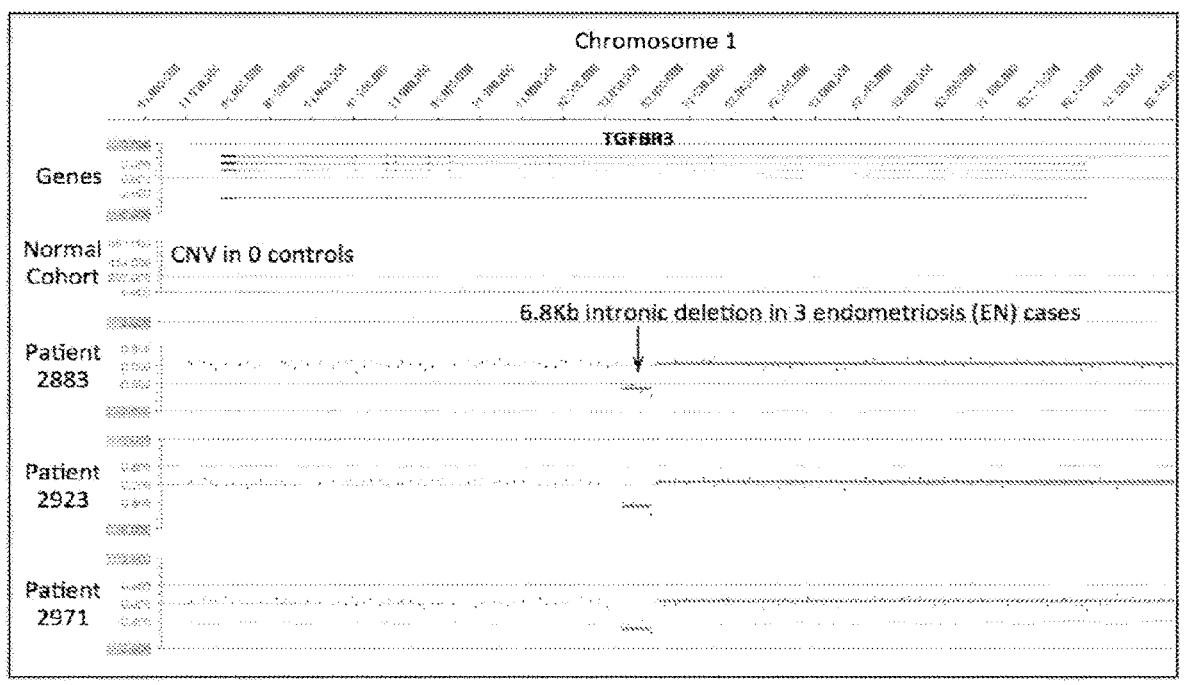
FIG. 5 schematic of deletion in chromosome 1 within TGFBR3 that is found in 3 EN cases and 0 controls.
Figure 6:
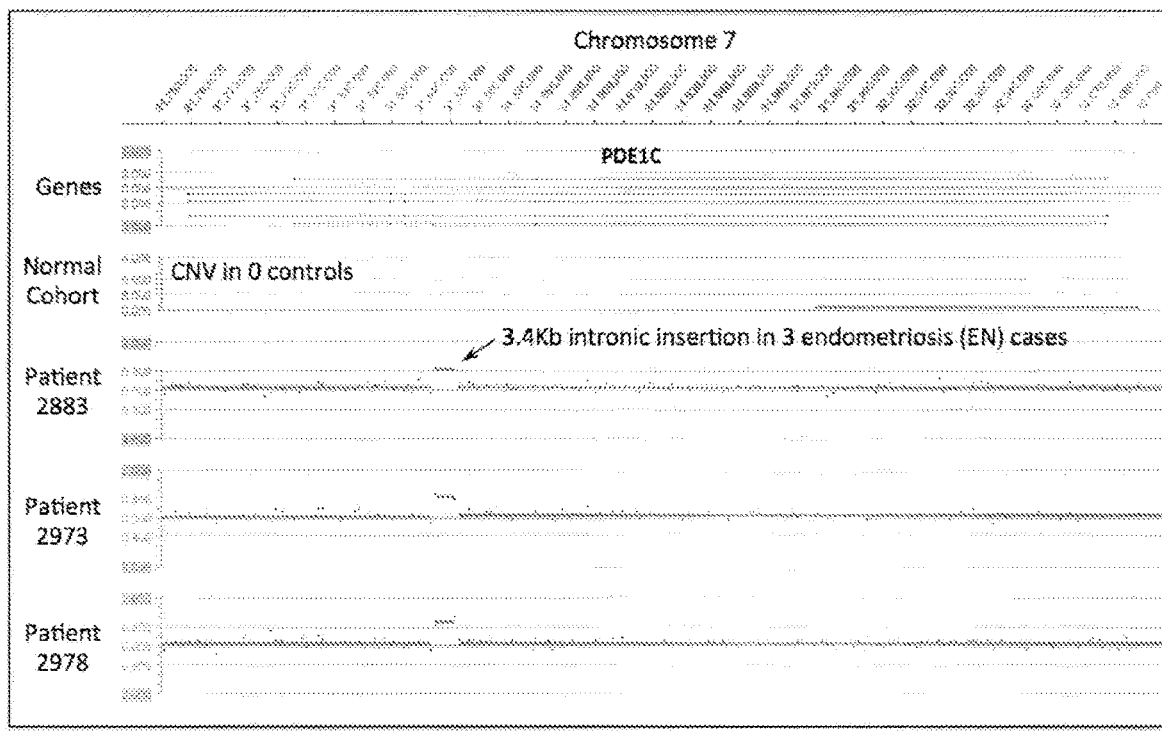
FIG. 6 schematic of insertion in chromosome 7 within PDE1C that is found in 3 EN cases and 0 controls.

Genetic risk can be conferred by subtle differences in individual genomes within a population. Genes can differ between individuals due to genomic variability, and the most frequent differences are due to single nucleotide polymorphisms (SNPs). SNPs can be located, on average, every 500-1000 base pairs in the human genome. Additional genetic polymorphisms in a human genome can be caused by duplication, insertion, deletion, translocation and/or inversion, of short and/or long stretches of DNA. Thus, in general, genetic variability among individuals occurs on many scales, ranging from single nucleotide changes, to gross changes in chromosome structure and function. Many copy number variations (CNVs) of DNA segments, including deletions, insertions, duplications and complex multisite variants, ranging in length from kilobases to megabases in size, have been discovered (Redon et al., *Nature*, 444: 444-54 (2006) and Estivill & Armengol, *PLoS Genetics*, 3:1787 (2007)). Known CNVs account for over 15% of the assembled human genome (Estivill & Armengol, supra). However, a majority of these variants are extremely rare and cover a small percentage of a human genome of any particular individual.

Described herein are methods of identifying variations in nucleic acids and genes associated with EN and their use in diagnosis, prognosis and theranosis. Also described herein are methods of screening for determining a subject's risk of or susceptibility to developing EN, or methods of diagnosing EN, based on identification and detection, or detection, of genetic nucleic acid variations. Also described herein are methods and compositions for treating, inhibiting and/or preventing EN using a therapeutic modality. The present disclosure further encompasses methods of assessing an individual for probability of response to a therapeutic agent for EN, methods for predicting the effectiveness of a therapeutic agent for EN, nucleic acids, polypeptides and antibodies useful in methods or kits, and computer-implemented functions, Kits for screening a sample from a subject to detect or determine a risk of or susceptibility to EN are also encompassed by the disclosure.

Genetic Variations Associated with Endometriosis

Genomic sequences within populations exhibit variability between individuals at many locations in the genome. For example, the human genome exhibits sequence variations, which occur on average every 500 base pairs. Such genetic variations in nucleic acid sequences are commonly referred to as polymorphisms or polymorphic sites. In some embodiments, these genetic variations can be found to be associated with EN using the methods disclosed herein. In some embodiments, these genetic variations comprise point mutations, e.g., single nucleotide polymorphisms (SNPs) or single nucleotide variants (SNVs), polymorphisms, translocations, insertions, deletions, amplifications, inversions, interstitial deletions, copy number variations (CNVs), loss of heterozygosity, or any combination thereof. In some embodiments, polymorphisms (e.g., polymorphic markers, genetic variations, or genetic variants) can comprise any nucleotide position at which two or more sequences are possible in a subject population. In some embodiments, each version of a nucleotide sequence with respect to the polymorphism can represent a specific allele of the polymorphism. In some embodiments, genomic DNA from a subject can contain two alleles for any given polymorphic marker, representative of each copy of the marker on each chromosome. In some embodiments, an allele can be a nucleotide sequence of a given location on a chromosome. Polymorphisms can comprise any number of specific alleles. In some embodiments of the disclosure, a polymorphism can be characterized by the presence of two or more alleles in a population. In some embodiments, the polymorphism can be characterized by the presence of three or more alleles. In some embodiments, the polymorphism can be characterized by four or more alleles, five or more alleles, six or more alleles, seven or more alleles, nine or more alleles, or ten or more alleles. In some embodiments an allele can be associated with one or more diseases or disorders. In some embodiments, genetic variations and alleles can be used to associate an inherited phenotype, for example, susceptibility EN, with a responsible genotype. In some embodiments, an allele, e.g., a risk allele, can be a variant allele that is statistically associated with EN, a risk of developing EN, or an increase susceptibility to EN. In some embodiments, genetic variations can be of any measurable frequency in the population, for example, a frequency higher than 10%, a frequency between 5-10%, a frequency between 1-5%, or frequency below 1%. As used herein, variant alleles can be alleles that differ from a reference allele. As used herein, a variant can be a segment of DNA that differs from the reference DNA, such as a genetic variation. In some embodiments, genetic variations can be used to track the inheritance of a gene that has not yet been identified, but whose approximate location is known.

As used herein, a haplotype can be information regarding the presence or absence of one or more genetic markers in a given chromosomal region in a subject. In some embodiments, a haplotype can be a segment of DNA characterized by one or more alleles arranged along the segment, for example, a haplotype can comprise one member of the pair of alleles for each genetic variation or locus. In some embodiments, the haplotype can comprise two or more alleles, three or more alleles, four or more alleles, five or more alleles, or any combination thereof, wherein, each allele can comprise one or more genetic variations along the segment.

In some embodiments, a genetic variation can be a functional aberration that can alter gene function, gene expression, protein expression, protein function, or any combination thereof. In some embodiments, a genetic variation can be a loss-of-function mutation, gain-of-function mutation, dominant negative mutation, or reversion. In some embodiments, a genetic variation can be part of a gene's coding region or regulatory regions. Regulatory regions can control gene expression and thus protein expression. In some embodiments, a regulatory region can be a segment of DNA wherein regulatory proteins, for example, transcription factors, can bind. In some embodiments a regulatory region can be positioned near the gene being regulated, for example, positions upstream of the gene being regulated. In some embodiments, a regulatory region (e.g., enhancer element) can be several thousands of base pairs upstream or downstream of a gene.

In some embodiments, variants can include changes that affect a polypeptide or protein, such as a change in expression level, sequence, function, localization, binding partners, or any combination thereof. In some embodiments, a genetic variation can be a frameshift mutation, nonsense mutation, missense mutation, neutral mutation, or silent mutation. For example, sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid, for example, if the change in the nucleic acid sequence causes a frame shift, the frame shift can result in a change in the encoded amino acids, and/or can result in the generation of a premature stop codon, causing generation of a truncated polypeptide. In some embodiments, a genetic variation associated with EN can be a synonymous change in one or more nucleotides, for example, a change that does not result in a change in the amino acid sequence. Such a polymorphism can, for example, alter splice sites, affect the stability or transport of mRNA, or otherwise affect the transcription or translation of an encoded polypeptide. In some embodiments, a synonymous mutation can result in the protein product having an altered structure due to rare codon usage that impacts protein folding during translation, which in some cases may alter its function and/or drug binding properties if it is a drug target. In some embodiments, the changes that can alter DNA increase the possibility that structural changes, such as amplifications or deletions, occur at the somatic level. A polypeptide encoded by the reference nucleotide sequence can be a reference polypeptide with a particular reference amino acid sequence, and polypeptides encoded by variant nucleotide sequences can be variant polypeptides with variant amino acid sequences.

In some embodiments, one or more variant polypeptides or proteins can be associated with EN. In some embodiments, variant polypeptides and changes in expression, localization, and interaction partners thereof, can be used to associate an inherited phenotype, EN, with a responsible genotype. In some embodiments, an EN associated variant polypeptide can be statistically associated with a diagnosis, prognosis, or theranosis of EN.

The most common sequence variants comprise base variations at a single base position in the genome, and such sequence variants, or polymorphisms, are commonly called single nucleotide polymorphisms (SNPs) or single nucleotide variants (SNVs). In some embodiments, a SNP represents a genetic variant present at greater than or equal to 1% occurrence in a population and in some embodiments a SNP can represent a genetic variant present at any frequency level in a population. A SNP can be a nucleotide sequence variation occurring when a single nucleotide at a location in the genome differs between members of a species or between paired chromosomes in a subject. SNPs can include variants of a single nucleotide, for example, at a given nucleotide position, some subjects can have a 'G', while others can have a 'C', SNPs can occur in a single mutational event, and therefore there can be two possible alleles possible at each SNP site; the original allele and the mutated allele. SNPs that are found to have two different bases in a single nucleotide position are referred to as biallelic SNPs, those with three are referred to as triallelic, and those with all four bases represented in the population are quadallelic. In some embodiments, SNPs can be considered neutral. In some embodiments SNPs can affect susceptibility to EN. SNP polymorphisms can have two alleles, for example, a subject can be homozygous for one allele of the polymorphism wherein both chromosomal copies of the individual have the same nucleotide at the SNP location, or a subject can be heterozygous wherein the two sister chromosomes of the subject contain different nucleotides. The SNP nomenclature as reported herein is be the official Reference SNP (rs) ID identification tag as assigned to each unique SNP by the National Center for Biotechnological Information (NCBI).

Another genetic variation of the disclosure can be copy number variations/variants (CNVs). CNVs can be alterations of the DNA of a genome that results in an abnormal number of copies of one or more sections of DNA. CNVs can be inherited or caused by de novo mutation and can be responsible for a substantial amount of human phenotypic variability, behavioral traits, and disease susceptibility. In one embodiment, CNVs of the current disclosure can be associated with risk of or susceptibility to EN. In some embodiments, CNVs can impact a single gene or include a contiguous set of genes. In some embodiments, CNVs can be caused by structural rearrangements of the genome, for example, translocations, insertions, deletions, amplifications, inversions, and interstitial deletions. In some embodiments, these structural rearrangements occur on one or more chromosomes. Low copy repeats (LCRs), which are region-specific repeat sequences, can be susceptible to these structural rearrangements, resulting in CNVs. Factors such as size, orientation, percentage similarity and the distance between the copies can influence the susceptibility of LCRs to mediate genomic rearrangement.

CNVs can account for genetic variation affecting a substantial proportion of the human genome, for example, known CNVs can cover over 15% of the human genome sequence (Estivill and Armengol, supra). CNVs can affect gene expression, phenotypic variation and adaptation by disrupting a gene or altering gene dosage, and can cause disease, for example, microdeletion and microduplication disorders, and can confer susceptibility to diseases and disorders. Updated information about the location, type, and size of known CNVs can be found in one or more databases, for example, the Database of Genomic Variants (projects.tcag.ca/variation/), which currently contains data for over 100,000 CNVs.

Other types of sequence variants can be found in the human genome and can be associated with a disease or disorder, including but not limited to, microsatellites. Microsatellite markers are stable, polymorphic, easily analyzed, and can occur regularly throughout the genome, making them especially suitable for genetic analysis. A polymorphic microsatellite can comprise multiple small repeats of bases, for example, CA repeats, at a particular site wherein the number of repeat lengths varies in a population. In some embodiments, microsatellites, for example, variable number of tandem repeats (VNTRs), can be short segments of DNA that have one or more repeated sequences, for example, about 2 to 5 nucleotides long, that can occur in non-coding DNA. In some embodiments, changes in microsatellites can occur during genetic recombination of sexual reproduction, increasing or decreasing the number of repeats found at an allele, or changing allele length.

Subjects

A subject, as used herein, can be an individual of any age from whom a sample containing nucleotides is obtained for analysis, e.g., by one or more methods described herein, so as to obtain genetic data, for example, a female adult, child, newborn, or fetus. In some embodiments, a subject can be any target of therapeutic administration. In some embodiments, a subject can be a test subject or a reference subject. In some embodiments, a subject can be associated with EN, asymptomatic or symptomatic, have increased or decreased susceptibility to EN, be associated or unassociated with a treatment or treatment regimen, or any combination thereof. As used in the present disclosure a cohort can represent an ethnic group, a patient group, a particular age group, a group not associated with EN, a group associated with EN, a group of asymptomatic female subjects, a group of symptomatic female subjects, or a group or subgroup of female subjects associated with a particular response to a treatment regimen or clinical trial. In some embodiments, a patient can be a subject afflicted with EN. In some embodiments, a patient can be a subject not afflicted with EN. In some embodiments, a female subject can be a test female subject, a female patient or a female candidate for a therapeutic, wherein genomic DNA from the female subject, female patient, or female candidate is obtained for analysis by one or more methods of the present disclosure herein, so as to obtain genetic variation information of the subject, patient or candidate.

In some embodiments, the sample can be obtained prenatally from a female fetus or embryo or from the mother, for example, from fetal or embryonic cells in the maternal circulation. In some embodiments, the sample can be obtained with the assistance of a health care provider, for example, to draw blood. In some embodiments, the sample can be obtained without the assistance of a health care provider, for example, where the sample is obtained noninvasively, such as a saliva sample, or a sample comprising buccal cells that is obtained using a buccal swab or brush, or a mouthwash sample.

The present disclosure also provides methods for assessing genetic variations in female subjects who are members of a target population. Such a target population is in some embodiments a population or group of subjects at risk of developing EN, based on, for example, other genetic factors, biomarkers, biophysical parameters, family history of EN, previous screening or medical history, or any combination thereof.

In some embodiments, female subjects can be from specific age subgroups, such as those over the age of 1, over the age of 2, over the age of 3, over the age of 4, over the age of 5, over the age of 6, over the age of 7, over the age of 8, over the age of 9, over the age of 10, over the age of 15, over the age of 20, over the age of 25, over the age of 30, over the age of 35, over the age of 40, over the age of 45, over the age of 50, over the age of 55, over the age of 60, over the age of 65, over the age of 70, over the age of 75, over the age of 80, or over the age of 85. Other embodiments of the disclosure pertain to other age groups, such as subjects aged less than 85, such as less than age 80, less than age 75, less than age 70, less than age 65, less than age 60, less than age 55, less than age 50, less than age 45, less than age 40, less than age 35, less than age 30, less than age 25, less than age 20, less than age 15, less than age 10, less than age 9, less than age 8, less than age 6, less than age 5, less than age 4, less than age 3, less than age 2, or less than age 1. Other embodiments relate to female subjects with age at onset of the disease in any of particular age or age ranges defined by the numerical values described in the above or other numerical values bridging these numbers. It is also contemplated that a range of ages can be relevant in certain embodiments, such as age at onset at more than age 15 but less than age 20. Other age ranges are however also contemplated, including all age ranges bracketed by the age values listed in the above.

The genetic variations of the present disclosure found to be associated with EN can show similar association in other female populations. Particular embodiments comprising subject female populations are thus also contemplated and within the scope of the disclosure. Such embodiments relate to female subjects that are from one or more human populations including, but not limited to, Caucasian, European, American, Ashkenazi Jewish, Sephardi Jewish, Eurasian, Asian, Central/South Asian, East Asian, Middle Eastern, African, Hispanic, and Oceanic populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Czech, Greek and Turkish populations. The racial contribution in female subjects can also be determined by genetic analysis, for example, genetic analysis of ancestry can be carried out using unlinked microsatellite markers such as those set out in Smith et al. (*Am. J. Hum. Genet.*, 74:1001 (2004)).

It is also well known to the person skilled in the art that certain genetic variations have different population frequencies in different populations, or are polymorphic in one population but not in another. A person skilled in the art can however apply the methods available and as thought herein to practice the present disclosure in any given human population. This can include assessment of genetic variations of the present disclosure, so as to identify those markers that give strongest association within the specific population. Thus, the at-risk variants of the present disclosure can reside on different haplotype background and in different frequencies in various human populations.

Samples

Samples that are suitable for use in the methods described herein can be from a subject and can contain genetic or proteinaceous material, for example, genomic DNA (gDNA). Genetic material can be extracted from one or more biological samples including but not limited to, blood, saliva, urine, mucosal scrapings of the lining of the mouth, expectorant, serum, tears, skin, tissue, or hair.

In some embodiments, the sample can comprise cells or tissue, for example, cell lines. Exemplary cell types from which genetic material can be obtained using the methods described herein and include but are not limited to, a blood cell: such as a B lymphocyte, T lymphocyte, leukocyte, erythrocyte, macrophage, or neutrophil; a muscle cell such as a skeletal cell, smooth muscle cell or cardiac muscle cell: a germ cell, such as a sperm or egg; an epithelial cell; a connective tissue cell, such as an adipocyte, chondrocyte; fibroblast or osteoblast; a neuron; an astrocyte; a stromal cell; an organ specific cell, such as a kidney cell, pancreatic cell, liver cell, or a keratinocyte; a stem cell; or any cell that develops there from. A cell from which gDNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Generally any type of stem cell can be used including, without limitation, an embryonic stem cell, adult stem cell, an induced pluripotent stem cell created from an adult cell type such as fibroblasts derived from skin or pluripotent stem cell.

In some embodiments, a sample can be processed for DNA isolation, for example, DNA in a cell or tissue sample can be separated from other components of the sample. Cells can be harvested from a biological sample using standard techniques known in the art, for example, by centrifuging a cell sample and resuspending the pelleted cells, for example, in a buffered solution, for example, phosphate-buffered saline (PBS). In some embodiments, after centrifuging the cell suspension to obtain a cell pellet, the cells can be lysed to extract DNA. In some embodiments, the sample can be concentrated and/or purified to isolate DNA. All samples obtained from a female subject, including those subjected to any sort of further processing, are considered to be obtained from the subject. In some embodiments, standard techniques and kits known in the art can be used to extract genomic DNA from a biological sample, including, for example, phenol extraction, a QIAamp® Tissue Kit (Qiagen, Chatsworth, Calif.), a Wizard® Genomic DNA purification kit (Promega), or a Qiagen Autopure method using Puregene chemistry, which can enable purification of highly stable DNA well-suited for archiving.

In some embodiments, determining the identity of an allele or determining copy number can, but need not, include obtaining a sample comprising DNA from a subject, and/or assessing the identity, copy number, presence or absence of one or more genetic variations and their chromosomal locations in the sample. The individual or organization that performs the determination need not actually carry out the physical analysis of a sample from a subject. In some embodiments, the methods can include using information obtained by analysis of the sample by a third party. In some embodiments, the methods can include steps that occur at more than one site. For example, a sample can be obtained from a subject at a first site, such as at a health care provider or at the subject's home in the case of a self-testing kit. The sample can be analyzed at the same or a second site, for example, at a laboratory or other testing facility.

Methods of Screening

As used herein, screening a subject may include diagnosing or determining, theranosing, or determining the risk of or susceptibility to developing (prognosing) EN. In particular embodiments, the disclosure is a method of determining the presence of, a risk of developing or a susceptibility to, EN, by detecting at least one genetic variation in a sample from a subject as described herein. In some embodiments, detection of particular alleles, markers, variations, or haplotypes is indicative of the presence of or susceptibility to EN.

Within any given population, there can be an absolute susceptibility of developing a disease or trait, defined as the chance of a person developing the specific disease or trait over a specified time-period. Susceptibility (e.g., being at-risk) is typically measured by looking at very large numbers of people, rather than at a particular individual. As described herein, certain copy number variations (genetic variations) are found to be useful for susceptibility assessment of EN. Susceptibility assessment can involve detecting particular genetic variations in the genome of individuals undergoing assessment. Particular genetic variations are found more frequently in individuals with EN, than in individuals without EN. Therefore, these genetic variations have predictive value for detecting EN, risk of developing EN, or a susceptibility to EN, in an individual. Without intending to be limited by theory, it is believed that the genetic variations described herein to be associated with susceptibility of EN represent functional variants predisposing to the disease. In some embodiments, a genetic variation can confer a susceptibility of the condition, for example, carriers of the genetic variation are at a different risk of the condition than non-carriers. In one embodiment, the presence of a genetic variation is indicative of increased susceptibility to or the presence of EN.

Screening can be performed using any method. In some embodiments, screening can be performed using Polymerase Chain Reaction (PCR). In one embodiment, screening can be performed using Array Comparative Genomic Hybridization (aCGH). In some embodiments, the genetic variation information as it relates to the current disclosure can be used in conjunction with any symptomatic screening tests.

In some embodiments, information from any of the above screening methods (e.g., specific symptoms or genetic variation data) can be used to define a subject as a test subject or reference subject. In some embodiments, information from any of the above screening methods can be used to associate a subject with a test or reference population, for example, a subject in a population.

In one embodiment, an association with EN can be determined by the statistical likelihood of the presence of a genetic variation in a subject with EN, for example, an unrelated individual or a first or second-degree relation of the subject. In some embodiments, an association with EN can be determined by determining the statistical likelihood of the absence of a genetic variation in an unaffected reference subject, for example, an unrelated individual or a first or second-degree relation of the subject. The methods described herein can include obtaining and analyzing a sample from one or more suitable reference subjects.

As used herein, susceptibility can be proneness of a subject towards the development of EN, or towards resisting development of EN, than one or more control subjects. In some embodiments, susceptibility can encompass increased susceptibility. For example, particular nucleic acid variations of the disclosure as described herein can be characteristic of increased susceptibility to development of EN. In some embodiments, susceptibility can encompass decreased susceptibility, for example, particular nucleic acid variations of the disclosure as described herein can be characteristic of decreased susceptibility to development of EN. As used herein, a subject at risk of developing EN has a greater chance of developing EN relative to the general population or to one or more subjects without a specific genetic variation.

As described herein, a genetic variation predictive of susceptibility to or presence of EN can be one where the particular genetic variation is more frequently present in a subject with the condition (affected), compared to the frequency of its presence in a reference group (control), such that the presence of the genetic variation is indicative of susceptibility to or presence of EN. In some embodiments, the reference group can be a population sample, for example, a random sample from the general population or a mixture of two or more samples from a population. In some embodiments, disease-free controls can be characterized by the absence of one or more specific EN-associated symptoms, for example, individuals who have not experienced symptoms associated with EN. In some embodiments, the disease-free control group is characterized by the absence of one or more EN-specific risk factors, for example, at least one genetic and/or environmental risk factor. In some embodiments, a reference sequence can be referred to for a particular site of genetic variation. In some embodiments, a reference allele can be a wild-type allele and can be chosen as either the first sequenced allele or as the allele from a control individual. In some embodiments, one or more reference subjects can be characteristically matched with one or more affected subjects, for example, with matched aged, gender or ethnicity.

A person skilled in the art can appreciate that for genetic variations with two or more alleles present in the population being studied, and wherein one allele can found in increased frequency in a group of individuals with EN in the population, compared with controls, the other allele(s) of the marker can be found in decreased frequency in the group of individuals with the trait or disease, compared with controls. In such a case, one allele of the marker, for example, the allele found in increased frequency in individuals with EN, can be the at-risk allele, while the other allele(s) can be neutral or even protective.

A genetic variant associated with EN can be used to predict the susceptibility of EN for a given genotype. For any genetic variation, there can be one or more possible genotypes, for example, homozygote for the at-risk variant (e.g., in autosomal recessive disorders), heterozygote, and non-carrier of the at-risk variant. In some embodiments, susceptibility associated with variants at multiple loci can be used to estimate overall susceptibility. For multiple genetic variants, there can be k (k=3^n*2^P) possible genotypes; wherein n can be the number of autosomal loci and p can be the number of gonosomal (sex chromosomal) loci. Overall susceptibility assessment calculations can assume that the relative susceptibilities of different genetic variants multiply, for example, the overall susceptibility associated with a particular genotype combination can be the product of the susceptibility values for the genotype at each locus. If the susceptibility presented is the relative susceptibility for a person, or a specific genotype for a person, compared to a reference population, then the combined susceptibility can be the product of the locus specific susceptibility values and can correspond to an overall susceptibility estimate compared with a population. If the susceptibility for a person is based on a comparison to non-carriers of the at-risk allele, then the combined susceptibility can correspond to an estimate that compares the person with a given combination of genotypes at all loci to a group of individuals who do not carry at-risk variants at any of those loci. The group of non-carriers of any at-risk variant can have the lowest estimated susceptibility and can have a combined susceptibility, compared with itself, for example, non-carriers, of 1.0, but can have an overall susceptibility, compared with the population, of less than 1.0.

Overall risk for multiple risk variants can be performed using standard methodology. Genetic variations described herein can form the basis of risk analysis that combines other genetic variations known to increase risk of EN, or other genetic risk variants for EN. In certain embodiments of the disclosure, a plurality of variants (genetic variations, variant alleles, and/or haplotypes) can be used for overall risk assessment. These variants are in some embodiments selected from the genetic variations as disclosed herein. Other embodiments include the use of the variants of the present disclosure in combination with other variants known to be useful for screening for EN or a susceptibility to EN. In such embodiments, the genotype status of a plurality of genetic variations, markers and/or haplotypes is determined in an individual, and the status of the individual compared with the population frequency of the associated variants, or the frequency of the variants in clinically healthy subjects, such as age-matched and sex-matched subjects.

Methods known in the art, such as the use of available algorithms and software can be used to identify, or call, significant genetic variations, including but not limited to, algorithms of DNA Analytics or DNAcopy, iPattern and/or QuantiSNP. In some embodiments, a threshold log ratio value can be used to determine losses and gains. For example, using DNA Analytics, a log 2ratio cutoff of 0.25 and −0.25 to classify CNV gains and losses respectively may be used. As a further example, using DNAcopy, a log 2ratio cutoff of 0.35 and −0.35 to classify CNV gains and losses respectively may be used. In some embodiments, the information and calls from two or more of the methods described herein can be compared to each other to identify significant genetic variations more or less stringently. For example, CNV calls generated by both DNA Analytics and DNAcopy algorithms may be defined as stringent CNVs. In some embodiments, significant or stringent genetic variations can be tagged as identified or called if it can be found to have a minimal reciprocal overlap to a genetic variation detected by one or more platforms and/or methods described herein. For example, a minimum of 50% reciprocal overlap can be used to tag the CNVs as identified or called.

In some embodiments, multivariate analyses or joint risk analyses, including the use of multiplicative model for overall risk assessment, and can subsequently be used to determine the overall risk conferred based on the genotype status at the multiple loci. Use of a multiplicative model, for example, assuming that the risk of individual risk variants multiply to establish the overall effect, allows for a straightforward calculation of the overall risk for multiple markers. The multiplicative model is a parsimonious model that usually fits the data of complex traits reasonably well Deviations from multiplicity have been rarely described in the context of common variants for common diseases, and if reported are usually only suggestive since very large sample sizes can be required to be able to demonstrate statistical interactions between loci. Assessment of risk based on such analysis can subsequently be used in the methods, uses and kits of the disclosure, as described herein.

In some embodiments, the significance of increased or decreased susceptibility can be measured by a percentage. In some embodiments, a significant increased susceptibility can be measured as a relative susceptibility of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, at least 5.0, at least 6.0, at least 7.0, at least 8.0, at least 9.0, at least 10.0, and at least 15.0. In some embodiments, a relative susceptibility of at least 2.0, at least 3.0, at least 4.0, at least, 5.0, at least 6.0, or at least 10.0 is significant. Other values for significant susceptibility are also contemplated, for example, at least 2.5, 3.5, 4.5, 5.5, or any suitable other numerical values, wherein the values are also within scope of the present disclosure. In some embodiments, a significant increase in susceptibility is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, 1000%, and 1500%, In one particular embodiment, a significant increase in susceptibility is at least 100%. In other embodiments, a significant increase in susceptibility is at least 200%, at least 300%, at least 400%, at least 500%, at least 700%, at least 800%, at least 900% and at least 1000%. Other cutoffs or ranges as deemed suitable by the person skilled in the art to characterize the disclosure are also contemplated, and those are also within scope of the present disclosure. In certain embodiments, a significant increase in susceptibility is characterized by a p-value, such as a p-value of less than 0.5, less than 0.4, less than 0.3, less than 0.2, less than 0.1, less than 0.05, less than 0.01, less than 0.001, less than 0.0001, less than 0.00001, less than 0.00001, less than 0.0000001, less than 0.00000001, or less than 0.000000001.

In some embodiments, an individual who is at a decreased susceptibility for or the lack of presence of EN can be an individual in whom at least one genetic variation, conferring decreased susceptibility for or the lack of presence of EN is identified. In some embodiments, the genetic variations conferring decreased susceptibility are also protective. In one aspect, the genetic variations can confer a significant decreased susceptibility of or lack of presence of EN.

In some embodiments, significant decreased susceptibility can be measured as a relative susceptibility of less than 0.9, including but not limited to less than 0.9, less than 0.8, less than 0.7, less than 0.6, less than 0.5, less than 0.4, less than 0.3, less than 0.2 and less than 0.1. In some embodiments, the decrease in susceptibility is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. Other cutoffs or ranges as deemed suitable by the person skilled in the art to characterize the disclosure are however also contemplated, and those are also within scope of the present disclosure. In certain embodiments, a significant decrease in susceptibility is characterized by a p-value, such as a p-value of less than 0.05, less than 0.01, less than 0.001, less than 0.0001, less than 0.00001, less than 0.000001, less than 0.0000001, less than 0.00000001, or less than 0.000000001. Other tests for significance can be used, for example, a Fisher's exact test. Other statistical tests of significance known to the skilled person are also contemplated and are also within scope of the disclosure.

In some embodiments, the significance of increased or decreased susceptibility can be determined according to the ratio of measurements from a test subject to a reference subject. In one embodiment, losses or gains of one or more CNVs can be determined according to a threshold $\log_2$ ratio determined by these measurements. In some embodiments, a $\log_2$ ratio value greater than 0.35 is indicative of a gain of one or more CNVs. In some embodiments, a $\log_2$ ratio value less than −0.35 is indicative of a loss of one or more CNVs.

In some embodiments, the combined or overall susceptibility associated with a plurality of variants associated with EN can also be assessed, for example, the genetic variations described herein to be associated with susceptibility to EN can be combined with other common genetic risk factors. Combined risk for such genetic variants can be estimated in an analogous fashion to the methods described herein.

Calculating risk conferred by a particular genotype for the individual can be based on comparing the genotype of the individual to previously determined risk expressed, for example, as a relative risk (RR) or an odds ratio (OR), for the genotype, for example, for a heterozygous carrier of an at-risk variant for EN. An odds ratio can be a statistical measure used as a metric of causality. For example, in genetic disease research it can be used to convey the significance of a variant in a disease cohort relative to an unaffected/normal cohort. The calculated risk for the individual can be the relative risk for a subject, or for a specific genotype of a subject, compared to the average population. The average population risk can be expressed as a weighted average of the risks of different genotypes, using results from a reference population, and the appropriate calculations to calculate the risk of a genotype group relative to the population can then be performed. Alternatively, the risk for an individual can be based on a comparison of particular genotypes, for example, heterozygous carriers of an at-risk allele of a marker compared with non-carriers of the at-risk allele. Using the population average can, in certain embodiments, be more convenient, since it provides a measure which can be easy to interpret for the user, for example, a measure that gives the risk for the individual, based on his/her genotype, compared with the average in the population.

In certain embodiments of the disclosure, a genetic variation is correlated to EN by referencing genetic variation data to a look-up table that comprises correlations between the genetic variation and EN. The genetic variation in certain embodiments comprises at least one indication of the genetic variation. In some embodiments, the table comprises a correlation for one genetic variation. In other embodiments, the table comprises a correlation for a plurality of genetic variations. In both scenarios, by referencing to a look-up table that gives an indication of a correlation between a genetic variation and EN, a risk for EN, or a susceptibility to EN, can be identified in the individual from whom the sample is derived.

The screening applications of EN-associated genetic variations, as described herein, can, for example, be performed by an individual, a health professional, or a third party, for example, a service provider who interprets genotype information from the subject.

A medical professional can initiate or modify treatment after receiving information regarding a subject's screening for EN, for example. In some embodiments, a medical professional can recommend a change in therapy. In some embodiments, a medical professional can enroll a subject in a clinical trial for, by way of example, detecting correlations between a haplotype as described herein and any measurable or quantifiable parameter relating to the outcome of the treatment as described above.

Also provided herein are databases that include a list of genetic variations as described herein, and wherein the list can be largely or entirely limited to genetic variations identified as useful for screening EN as described herein. The list can be stored, for example, on a flat file or computer-readable medium. The databases can further include information regarding one or more subjects, for example, whether a subject is affected or unaffected, clinical information such as endophenotype, age of onset of symptoms, any treatments administered and outcomes, for example, data relevant to pharmacogenomics, diagnostics, prognostics or theranostics, and other details, for example, data about the disorder in the subject, or environmental or other genetic factors. The databases can be used to detect correlations between a particular haplotype and the information regarding the subject.

The methods described herein can also include the generation of reports for use, for example, by a subject, care giver, or researcher, that include information regarding a subject's genetic variations, and optionally further information such as treatments administered, treatment history, medical history, predicted response, and actual response. The reports can be recorded in a tangible medium, e.g., a computer-readable disk, a solid state memory device, or an optical storage device.

Methods of Screening Using Variations in Polypeptides and/or RNA

In some embodiments of the disclosure, screening of EN can be made by examining or comparing changes in expression, localization, binding partners, and composition of a polypeptide encoded by a nucleic acid associated with EN, for example, in those instances where the genetic variations of the present disclosure results in a change in the composition or expression of the polypeptide and/or RNA, for example, mRNAs, miRNAs, and other noncoding RNAs (ncRNAs). Thus, screening of EN can be made by examining expression and/or composition of one of these polypeptides and/or RNA, or another polypeptide and/or RNA encoded by a nucleic acid associated with EN, in those instances where the genetic variation of the present disclosure results in a change in the expression, localization, binding partners, and/or composition of the polypeptide and/or RNA. In some embodiments, screening can comprise diagnosing a subject. In some embodiments, screening can comprise determining a prognosis of a subject, for example, determining the susceptibility of developing EN. In some embodiments, screening can comprise theranosing a subject.

The genetic variations described herein that show association to EN can play a role through their effect on one or more of these nearby genes. For example, while not intending to be limited by theory, it is generally expected that a deletion of a chromosomal segment comprising a particular gene, or a fragment of a gene, can either result in an altered composition or expression, or both, of the encoded protein and/or mRNA. Likewise, duplications, or high number copy number variations, are in general expected to result in increased expression of encoded polypeptide and/or RNA if the duplication encompasses the whole gene. It is also known to those skilled in the art that segments of DNA can be duplicated, triplicated, quadruplicated, or amplified many times and result in increasingly higher levels of expression of the gene if it is encompassed by these multiplicated segments of DNA. Those skilled in the art also know that one or both breakpoints of a duplication or other level of amplification can disrupt a gene and thus result in loss of function, such as the expressed protein encoded by the transcript is truncated. Further, those skilled in the art anticipate that an amplified segment of DNA can occur in tandem (e.g., multiple gene copies adjacent to each other on the chromosome) or can insert, into a site far away from the original chromosomal location or even on another chromosome. Thus, in some cases a gene not contained within the amplified segment of DNA is impacted by the chromosomal rearrangement. Such complex rearrangements can be mapped, for example, by fluorescence in situ hybridization (FISH) methods. Other possible mechanisms affecting genes within or near a genetic variation region include, for example, effects on transcription, effects on RNA splicing, alterations in relative amounts of alternative splice forms of mRNA, effects on RNA stability, effects on transport from the nucleus to cytoplasm, and effects on the efficiency and accuracy of translation. Thus, DNA variations can be detected directly, using the subjects unamplified or amplified genomic DNA, or indirectly, using RNA or DNA obtained from the subject's tissue(s) that are present in an aberrant form or expression level as a result of the genetic variations of the disclosure showing association to EN.

In some embodiments, the genetic variations of the disclosure showing association to EN can affect the expression of a gene within the genetic variation region. Certain genetic variation regions can have flanking duplicated segments, and genes within such segments can have altered expression and/or composition as a result of such genomic alterations. It is also well known that regulatory elements affecting gene expression can be located far away, even as far as tens or hundreds of kilobases away, from the promoter region of a gene. Thus, regulatory elements for genes that are located outside the genetic variation region can be located within the genetic variation, and thus affect the expression of genes located outside the genetic variation. It is thus contemplated that the detection of the genetic variations described herein, can be used for assessing expression for one or more of associated genes.

In some embodiments, genetic variations of the disclosure showing association to EN can affect protein expression at the translational level. It can be appreciated by those skilled in the art that this can occur by increased or decreased expression of one or more microRNAs (miRNAs) that regulates expression of a protein known to be important, or implicated, in the cause, onset, or progression of EN. Increased or decreased expression of the one or more miRNAs can result from gain or loss of the whole miRNA gene, disruption of a portion of the gene (e.g., by an indel or CNV), or even a single base change (SNP or SNV) that produces an altered, non-functional or aberrant functioning miRNA sequence. It can also be appreciated by those skilled in the art that the expression of protein, for example, one known to cause EN by increased or decreased expression, can result due to a genetic variation that results in alteration of an existing miRNA binding site within the protein's mRNA transcript, or even creates a new miRNA binding site that leads to aberrant protein expression.

A variety of methods can be used for detecting protein composition and/or expression levels, including but not limited to enzyme linked immunosorbent assays (ELISA), Western blots, spectroscopy, mass spectrometry, peptide arrays, colorimetry, electrophoresis, isoelectric focusing, immunoprecipitations, immunoassays, and immunofluorescence and other methods well-known in the art. A test sample from a subject can be assessed for the presence of an alteration in the expression and/or an alteration in composition of the polypeptide encoded by a nucleic acid associated with EN. An "alteration" in the polypeptide expression or composition, as used herein, refers to an alteration in expression or composition in a test sample, as compared to the expression or composition of the polypeptide in a control sample. Such alteration can, for example, be an alteration in the quantitative polypeptide expression or can be an alteration in the qualitative polypeptide expression, for example, expression of a mutant polypeptide or of a different splicing variant, or a combination thereof. In some embodiments, screening for EN can be made by detecting a particular splicing variant encoded by a nucleic acid associated with EN, or a particular pattern of splicing variants.

Antibodies can be polyclonal or monoclonal and can be labeled or unlabeled. An intact antibody or a fragment thereof can be used. The term "labeled", with regard to the probe or antibody, is intended to encompass direct labeling of the probe or antibody by coupling a detectable substance to the probe or antibody, as well as indirect labeling of the probe or antibody by reactivity with another reagent that is directly labeled as previously described herein. Other non-limiting examples of indirect labeling include detection of a primary antibody using a labeled secondary antibody, for example, a fluorescently-labeled secondary antibody and end-labeling of a DNA probe with biotin such that it can be detected with fluorescently-labeled streptavidin.

Detecting Genetic Variations Associated with Endometriosis

Described herein, are methods that can be used to detect genetic variations. Detecting specific genetic variations, for example, polymorphic markers and/or haplotypes, copy number, absence or presence of an allele, or genotype associated with EN as described herein, can be accomplished by methods known in the art for analyzing nucleic acids and/or detecting sequences at polymorphic or genetically variable sites, for example, amplification techniques, hybridization techniques, sequencing, arrays, or any combination thereof. Thus, by use of these methods disclosed herein or other methods available to the person skilled in the art, one or more alleles at polymorphic markers, including microsatellites, SNPs, CNVs, or other types of genetic variations, can be identified in a sample obtained from a subject.

Nucleic Acids

The nucleic acids and polypeptides described herein can be used in methods and kits of the present disclosure. In some embodiments, aptamers that specifically bind the nucleic acids and polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example, a translated gene, or non-coding, for example, a regulatory region, or any fragments, derivatives, mimetics or complements thereof. In some embodiments, nucleic acids can comprise oligonucleotides, nucleotides, polynucleotides, nucleic acid sequences, genomic sequences, antisense nucleic acids, DNA regions, probes, primers, genes, regulatory regions, introns, exons, open-reading frames, binding sites, target nucleic acids and allele-specific nucleic acids.

"Isolated" nucleic acids, as used herein, are separated from nucleic acids that normally flank the gene or nucleotide sequence (as in genomic sequences) and/or has been completely or partially purified from other transcribed sequences (e.g., as in an RNA library). For example, isolated nucleic acids of the disclosure can be substantially isolated with respect to the complex cellular milieu in which it naturally occurs, or culture medium when produced by recombinant techniques, or chemical precursors or other chemicals when chemically synthesized. In some instances, the isolated material can form part of a composition, for example, a crude extract containing other substances, buffer system or reagent mix. In some embodiments, the material can be purified to essential homogeneity using methods known in the art, for example, by polyacrylamide gel electrophoresis (PAGE) or column chromatography (e.g., HPLC). With regard to genonic DNA (gDNA), the term "isolated" also can refer to nucleic acids that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the gDNA of the cell from which the nucleic acid molecule is derived.

Nucleic acids can be fused to other coding or regulatory sequences can be considered isolated. For example, recombinant DNA contained in a vector is included in the definition of "isolated" as used herein. In some embodiments, isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein Such nucleic acid sequences can be detected and/or isolated by allele- or sequence-specific hybridization (e.g., under high stringency conditions), Stringency conditions and methods for nucleic acid hybridizations are well known to the skilled person (see, e.g., Current Protocols in Molecular Biology, Ausubel, F. et al., John Wiley & Sons, (1998), and Kraus, M. and Aaronson. S., Methods Enzymol, 200:546-556 (1991), the entire teachings of which are incorporated by reference herein.

Calculations of "identity" or "percent identity" between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e., % identity=# of identical positions/total # of positions×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, and Altschul, *Proc. Natl. Acad. Sci. USA,* 90:5873 (1993). Such an algorithm is incorporated into the NBLAST and XBLAST programs (version 2.0), as described in Altschul et al., *Nucleic Acids Res.,* 25:3389 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge. UK).

"Probes" or "primers" can be oligonucleotides that hybridize in a base-specific manner to a complementary strand of a nucleic acid molecule. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. It can be appreciated by those skilled in the art that probes for detection of amplified or unamplified nucleic acid molecules can also include an Invader oligonucleotide and probe pair. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 15, typically about 20-25, and in certain embodiments about 40, 50 or 75, consecutive nucleotides of a nucleic acid molecule.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the compliments thereof. In some embodiments, the probe or primer can be at least 70% identical, at least 80% identical, at least 85% identical, at least 90% identical, or at least 95% identical, to the contiguous nucleotide sequence or to the complement of the contiguous nucleotide sequence.

In one embodiment, a nucleic acid probe can be an oligonucleotide capable of hybridizing with a complementary region of a gene associated with EN containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. In some embodiments. DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained fallowing in vivo excision, and the cloned insert can be sequenced in either or both orientations by art-recognized methods to identify the correct reading frame encoding a polypeptide of the appropriate molecular weight.

Using these or similar methods, the polypeptide and the DNA encoding the polypeptide can be isolated, sequenced and further characterized.

In some embodiments, nucleic acid can comprise one or more polymorphisms, variations, or mutations, for example, single nucleotide polymorphisms (SNPs), copy number variations (CNVs), for example, insertions, deletions, inversions, and translocations. In some embodiments, nucleic acids can comprise analogs, for example, phosphorothioates, phosphoramidates, methyl phosphonate, chiral methyl phosphonates, 2-0-methyl ribonucleotides, or modified nucleic acids, for example, modified backbone residues or linkages, or nucleic acids combined with carbohydrates, lipids, protein or other materials, or peptide nucleic acids (PNAs), for example, chromatin, ribosomes, and transcriptosomes. In some embodiments nucleic acids can comprise nucleic acids in various structures, for example, A DNA, B DNA, Z-form DNA, siRNA, tRNA, and ribozymes. In some embodiments, the nucleic acid may be naturally or non-naturally polymorphic, for example, having one or more sequence differences, for example, additions, deletions and/or substitutions, as compared to a reference sequence. In some embodiments, a reference sequence can be based on publicly available information, for example, the U.C. Santa Cruz Human Genome Browser Gateway (genome.ucsc.edu/cgi-bin/hg-Gateway) or the NCBI website (www.ncbi.nlm.nih.gov). In some embodiments, a reference sequence can be determined by a practitioner of the present disclosure using methods well known in the art, for example, by sequencing a reference nucleic acid.

In some embodiments, a probe can hybridize to an allele, SNP, or CNV as described herein. In some embodiments, the probe can bind to another marker sequence associated with EN as described herein.

One of skill in the art would know how to design a probe so that sequence specific hybridization can occur only if a particular allele is present in a genomic sequence from a test sample. The disclosure can also be reduced to practice using any convenient genotyping method, including commercially available technologies and methods for genotyping particular genetic variations Control probes can also be used, for example, a probe that binds a less variable sequence, for example, a repetitive DNA associated with a centromere of a chromosome, can be used as a control. In some embodiments, probes can be obtained from commercial sources. In some embodiments, probes can be synthesized, for example, chemically or in vitro, or made from chromosomal or genomic DNA through standard techniques. In some embodiments sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as $^{32}P$ or $^{3}H$, a fluorescent label, such as FITC, a chromophore label, an affinity-ligand label, an enzyme label, such as alkaline phosphatase, horseradish peroxidase, or 12 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule, A nucleotide can be directly incorporated into a probe with standard techniques, for example, nick translation, random priming, and PCR labeling.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include $^{14}C$, $^{123}I$, $^{124}I$, $^{125}I$, Tc99m, $^{32}P$, $^{33}P$, $^{35}S$ or $^{3}H$.

Other labels can also be used in the methods of the present disclosure, for example, backbone labels. Backbone labels comprise nucleic acid stains that bind nucleic acids in a sequence independent manner. Non-limiting examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

In some embodiments, fluorophores of different colors can be chosen, for example, 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, TRITC, rhodamine, tetramethylrhodamine, R-phycoerythrin, Cy-3. Cy-5, Cy-7, Texas Red, Phar-Red, allophycocyanin (APC), and CASCADE blue acetylazide, such that each probe in or not in a set can be distinctly visualized. In some embodiments, fluorescently labeled probes can be viewed with a fluorescence microscope and an appropriate filter for each fluorophore, or by using dual or triple band-pass filter sets to observe multiple fluorophores. In some embodiments, techniques such as flow cytometry can be used to examine the hybridization pattern of the probes.

In other embodiments, the probes can be indirectly labeled, for example, with biotin or digoxygenin, or labeled with radioactive isotopes such as $^{32}P$ and/or $^{3}H$. As a non-limiting example, a probe indirectly labeled with biotin can be detected by avidin conjugated to a detectable marker. For example, avidin can be conjugated to an enzymatic marker such as alkaline phosphatase or horseradish peroxidase. In some embodiments, enzymatic markers can be detected using colorimetric reactions using a substrate and/or a catalyst for the enzyme. In some embodiments, catalysts for alkaline phosphatase can be used, for example, 5-bromo-4-chloro-3-indolylphosphate and nitro blue tetrazolium. In some embodiments, a catalyst can be used for horseradish peroxidase, for example, diaminobenzoate.

Methods of Detecting Genetic Variations

In some embodiments, standard techniques for genotyping for the presence genetic variations, for example, amplification, can be used. Amplification of nucleic acids can be accomplished using methods known in the art. Generally, sequence information from the region of interest can be used to design oligonucleotide primers that can be identical or similar in sequence to opposite strands of a template to be amplified. In some embodiments, amplification methods can include but are not limited to, fluorescence-based techniques utilizing PCR, for example, ligase chain reaction (LCR), Nested PCR, transcription amplification, self-sustained sequence replication, nucleic acid based sequence amplification (NASBA), and multiplex ligation-dependent probe amplification (MLPA). Guidelines for selecting primers for PCR amplification are well known in the art. In some embodiments, a computer program can be used to design primers, for example, Oligo (National Biosciences, Inc., Plymouth Minn.), MacVector (Kodak/IBI), and GCG suite of sequence analysis programs.

In some embodiments, commercial methodologies available for genotyping, for example, SNP genotyping, can be used, but are not limited to, TaqMan genotyping assays (Applied Biosystems), SNPlex platforms (Applied Biosystems), gel electrophoresis, capillary electrophoresis, size exclusion chromatography, mass spectrometry, for example, MassARRAY system (Sequenom), minisequencing methods, real-time Polymerase Chain Reaction (PCR), Bio-Plex system (BioRad), CEQ and SNPstream systems (Beckman), array hybridization technology, for example, Affymetrix GeneChip (Perlegen), BeadArray Technologies, for example, Illumina GoldenGate and Infinium assays, array tag technology, Multiplex Ligation-dependent Probe Amplification (MLPA), and endonuclease-based fluorescence hybridization technology (Invader; Third Wave/Hologic). PCR can be a procedure in which target nucleic acid is amplified in a manner similar to that described in U.S. Pat. No. 4,683,195 and subsequent modifications of the procedure described therein. In some embodiments, real-time quantitative PCR can be used to determine genetic variations, wherein quantitative PCR can permit both detection and quantification of a DNA sequence in a sample, for example, as an absolute number of copies or as a relative amount when normalized to DNA input or other normalizing genes. In some embodiments, methods of quantification can include the use of fluorescent dyes that can intercalate with double-stranded DNA, and modified DNA oligonucleotide probes that can fluoresce when hybridized with a complementary DNA.

In some embodiments of the disclosure, a sample containing genomic DNA obtained from the subject can be collected and PCR can used to amplify a fragment of nucleic acid that comprises one or more genetic variations that can be indicative of a susceptibility to EN. In some embodiments, detection of genetic variations can be accomplished by expression analysis, for example, by using quantitative PCR. In some embodiments, this technique can assess the presence of an alteration in the expression or composition of one or more polypeptides or splicing variants encoded by a nucleic acid associated with EN.

In one embodiment, the DNA template of a sample from a subject containing a SNP can be amplified by PCR prior to detection with a probe. In such an embodiment, the amplified DNA serves as the template for a detection probe and, in some embodiments, an enhancer probe. Certain embodiments of the detection probe, the enhancer probe, and/or the primers used for amplification of the template by PCR can comprise the use of modified bases, for example, modified A, T, C, G, and U, wherein the use of modified bases can be useful for adjusting the melting temperature of the nucleotide probe and/or primer to the template DNA. In one embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In some embodiments, identification of genetic variations can be accomplished using hybridization methods. The presence of a specific marker allele or a particular genomic segment comprising a genetic variation, or representative of a genetic variation, can be indicated by sequence-specific hybridization of a nucleic acid probe specific for the particular allele or the genetic variation in a nucleic acid containing sample that has or has not been amplified but methods described herein. The presence of more than one specific marker allele or several genetic variations can be indicated by using two or more sequence-specific nucleic acid probes, wherein each is specific for a particular allele and/or genetic variation.

Hybridization can be performed by methods well known to the person skilled in the art, for example, hybridization techniques such as fluorescent in situ hybridization (FISH), Southern analysis, Northern analysis, or in situ hybridization. In some embodiments, hybridization refers to specific hybridization, wherein hybridization can be performed with no mismatches. Specific hybridization, if present, can be using standard methods. In some embodiments, if specific hybridization occurs between a nucleic acid probe and the nucleic acid in the sample, the sample can contain a sequence that can be complementary to a nucleotide present in the nucleic acid probe. In some embodiments, if a nucleic acid probe can contain a particular allele of a polymorphic marker, or particular alleles for a plurality of markers, specific hybridization is indicative of the nucleic acid being completely complementary to the nucleic acid probe, including the particular alleles at polymorphic markers within the probe. In some embodiments a probe can contain more than one marker allele of a particular haplotype, for example, a probe can contain alleles complementary to 2, 3, 4, 5 or all of the markers that make up a particular haplotype. In some embodiments detection of one or more particular markers of the haplotype in the sample is indicative that the source of the sample has the particular haplotype.

In some embodiments, PCR conditions and primers can be developed that amplify a product only when the variant allele is present or only when the wild type allele is present, for example, allele-specific PCR. In some embodiments of allele-specific PCR, a method utilizing a detection oligonucleotide probe comprising a fluorescent moiety or group at its 3' terminus and a quencher at its 5' terminus, and an enhancer oligonucleotide, can be employed, as described by Kutyavin et al. (*Nucleic Acid. Res.*, 34:e128 (2006)).

An allele-specific primer/probe can be an oligonucleotide that is specific for particular a polymorphism can be prepared using standard methods. In some embodiments, allele-specific oligonucleotide probes can specifically hybridize to a nucleic acid region that contains a genetic variation. In some embodiments, hybridization conditions can be selected such that a nucleic acid probe can specifically bind to the sequence of interest, for example, the variant nucleic acid sequence.

In some embodiments, allele-specific restriction digest analysis can be used to detect the existence of a polymorphic variant of a polymorphism, if alternate polymorphic variants of the polymorphism can result in the creation or elimination of a restriction site. Allele-specific restriction digests can be performed, for example, with the particular restriction enzyme that can differentiate the alleles. In some embodiments, PCR can be used to amplify a region comprising the polymorphic site, and restriction fragment length polymorphism analysis can be conducted. In some embodiments, for sequence variants that do not alter a common restriction site, mutagenic primers can be designed that can introduce one or more restriction sites when the variant allele is present or when the wild type allele is present.

In some embodiments, fluorescence polarization template-directed dye-terminator incorporation (FP-TDI) can be used to determine which of multiple polymorphic variants of a polymorphism can be present in a subject. Unlike the use of allele-specific probes or primers, this method can employ primers that can terminate adjacent to a polymorphic site, so that extension of the primer by a single nucleotide can result in incorporation of a nucleotide complementary to the polymorphic variant at the polymorphic site.

In some embodiments. DNA containing an amplified portion can be dot-blotted, using standard methods and the blot contacted with the oligonucleotide probe. The presence of specific hybridization of the probe to the DNA can then be detected. The methods can include determining the genotype of a subject with respect to both copies of the polymorphic site present in the genome, wherein if multiple polymorphic variants exist at a site, this can be appropriately indicated by specifying which variants are present in a subject. Any of the detection means described herein can be used to determine the genotype of a subject with respect to one or both copies of the polymorphism present in the subject's genome.

In some embodiments, a peptide nucleic acid (PNA) probe can be used in addition to, or instead of, a nucleic acid probe in the methods described herein. A PNA can be a DNA mimic having a peptide-like, inorganic backbone, for example, N-(2-aminoethyl) glycine units with an organic base (A, G. C, T or U) attached to the glycine nitrogen via a methylene carbonyl linker.

Nucleic acid sequence analysis can also be used to detect genetic variations, for example, genetic variations can be detected by sequencing exons, introns, 5' untranslated sequences, or 3' untranslated sequences. One or more methods of nucleic acid analysis that are available to those skilled in the art can be used to detect genetic variations, including but not limited to, direct manual sequencing, automated fluorescent sequencing, single-stranded conformation polymorphism assays (SSCP): clamped denaturing gel electrophoresis (CDGE); denaturing gradient gel electrophoresis (DGGE), two-dimensional gel electrophoresis (2DGE or TDGE); conformational sensitive gel electrophoresis (CSGE); denaturing high performance liquid chromatography (DHPLC), infrared matrix-assisted laser desorption/ionization (IR-MALDI) mass spectrometry, mobility shift analysis, quantitative real-time PCR, restriction enzyme analysis, heteroduplex analysis; chemical mismatch cleavage (CMC), RNase protection assays, use of polypeptides that recognize nucleotide mismatches, allele-specific PCR, real-time pyrophosphate DNA sequencing, PCR amplification in combination with denaturing high performance liquid chromatography (dHPLC), and combinations of such methods.

Sequencing can be accomplished through classic Sanger sequencing methods, which are known in the art. In one embodiment sequencing can be performed using high-throughput sequencing methods some of which allow detection of a sequenced nucleotide immediately after or upon its incorporation into a growing strand, for example, detection of sequence in substantially real time or real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read (or 500-1,000 bases per read for 454).

High-throughput sequencing methods can include but are not limited to, Massively Parallel Signature Sequencing (MPSS, Lynx Therapeutics), Polony sequencing, 454 pyrosequencing, Illumina (Solexa) sequencing, SOLiD sequencing, on semiconductor sequencing, DNA nanoball sequencing. Helioscope™ single molecule sequencing, Single Molecule SMRT™ sequencing, Single Molecule real time (RNAP) sequencing, Nanopore DNA sequencing, and/or sequencing by hybridization, for example, a non-enzymatic method that uses a DNA microarray, or microfluidic Sanger sequencing.

In some embodiments, high-throughput sequencing can involve the use of technology available by Helicos BioSciences Corporation (Cambridge, Mass.) such as the Single Molecule Sequencing by Synthesis (SMSS) method. SMSS is unique because it allows for sequencing the entire human genome in up to 24 hours. This fast sequencing method also allows for detection of a SNP/nucleotide in a sequence in substantially real time or real time, Finally, SMSS is powerful because, like the MIP technology, it does not use a pre-amplification step prior to hybridization. SMSS does not use any amplification. SMSS is described in US Publication Application Nos. 20060024711; 20060024678;

20060012793; 20060012784: and 20050100932. In some embodiments, high-throughput sequencing involves the use of technology available by 454 Life Sciences, Inc. (a Roche company, Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

In some embodiments, PCR-amplified single-strand nucleic acid can be hybridized to a primer and incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) can be added sequentially. A base incorporation can be accompanied by release of pyrophosphate, which can be converted to ATP by sulfurylase, which can drive synthesis of oxyluciferin and the release of visible light. Since pyrophosphate release can be equimolar with the number of incorporated bases, the light given off can be proportional to the number of nucleotides adding in any one step. The process can repeat until the entire sequence can be determined. In some embodiments, pyrosequencing can be utilized to analyze amplicons to determine whether breakpoints are present. In some embodiments, pyrosequencing can map surrounding sequences as an internal quality control.

Pyrosequencing analysis methods are known in the art. Sequence analysis can include a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes can be performed. At any given cycle, the population of nonamers that is used can be structured such that the identity of one of its positions can be correlated with the identity of the fluorophore attached to that nonamer. To the extent that the ligase discriminates for complementarily at that queried position, the fluorescent signal can allow the inference of the identity of the base. After performing the ligation and four-color imaging, the anchor primer: nonamer complexes can be stripped and a new cycle begins. Methods to image sequence information after performing ligation are known in the art.

In some embodiments, analysis by restriction enzyme digestion can be used to detect a particular genetic variation if the genetic variation results in creation or elimination of one or more restriction sites relative to a reference sequence. In some embodiments, restriction fragment length polymorphism (RFLP) analysis can be conducted, wherein the digestion pattern of the relevant DNA fragment indicates the presence or absence of the particular genetic variation in the sample.

In some embodiments, arrays of oligonucleotide probes that can be complementary to target nucleic acid sequence segments from a subject can be used to identify genetic variations. In some embodiments, an array of oligonucleotide probes comprises an oligonucleotide array, for example, a microarray. In some embodiments, the present disclosure features arrays that include a substrate having a plurality of addressable areas, and methods of using them. At least one area of the plurality includes a nucleic acid probe that binds specifically to a sequence comprising a genetic variation, and can be used to detect the absence or presence of the genetic variation, for example, one or more SNPs, microsatellites, or CNVs, as described herein, to determine or identify an allele or genotype. For example, the array can include one or more nucleic acid probes that can be used to detect a genetic variation associated with a gene and/or product of a gene listed in FIG. 3. In some embodiments, the array can further comprise at least one area that includes a nucleic acid probe that can be used to specifically detect another marker associated with EN, as described herein.

Microarray hybridization can be performed by hybridizing a nucleic acid of interest, for example, a nucleic acid encompassing a genetic variation, with the array and detecting hybridization using nucleic acid probes. In some embodiments, the nucleic acid of interest is amplified prior to hybridization. Hybridization and detecting can be carried out according to standard methods described in Published PCT Applications: WO 92/10092 and WO 95/11995, and U.S. Pat. No. 5,424,186. For example, an array can be scanned to determine the position on the array to which the nucleic acid hybridizes. The hybridization data obtained from the scan can be, for example, in the form of fluorescence intensities as a function of location on the array.

Arrays can be formed on substrates fabricated with materials such as paper; glass; plastic, for example, polypropylene, nylon, or polystyrene; polyacrylamide: nitrocellulose; silicon; optical fiber, or any other suitable solid or semisolid support; and can be configured in a planar, for example, glass plates or silicon chips): or three dimensional, for example, pins, fibers, beads, particles, microtiter wells, and capillaries, configuration.

Methods for generating arrays are known in the art and can include for example; photolithographic methods (U.S. Pat. Nos. 5,143,854, 5,510,270 and 5,527,681); mechanical methods, for example, directed-flow methods (U.S. Pat. No. 5,384,261); pin-based methods (U.S. Pat. No. 5,288,514); bead-based techniques (PCT US/93/04145); solid phase oligonucleotide synthesis methods; or by other methods known to a person skilled in the art (see, e.g., Bier et al., *Adv. Biochem. Eng. Biotechnol.*, 109:433-53 (2008); Hoheisel, *Nat. Rev. Genet.*, 7: 200-10 (2006); Fan et al., *Methods Enzymol.*, 410:57-73 (2006); Raqoussis & Elvidge, *Expert Rev. Mol. Design*, 6: 145-52 (2006); Mockler et al., *Genomics*, 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. Nos. 6,858, 394; 6,429.027; 5,445,934; 5,700,637; 5,744,305; 5,945, 334; 6,054,270; 6,300,063; 6,733,977; 7,364.858, EP 619 321, and EP 373 203, the entire teachings of which are incorporated by reference herein. Methods for array production, hybridization, and analysis are also described in Snijders et al., *Nat. Genetics*, 29:263-264 (2001); Klein et al., *Proc. Natl. Acad. Sci. USA*, 29:4494-4499 (1999); Albertson et al., *Breast Cancer Research and Treatment*, 7:289-298 (2003); and Snijders et al., "BAC microarray based comparative genomic hybridization," in: Zhao et al. (eds), *Bacterial Artificial Chromosomes: Methods and Protocols, Methods in Molecular Biology*, Humana Press, 2002.

In some embodiments, oligonucleotide probes forming an array can be attached to a substrate by any number of techniques, including, but not limited to, in situ synthesis, for example, high-density oligonucleotide arrays, using photolithographic techniques: spotting/printing a medium to low density on glass, nylon, or nitrocellulose; by masking: and by dot-blotting on a nylon or nitrocellulose hybridization membrane. In some embodiments, oligonucleotides can be immobilized via a linker, including but not limited to, by covalent, ionic, or physical linkage. Linkers for immobilizing nucleic acids and polypeptides, including reversible or cleavable linkers, are known in the art (U.S. Pat. No. 5,451,683 and WO98/20019). In some embodiments, oligonucleotides can be non-covalently immobilized on a substrate by hybridization to anchors, by means of magnetic beads, or in a fluid phase, for example, in wells or capillaries.

An array can comprise oligonucleotide hybridization probes capable of specifically hybridizing to different genetic variations. In some embodiments, oligonucleotide arrays can comprise a plurality of different oligonucleotide probes coupled to a surface of a substrate in different known locations. In some embodiments, oligonucleotide probes can exhibit differential or selective binding to polymorphic sites, and can be readily be designed by one of ordinary skill in the art, for example, an oligonucleotide that is perfectly complementary to a sequence that encompasses a polymorphic site, for example, a sequence that includes the polymorphic site, within it, or at one end, can hybridize preferentially to a nucleic acid comprising that sequence, as opposed to a nucleic acid comprising an alternate polymorphic variant.

In some embodiments, arrays can include multiple detection blocks, for example, multiple groups of probes designed for detection of particular polymorphisms. In some embodiments, these arrays can be used to analyze multiple different polymorphisms. In some embodiments, detection blocks can be grouped within a single array or in multiple, separate arrays, wherein varying conditions, for example, conditions optimized for particular polymorphisms, can be used during hybridization. General descriptions of using oligonucleotide arrays for detection of polymorphisms can be found, for example, in U.S. Pat. Nos. 5,858,659 and 5,837,832. In addition to oligonucleotide arrays, cDNA arrays can be used similarly in certain embodiments.

The methods described herein can include but are not limited to providing an array as described herein; contacting the array with a sample, and detecting binding of a nucleic acid from the sample to the array. In some embodiments, the method can comprise amplifying nucleic acid from the sample, for example, a region associated with EN or a region that includes another region associated with EN. In some embodiments, the methods described herein can include using an array that can identify differential expression patterns or copy numbers of one or more genes in samples from control and affected individuals. For example, arrays of probes to a marker described herein can be used to identify genetic variations between DNA from an affected subject, and control DNA obtained from an individual that does not have EN. Since the nucleotides on the array can contain sequence tags, their positions on the array can be accurately known relative to the genomic sequence.

In some embodiments, it can be desirable to employ methods that can detect the presence of multiple genetic variations, for example, polymorphic variants at a plurality of polymorphic sites, in parallel or substantially simultaneously. In some embodiments, these methods can comprise oligonucleotide arrays and other methods, including methods in which reactions, for example, amplification and hybridization, can be performed in individual vessels, for example, within individual wells of a multi-well plate or other vessel.

Determining the identity of a genetic variation can also include or consist of reviewing a subject's medical history, where the medical history includes information regarding the identity, copy number, presence or absence of one or more alleles or SNPs in the subject, e.g., results of a genetic test.

Genetic variations can also be identified using any of a number of methods well known in the art. For example, genetic variations available in public databases, which can be searched using methods and custom algorithms or algorithms known in the art, can be used. In some embodiments, a reference sequence can be from, for example, the human draft genome sequence, publicly available in various databases, or a sequence deposited in a database such as GenBank.

Methods of Detecting CNVs

Detection of genetic variations, specifically CNVs, can be accomplished by one or more suitable techniques described herein. Generally, techniques that can selectively determine whether a particular chromosomal segment is present or absent in an individual can be used for genotyping CNVs. Identification of novel copy number variations can be done by methods for assessing genomic copy number changes.

In some embodiments, methods include but are not limited to, methods that can quantitatively estimate the number of copies of a particular genomic segment, but can also include methods that indicate whether a particular segment is present in a sample or not. In some embodiments, the technique to be used can quantify the amount of segment present, for example, determining whether a DNA segment is deleted, duplicated, or triplicated in subject, for example, Fluorescent In Situ Hybridization (FISH) techniques, and other methods described herein.

In some embodiments, other genotyping technologies can be used for detection of CNVs, including but not limited to, karyotype analysis, Molecular Inversion Probe array technology, for example, Affymetrix SNP Array 6.0, and BeadArray Technologies, for example, Illumina GoldenGate and Infinium assays, as can other platforms such as NimbleGen HD2.1 or HD4.2, High-Definition Comparative Genomic Hybridization (CGH) arrays (Agilent Technologies), tiling array technology (Affymetrix), multiplex ligation-dependent probe amplification (MLPA), Invader assay, qPCR, or fluorescence in situ hybridization. In one embodiment, Array Comparative Genomic Hybridization (aCGH) methods can be used. As described herein, karyotype analysis can be a method to determine the content and structure of chromosomes in a sample. In some embodiments, karyotyping can be used, in lieu of aCGH, to detect translocations, which can be copy number neutral (balanced translocations), and therefore, not detectable by aCGH. Information about amplitude of particular probes, which can be representative of particular alleles, can provide quantitative dosage information for the particular allele, and by consequence, dosage information about the CNV in question, since the marker can be selected as a marker representative of the CNV and can be located within the CNV. In some embodiments, if the CNV is a deletion, the absence of particular marker allele is representative of the deletion. In some embodiments, if the CNV is a duplication or a higher order copy number variation, the signal intensity representative of the allele correlating with the CNV can represent the copy number. A summary of methodologies commonly used is provided in Perkel (*J. Nature Methods*, 5:447-453 (2008)).

PCR assays can be utilized to detect CNVs and can provide an alternative to array analysis. In particular, PCR assays can enable detection of precise boundaries of gene/chromosome variants, at the molecular level, and which boundaries are identical in different individuals. PCR assays can be based on the amplification of a junction fragment present only in individuals that carry a deletion. This assay can convert the detection of a loss by array CGH to one of a gain by PCR.

Examples of PCR techniques that can be used in the present disclosure include, but are not limited to quantitative PCR, real-time quantitative PCR (qPCR), quantitative fluorescent PCR (QF-PCR), multiplex fluorescent PCR (MF-PCR), real time PCR (RT-PCR), single cell PCR, PCR-RFLP/RT-PCR-RFLP, hot start PCR and Nested PCR. Other suitable amplification methods include the ligase chain reaction (LCR), ligation mediated PCR (LM-PCR), degenerate oligonucleotide probe PCR (DOP-PCR), transcription amplification, self-sustained sequence replication, selective amplification of target polynucleotide sequences, consensus sequence primed polymerase chain reaction (CP-PCR), arbitrarily primed polymerase chain reaction (AP-PCR) and nucleic acid based sequence amplification (NABSA).

Alternative methods for the simultaneous interrogation of multiple regions include quantitative multiplex PCR of short fluorescent fragments (QMPSF), multiplex amplifiable probe hybridization (MAPH) and multiplex ligation-dependent probe amplification (MLPA), in which copy-number differences for up to 40 regions can be scored in one experiment. Another approach can be to specifically target regions that harbor known segmental duplications, which are often sites of copy-number variation. By targeting the variable nucleotides between two copies of a segmental duplication (called paralogous sequence variants) using a SNP-genotyping method that provides independent fluorescence intensities for the two alleles, it is possible to detect an increase in intensity of one allele compared with the other.

In some embodiments, the amplified piece of DNA can be bound to beads using the sequencing element of the nucleic acid tag under conditions that favor a single amplified piece of DNA molecule to bind a different bead and amplification occurs on each bead. In some embodiments, such amplification can occur by PCR. Each bead can be placed in a separate well, which can be a picoliter-sized well. In some embodiments each bead is captured within a droplet of a PCR-reaction-mixture-in-oil-emulsion and PCR amplification occurs within each droplet. The amplification on the bead results in each bead carrying at least one million, at least 5 million, or at least 10 million copies of the single amplified piece of DNA molecule.

In some embodiments where PCR occurs in oil-emulsion mixtures, the emulsion droplets are broken, the DNA is denatured and the beads carrying single-stranded nucleic acids clones are deposited into a well, such as a picoliter-sized well, for further analysis according to the methods described herein. These amplification methods allow for the analysis of genomic DNA regions. Methods for using bead amplification followed by fiber optics detection are described in Margulies et al., Nature, 1:437(7057):376-80 (2005), and as well as in US Publication Application Nos. 20020012930; 20030068629; 20030100102; 20030148344; 20040248161; 20050079510, 20050124022; and 20060078909.

Another variation on the array-based approach can be to use the hybridization signal intensities that are obtained from the oligonucleotides employed on Affymetrix SNP arrays or in Illumina Bead Arrays. Here hybridization intensities are compared with average values that are derived from controls, such that deviations from these averages indicate a change in copy number. As well as providing information about copy number, SNP arrays have the added advantage of providing genotype information. For example, they can reveal loss of heterozygosity, which could provide supporting evidence for the presence of a deletion, or might indicate segmental uniparental disomy (which can recapitulate the effects of structural variation in some genomic regions—Prader-Willi and Angelman syndromes, for example).

Many of the basic procedures followed in microarray-based genome profiling are similar, if not identical, to those followed in expression profiling and SNP analysis, including the use of specialized microarray equipment and data-analysis tools. Since microarray-based expression profiling has been well established in the last decade, much can be learned from the technical advances made in this area. Examples of the use of microarrays in nucleic acid analysis that can be used are described in U.S. Pat. Nos. 6,300,063, 5,837,832, 6,969,589, 6,040,138, 6,858,412, U.S. application Ser. No. 08/529,115, U.S. application Ser. No. 10/272,384, U.S. application Ser. No. 10/045,575. U.S. application Ser. No. 10/264,571 and U.S. application Ser. No. 10/264,574. It should be noted that there are also distinct differences such as target and probe complexity, stability of DNA over RNA, the presence of repetitive DNA and the need to identify single copy number alterations in genome profiling.

In one embodiment, the genetic variations detected comprise CNVs and may be detected using array CGH. In some embodiments, array CGH can be been implemented using a wide variety of techniques. The initial approaches used arrays produced from large-insert genomic clones such as bacterial artificial chromosomes (BACs). Producing sufficient BAC DNA of adequate purity to make arrays is arduous, so several techniques to amplify small amounts of starting material have been employed. These techniques include ligation-mediated PCR (Snijders et al, Nat. Genet., 29:263-64), degenerate primer PCR using one or several sets of primers, and rolling circle amplification. BAC arrays that provide complete genome tiling paths are also available. Arrays made from less complex nucleic acids such as cDNAs, selected PCR products, and oligonucleotides can also be used. Although most CGH procedures employ hybridization with total genomic DNA, it is possible to use reduced complexity representations of the genome produced by PCR techniques. Computational analysis of the genome sequence can be used to design array elements complementary to the sequences contained in the representation. Various SNP genotyping platforms, some of which use reduced complexity genomic representations, can be useful for their ability to determine both DNA copy number and allelic content across the genome. In some embodiments, small amounts of genomic DNA can be amplified with a variety of whole genome amplification methods prior to CGH analysis of the sample.

The different basic approaches to array CGH provide different levels of performance, so some are more suitable for particular applications than others. The factors that determine performance include the magnitudes of the copy number changes, their genomic extents, the state and composition of the specimen, how much material is available for analysis, and how the results of the analysis can be used. Many applications use reliable detection of copy number changes of much less than 50%, a higher stringency than for other microarray technologies. Note that technical details are extremely important and different implementations of methods using the same array CGH approach can yield different levels of performance. Various CGH methods are known in the art and are equally applicable to one or more methods of the present disclosure. For example, CGH methods are disclosed in U.S. Pat. Nos. 7,957,913, 7,910,353, 7,238,484, 7,702,468, 7,034,144; 7,030,231; 7,011,949;

7,014,997; 6,977,148; 6,951,761; and 6,916,621, the disclosure from each of which is incorporated by reference herein in its entirety.

The data provided by array CGH are quantitative measures of DNA sequence dosage. Array CGH provides high-resolution estimates of copy number aberrations, and can be performed efficiently on many samples. The advent of array CGH technology makes it possible to monitor DNA copy number changes on a genomic scale and many projects have been launched for studying the genome in specific diseases.

In one embodiment, whole genome array-based comparative genome hybridization (array CGH) analysis, or array CGH on a subset of genomic regions, can be used to efficiently interrogate human genomes for genomic imbalances at multiple loci within a single assay. The development of comparative genomic hybridization (CGH) (Kallioniemi et al, 1992, Science 258: 818-21) provided the first efficient approach to scanning entire genomes for variations in DNA copy number. The importance of normal copy number variation involving large segments of DNA has been unappreciated. Array CGH is a breakthrough technique in human genetics, which is attracting interest from clinicians working in fields as diverse as cancer and IVF (In Vitro Fertilization). The use of CGH microarrays in the clinic holds great promise for identifying regions of genomic imbalance associated with disease. Advances from identifying chromosomal critical regions associated with specific phenotypes to identifying the specific dosage sensitive genes can lead to therapeutic opportunities of benefit to patients. Array CGH is a specific, sensitive and rapid technique that can enable the screening of the whole genome in a single test. It can facilitate and accelerate the screening process in human genetics and is expected to have a profound impact on the screening and counseling of patients with genetic disorders. It is now possible to identify the exact location on the chromosome where an aberration has occurred and it is possible to map these changes directly onto the genomic sequence.

An array CGH approach provides a robust method for carrying out a genome-wide scan to find novel copy number variants (CNVs). The array CGH methods can use labeled fragments from a genome of interest, which can be competitively hybridized with a second differentially labeled genome to arrays that are spotted with cloned DNA fragments, revealing copy-number differences between the two genomes. Genomic clones (for example, BACs), cDNAs, PCR products and oligonucleotides, can all be used as array targets. The use of array CGH with BACs was one of the earliest employed methods and is popular, owing to the extensive coverage of the genome it provides, the availability of reliable mapping data and ready access to clones. The last of these factors is important both for the array experiments themselves, and for confirmatory FISH experiments.

In a typical CGH measurement, total genomic DNA is isolated from test and reference subjects, differentially labeled, and hybridized to a representation of the genome that allows the binding of sequences at different genomic locations to be distinguished. More than two genomes can be compared simultaneously with suitable labels. Hybridization of highly repetitive sequences is typically suppressed by the inclusion of unlabeled Cot-1 DNA in the reaction. The relative hybridization intensity of the test and reference signals at a given location can be proportional to the relative copy number of those sequences in the test and reference genomes. If the reference genome is normal then increases and decreases in signal intensity ratios directly indicate DNA copy number variation within the test genome. Data are typically normalized so that the modal ratio for the genome is set to some standard value, typically 1.0 on a linear scale or 0.0 on a logarithmic scale. Additional measurements such as FISH or flow cytometry can be used to determine the actual copy number associated with a ratio level.

In some embodiments, an array CGH procedure can include the following steps. First, large-insert clones, for example, BACs can be obtained from a supplier of clone libraries. Then, small amounts of clone DNA can be amplified, for example, by degenerate oligonucleotide-primed (DOP) PCR or ligation-mediated PCR in order to obtain sufficient quantities needed for spotting. Next, PCR products can be spotted onto glass slides using, for example, microarray robots equipped with high-precision printing pins. Depending on the number of clones to be spotted and the space available on the microarray slide, clones can either be spotted once per array or in replicate. Repeated spotting of the same clone on an array can increase precision of the measurements if the spot intensities are averaged, and allows for a detailed statistical analysis of the quality of the experiments. Subject and control DNAs can be labeled, for example, with either Cy3 or Cy5-dUTP using random priming and can be subsequently hybridized onto the microarray in a solution containing an excess of Cot1-DNA to block repetitive sequences. Hybridizations can either be performed manually under a coverslip, in a gasket with gentle rocking or, automatically using commercially available hybridization stations. These automated hybridization stations can allow for an active hybridization process, thereby improving the reproducibility as well as reducing the actual hybridization time, which increases throughput. The hybridized DNAs can detected through the two different fluorochromes using standard microarray scanning equipment with either a scanning confocal laser or a charge coupled device (CCD) camera-based reader, followed by spot identification using commercially or freely available software packages.

The use of CGH with arrays that comprise long oligonucleotides (60-100 bp) can improve the detection resolution (in some embodiments, as small as about 3-5 kb sized CNVs on arrays designed for interrogation of human whole genomes) over that achieved using BACs (limited to 50-100 kb or larger sized CNVs due to the large size of BAC clones). In some embodiments, the resolution of oligonucleotide CGH arrays is achieved via in situ synthesis of 1-4 million unique features/probes per microarray, which can include microarrays available from Roche NimbleGen and Agilent Technologies. In addition to array CGH methods for copy number detection, other embodiments for partial or whole genome analysis of CNVs within a genome include, but are not limited to, use of SNP genotyping microarrays and sequencing methods.

Another method for copy number detection that uses oligonucleotides can be representational oligonucleotide microarray analysis (ROMA). It is similar to that applied in the use of BAC and CGH arrays, but to increase the signal-to-noise ratio, the 'complexity' of the input DNA is reduced by a method called representation or whole-genome sampling. Here the DNA that is to be hybridized to the array can be treated by restriction digestion and then ligated to adapters, which results in the PCR-based amplification of fragments in a specific size-range. As a result, the amplified DNA can make up a fraction of the entire genomic sequence—that is, it is a representation of the input DNA that has significantly reduced complexity, which can lead to a reduction in background noise. Other suitable methods available to the skilled person can also be used, and are within scope of the present disclosure.

A comparison of one or more genomes relative to one or more other genomes with array CGH, or a variety of other CNV detection methods, can reveal the set of CNVs between two genomes, between one genome in comparison to multiple genomes, or between one set of genomes in comparison to another set of genomes. In some embodiments, an array CGH experiment can be performed by hybridizing a single test genome against a pooled sample of two or more genomes, which can result in minimizing the detection of higher frequency variants in the experiment. In some embodiments, a test genome can be hybridized alone (e.g., one-color detection) to a microarray, for example, using array CGH or SNP genotyping methods, and the comparison step to one or more reference genomes can be performed in silico to reveal the set of CNVs in the test genome relative to the one or more reference genomes. In one embodiment, a single test genome is compared to a single reference genome in a 2-color experiment wherein both genomes are cohybridized to the microarray.

Array CGH can be used to identify genes that are causative or associated with a particular phenotype, condition, or disease by comparing the set of CNVs found in the affected cohort to the set of CNVs found in an unaffected cohort. An unaffected cohort may consist of any individual unaffected by the phenotype, condition, or disease of interest, but in one embodiment is comprised of individuals or subjects that are apparently healthy (normal). Methods employed for such analyses are described in U.S. Pat. Nos. 7,702,468, 7,957, 913 and 8,862,410. In some embodiments of CNV comparison methods, candidate genes that are causative or associated (i.e., potentially serving as a biomarker) with a phenotype, condition, or disease will be identified by CNVs that occur in the affected cohort but not in the unaffected cohort, or present at much lower frequency in the unaffected cohort as compared to the affected cohort. In another embodiment of CNV comparison methods, one or more CNVs may be present at much higher frequency in the unaffected cohort as compared to the affected cohort and thus may be indicative of protection for development of the disease or condition present in the affected cohort. In some embodiments of CNV comparison methods, candidate genes that are causative or associated (i.e., potentially serving as a biomarker) with a phenotype, condition, or disease will be identified by CNVs that occur at a statistically significant higher frequency in the affected cohort as compared their frequency in the unaffected cohort. Thus, CNVs detected in the affected cohort as compared to the unaffected cohort can serve as beacons of genes that are causative or associated with a particular phenotype, condition, or disease. In some embodiments, CNV detection and comparison methods can result in direct identification of the gene that is causative or associated with phenotype, condition, or disease if the CNVs are found to overlap with or encompass the gene(s). In some embodiments. CNV detection and comparison methods can result in identification of regulatory regions of the genome (e.g., promoters, enhancers, transcription factor binding sites) that regulate the expression of one or more genes that are causative or associated with the phenotype, condition, or disease of interest.

Due to the large amount of genetic variation between any two genomes, or two sets (cohorts) of genomes, being compared, one embodiment is to reduce the genetic variation search space by interrogating only CNVs, as opposed to the full set of genetic variants that can be identified in an individual's genome or exome. The set of CNVs that occur only, or at a statistically higher frequency, in the affected cohort as compared to the unaffected cohort can then be further investigated in targeted sequencing experiments to reveal the full set of genetic variants (of any size or type) that are causative or associated (e.g., potentially serving as a biomarker) with a phenotype, condition, or disease. It can be appreciated by those skilled in the art that the targeted sequencing experiments can be performed in both the affected and unaffected cohorts in order to identify the genetic variants (e.g., SNVs and indels) that occur only, or at a statistically significant higher frequency, in the affected individual or cohort as compared to the unaffected cohort. In another embodiment, the targeted sequencing experiments can be performed on the affected cohort and the variations found can be compared to public or private databases containing sequence variants present in unaffected subjects, or in some embodiments, the general population.

When investigating EN, it can be appreciated by those skilled in the art that the number of EN candidate genes (or regulatory sequences) identified via CNV (or other variant types) detection methods may increase or decrease when additional EN cohorts are analyzed. Similarly, the number of EN candidate genes (or regulatory sequences), for example, identified via CNV (or other variant types) detection methods may increase or decrease when additional unaffected cohorts are used to interpret the affected cohort CNVs (or other variat types). For very rare CNVs (e.g., <0.1% frequency in the general population), only a single case may be observed in a given EN cohort (e.g., 100 cases) but further statistical significance or evidence for the gene (or regulatory sequence/locus in the genome) can be established by: 1) CNV analysis of additional EN cohorts, 2) CNV analysis of additional Normal cohorts, 3) targeted gene sequencing of both EN and Normal cohorts, and/or 4) functional characterization of the EN candidate gene (e.g., in silico analysis of the predicted impact of the candidate mutation on the gene product, RNAi knockdown experiments, biochemical assays on EN patient tissue, gene expression analysis of disease-relevant tissues or of induced pluripotent stem cells (iPSCs) created from the EN patient(s) harboring the candidate EN-causing genetic variant). It can be appreciated by those skilled in the art that the ability to identify disease genes via rare CNVs in as few as 100-300 cases, the typical size of a Phase 2 clinical trial, has particular utility for the identification of genetic biomarkers of drug efficacy and/or safety and advantages over SNV-based discovery methods, which typically require thousands of cases. Genes identified by rare loss-of-function CNVs can then be sequenced in the Phase 2 clinical trial cohort (or, via targeted interpretation of previously obtained exome and/or whole genome sequences on the clinical trial cohort) to reveal genetic biomarkers. Knowledge of genetic biomarkers for safety and/or efficacy in Phase 2 can substantially reduce the attrition rate and costs of drug development.

It can be appreciated by those skilled in the art that a candidate gene may validate as causative of the phenotype, condition, or disease (e.g., EN), which may, for example, be confirmed via mechanism of action experiments, or it may serve as a biomarker of the phenotype, condition, or disease. Thus, in the example of EN, in some embodiments, the EN-specific gene (or regulatory sequence/locus) may be a biomarker of age-of-onset for EN and disease severity, and thus have diagnostic utility for monitoring patients known to be at risk for EN or as a general screening test in the population for early diagnosis of the disease. In some embodiments, the EN-specific gene/biomarker may be an indicator of drug response (e.g., a particular subtype of EN may respond best to a therapeutic targeting a particular phenotype, causative gene, or other gene in the same pathway as the causative gene) and thus have utility during drug development in clinical trials. For example, clinical trials for a therapeutic that targets a EN genetic subtype comprising only 10% of all patients exhibiting symptoms of EN, can be designed to comprise only those 10% of patients with a specific genotype(s) in order to reduce the time and cost of such clinical trials (e.g., smaller number of patients in the clinical trial). It can be appreciated by those skilled in the art that such patient stratification methods (i.e., specific genotypes correlated with the disease or drug response) can be employed not only for targeted therapeutics, but in general for any drug that is approved or in development (i.e., the mechanism of action may or may not be known). For example, drugs in development or approved to treat, for example, cancer, may have utility in being repurposed to treat EN. Such patient stratification methods can also be utilized to develop a companion diagnostic test (e.g., comprising the specific genes/genotypes found in patients that are indicative of drug response) for a particular drug, either concurrently during the clinical trials for the drug or after drug approval (e.g., as a new indication or for the physician to use in guiding medical decisions for the patient).

Figure 9:
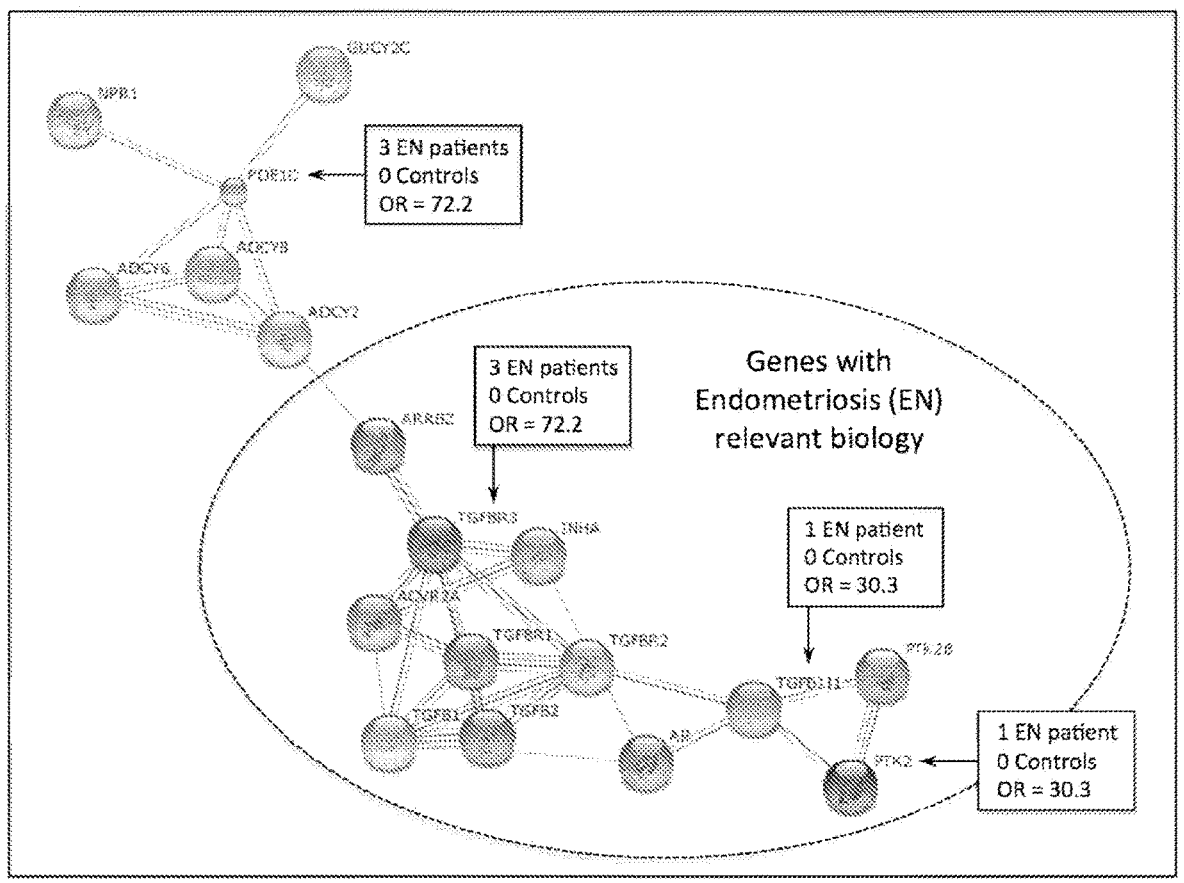
FIG. 9 shows molecular interactions on the basis of biochemical and in silico evidence generated with the String 9.05 algorithm (http://string-db.org/). Four genes (PDE1C, PTK2, TGFBR3, TBFB1I1) that were identified on the basis of CNVs present in 1-3 EN patients and 0 controls are indicated along with OR values. Genes with EN-relevant biology are encircled.

Further links to EN pathology may be established via pathway analysis of the genes, which may take into consideration binding interactions (e.g., via yeast 2-hybrid screen) and molecular events (e.g., kinase activity or other enzymatic processes) if such information is available for the gene(s) of interest (e.g., specified in the analysis). Both commercial (e.g., Ingenuity's IPA software and Thomson Reuter's GeneGo software) and open source software (e.g., String: string-db.org/) are available for such analyses. To assess connections to established EN biology, analyses can be performed for the set of candidate EN genes independently or against known causative EN genes singly or as a group. For example, see FIG. 9.

A method of screening a subject for a disease or disorder can comprise assaying a nucleic acid sample from the subject to detect sequence information for more than one genetic loci and comparing the sequence information to a panel of nucleic acid biomarkers and screening the subject for the presence or absence of EN if one or more of low frequency biomarkers in the panel are present in the sequence information. The panel may comprise at least one nucleic acid biomarker for each of the more than one genetic loci. For example, the panel can comprise 2, 3, 4, 5, 6, 7, 8, 9, 10, 15, 20, 25, 30, 35, 40, 45, 50, 75, 100, 150, 200 or more nucleic acid biomarkers for each of the more than one genetic loci. The panel may comprise at least 25 low frequency biomarkers. For example, the panel can comprise at least 30, 35, 40, 45, 50, 55, 60, 65, 70, 75, 80, 85, 90, 95, 100, 135, 150, 175, 200, 250, 500, or 1000 or more low frequency biomarkers. A low frequency biomarker can occur at a frequency of 0.1% or less in a population of subjects without a diagnosis of the disease or disorder. For example, a low frequency biomarker can occur at a frequency of 0.05%, 0.01%, 0.005%, 0.001%, 0.0005%, 0.0001%, 0,00005%, or 0.00001% or less in a population of subjects without a diagnosis of the disease or disorder.

In some embodiments, the presence or absence of EN in the subject can be determined with at least 50% confidence. For example, the presence or absence of the disease or disorder in the subject can be determined with at least 50%, 55%, 60%, 65%, 70%, 75%, 80%, 85%, 90%, 95%, 98%, 99%, or 100% confidence.

In one embodiment, EN candidate CNV subregions and genes associated with these regions may be determined or identified by comparing genetic data from a cohort of normal individuals (NVE) to that of a cohort of individuals known to have, or be susceptible to EN.

In some embodiments, genomic DNA samples from individuals within a NVE cohort and/or a EN cohort can be considered test subject DNA samples and hybridized against one or more, sex-matched reference DNA samples from individuals. For example, reference DNA samples can be labeled with a fluorophore such as Cy5, using methods described herein, and test subject DNA samples can be labeled with a different fluorophore, such as Cy3. After labeling, samples can be combined and can be co-hybridized to a microarray and analyzed using any of the methods described herein, such as aCGH. Arrays can then be scanned and the data can be analyzed with software, Genetic alterations, such as CNVs, can be called using any of the methods described herein. A list of the genetic alterations, such as CNVs, can be generated for each cohort. The list of CNVs can be used to generate a master list of non-redundant CNVs and/or CNV subregions for each cohort. The list can be based on the presence or absence of the CNV subregion in individuals within the cohort. In this manner, the master list can contain a number of distinct CNV subregions, some of which are uniquely present in a single individual and some of which are present in multiple individuals.

In some embodiments, CNV subregions of interest may be obtained by annotation of each CNV subregion with relevant information, such as overlap with known genes and/or exons. In some embodiments, CNV subregions of interest can be obtained by calculating the OR for a CNV subregion according to the following formula: OR=(EN/((# individuals in EN cohort)−EN))/(NVE/((# individuals in NVE cohort)−NVE)), where: EN=number of EN individuals with a CNV subregion of interest and NVE=number of NVE individuals with the CNV subregion of interest. If NVE=0, it can be set to 1 to avoid dealing with infinities in cases where no CNVs are seen in the NVE.

The number of individuals in any given cohort may be at least about 10, 50, 100, 200, 300, 400, 500, 600, 700, 800, 900, 1000, 2500, 5000, 7500, 10,000, 100,000, or more.

In some embodiments, a CNV subregion/gene can be of interest if the CNV subregion overlaps a known gene, and is associated with an OR of at least 6, e.g., at least 35. For example, a CNV subregion/gene can be of interest if the CNV subregion overlaps a known gene, and is associated with an OR of at least 7, 8, 9, 10, 12, 14, 16, 18, 20, 25, 30, 35, 40, 45, 50, or more. In some embodiments, a CNV subregion/gene can be of interest if the CNV subregion overlaps a known gene, and is associated with an OR from about 6-100, 6-50, 6-40, 6-30, 6-20, 6-10, 6-9, 6-8, 6-7, 8-100, 8-50, 8-40, 8-30, 8-20, 8-10, 10-100, 10-50, 10-40, 10-30, 10-20, 20-100, 20-50, 20-40, 20-30, 30-100, 30-50, 30-40, 40-100, 40-50, 50-100, or 5-7. The CNV subregion/gene can be an exonic or intronic part of the gene, or both.

In some embodiments, a CNV subregion/gene can be of interest if the CNV subregion does not overlap a known gene (e.g., is non-genic or intergenic) and is associated with an OR of at least 4 or higher. For example, a CNV subregion/gene can be of interest if the CNV subregion does not overlap a known gene (e.g., is non-genic or intergenic) and is associated with an OR of at least 5, 6, 7, 9, 9, 10, 12, 14, 16, 18, 20, 25, 30, 35, 40, 45, 50, or more. In some embodiments, a CNV subregion/gene can be of interest if the CNV subregion does not overlap a known gene (e.g., is non-genic or intergenic) and is associated with an OR from about 5-100, 5-50, 5-40, 5-30, 5-20, 20-100, 20-50, 20-40, 20-30, 30-100, 30-50, 30-40, 40-100, 40-50, 50-100, or 9-11.

In some embodiments, a CNV subregion/gene can be of interest based on the OR associated with the sum of EN cases and the sum of NVE cases affecting the same gene (including distinct CNV subregions). For example, a CNV subregion/gene can be of interest if the OR associated with the sum of EN cases and the sum of NVE cases affecting the same gene (including distinct CNV subregions) is at least 4, 5, 6, 7, 8, 9, 10, 12, 14, 16, 18, 20, 25, 30, 35, 40, 45, 50, or more. In some embodiments, a CNV subregion/gene can be of interest if the OR associated with the sum of EN cases and the sum of NVE cases affecting the same gene (including distinct CNV subregions) is from about 4-100, 4-50, 4-40, 4-30, 4-20, 4-10, 4-9, 4-8, 4-7, 8-100, 8-50, 8-40, 8-30, 8-20, 8-10, 10-100, 10-50, 10-40, 10-30, 10-20, 20-100, 20-50, 20-40, 20-30, 30-100, 30-50, 30-40, 40-100, 40-50, 50-100, or 5-7.

The data presented in FIGS. 1-4 were generated on the basis of a comparison of copy number variants (CNVs) identified in a NVE and a EN cohort. CNV genome locations are provided using the Human March 2006 (NCBI36/hg18) assembly. It can be appreciated by those skilled in the art that a CNV found in an affected individual may have one or more subregions that are found in the affected cohort as compared to the unaffected cohort and, similarly, other subregions within the CNV that are found at comparable frequencies, or not statistically significant different frequencies, in the affected and unaffected cohorts. In one embodiment. CNV detection and analysis methods are employed that enable comparison of CNV subregions to facilitate identification of genes (or regulatory loci) that are causative or associated with the phenotype, condition, or disease being investigated (or detected for diagnostic purposes).

FIG. 1 lists exemplary CNVs associated with EN, obtained as described in Example 1. For each entry, the chromosome (for the purpose of algorithms and databases used in the analyses, chromosome X is designated as chromosome 23) and original CNV start and stop positions are listed, along with original CNV size. CNV type (loss or gain), EN case ID, gene annotation (for the CNV subregion not the original CNV) and corresponding SEQ ID numbers (Nos.).

FIG. 2 shows the actual CNV subregions found to be unique or significantly different between the EN and NVE cohorts. For each entry, the chromosome (for the purpose of algorithms and databases used in the analyses, chromosome X is designated as chromosome 23) and CNV subregion start and stop positions are listed, along with CNV subregion size, CNV type (loss or gain), EN case ID, gene annotation, whether a genic CNV subregion of interest overlaps an exon or not, the number of NVE subjects and the number of EN subjects that harbor the relevant CNV subregion, the Fisher's 2 tailed Exact Test (FET), Odds ratio (OR), and the category under which the CNV subregion was identified.

FIG. 3 represents a non-redundant list for all genes listed in FIG. 2 (namely, those relevant to CNV subregions of interest), and includes RefSeq Gene Symbol, Exon overlap (intronic, exonic or both). NCBI Gene ID (DNA accession number), Gene Description (brief gene description), and RefSeq Summary (summary of gene function).

FIG. 4 represents a non-redundant list for all genes listed in FIG. 2 (namely, those relevant to CNV subregions of interest) and includes RefSeq Gene Symbol, Exon overlap (intronic, exonic or both), RefSeq Accession Number (may be multiple entries per gene), mRNA Description (brief description of mRNA), and corresponding SEQ ID Nos.

More than one RNA product (e.g., alternatively spliced mRNA transcripts and non-coding RNAs) can be produced from a single gene. FIG. 4 lists all presently known transcript variants (and their RNA accession numbers) but new variants may be found when further studies are completed and that generation of these additional transcript variants (and ultimately protein and/or regulatory RNA products) may also be impacted by one or more CNVs or CNV subregions listed in FIGS. 1 and 2, respectively. The transcripts listed in FIG. 4 can be expression products of the same gene biomarker. The gene biomarker can comprise genomic DNA encoding the gene, including exons, introns, and/or regulatory binding regions (such as enhancers, promoters, silencers, and/or response elements). Point mutations, polymorphisms, translocations, insertions, deletions, amplifications, inversions, microsatellites, interstitial deletions, CNVs, loss of heterozygosity, or any other aberrations which affect the structure or function of one or more gene biomarkers and/or expression products thereof, can be associated with EN as described herein.

Computer-Implemented Aspects

As understood by those of ordinary skill in the art, the methods and information described herein (genetic variation association with EN) can be implemented, in all or in part, as computer executable instructions on known computer readable media. For example, the methods described herein can be implemented in hardware. Alternatively, the method can be implemented in software stored in, for example, one or more memories or other computer readable medium and implemented on one or more processors. As is known, the processors can be associated with one or more controllers, calculation units and/or other units of a computer system, or implanted in firmware as desired. If implemented in software, the routines can be stored in any computer readable memory such as in RAM, ROM, flash memory, a magnetic disk, a laser disk, or other storage medium, as is also known. Likewise, this software can be delivered to a computing device via any known delivery method including, for example, over a communication channel such as a telephone line, the internet, a wireless connection, etc., or via a transportable medium, such as a computer readable disk, flash drive, etc.

More generally, and as understood by those of ordinary skill in the art, the various steps described above can be implemented as various blocks, operations, tools, modules and techniques which, in turn, can be implemented in hardware, firmware, software, or any combination of hardware, firmware, and/or software. When implemented in hardware, some or all of the blocks, operations, techniques, etc. can be implemented in, for example, a custom integrated circuit (IC), an application specific integrated circuit (ASIC), a field programmable logic array (FPGA), a programmable logic array (PLA), etc.

Results from such genotyping can be stored in a data storage unit, such as a data carrier, including computer databases, data storage disks, or by other convenient data storage means. In certain embodiments, the computer database is an object database, a relational database or a post-relational database. Data can be retrieved from the data storage unit using any convenient data query method.

When implemented in software, the software can be stored in any known computer readable medium such as on a magnetic disk, an optical disk, or other storage medium, in a RAM or ROM or flash memory of a computer, processor, hard disk drive, optical disk drive, tape drive, etc. Likewise, the software can be delivered to a user or a computing system via any known delivery method including, for example, on a computer readable disk or other transportable computer storage mechanism.

The steps of the claimed methods can be operational with numerous other general purpose or special purpose computing system environments or configurations. Examples of well-known computing systems, environments, and/or configurations that can be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and system can be described in the general context of computer-executable instructions, such as program modules, being executed by a computer. Generally, program modules include routines, programs, objects, components, and/or data structures that perform particular tasks or implement particular abstract data types. The methods and apparatus can also be practiced in distributed computing environments where tasks are performed by remote processing devices that are linked through a communications network. In both integrated and distributed computing environments, program modules can be located in both local and remote computer storage media including memory storage devices. Numerous alternative embodiments could be implemented, using either current technology or technology developed after the filing date of this application, which would still fall within the scope of the claims defining the disclosure.

While the risk evaluation system and method, and other elements, have been described as being implemented in software, they can be implemented in hardware, firmware, etc., and can be implemented by any other processor. Thus, the elements described herein can be implemented in a standard multi-purpose CPU or on specifically designed hardware or firmware such as an application-specific integrated circuit (ASIC) or other hard-wired device as desired. When implemented in software, the software routine can be stored in any computer readable memory such as on a magnetic disk, a laser disk, or other storage medium, in a RAM or ROM of a computer or processor, in any database, etc. Likewise, this software can be delivered to a user or a screening system via any known or desired delivery method including, for example, on a computer readable disk or other transportable computer storage mechanism or over a communication channel, for example a telephone line, the internet, or wireless communication. Modifications and variations can be made in the techniques and structures described and illustrated herein without departing from the spirit and scope of the present disclosure.

EN Therapeutics

Medications and surgery can provide relief from the symptoms of EN. The main families of drugs useful for treating EN are NSAIDS, GnRH agonists and antagonists, oral contraceptives, progestin, danazol, and aromatase inhibitors. The stage of the disease may determine which therapy is most useful.

It can be appreciated by those skilled in the art that patient stratification methods (e.g., specific genotypes correlated with the disease or drug response) can be employed not only for targeted therapeutics, but in general for any drug that is approved or in development. For example, drugs in development or approved to treat, for example, cancer, may have utility in being repurposed to treat EN. Such patient stratification methods can also be utilized to develop a companion diagnostic test (e.g., for the specific genes/genotypes found in patients that are indicative of drug response) for a particular drug, either concurrently during the clinical trials for the drug or after drug approval (e.g., as a new indication or for the physician to use in guiding medical decisions for the patient).

Thus, those skilled in the art can appreciate that the gene product of one or more EN-associated genes listed in FIGS. 1-3 may be useful as a drug target for development of a therapeutic to treat a patient with an EN-associated genetic variant. For example, the protein product of a gene that is known to contain an EN-associated variant (such as an SNV or CNV) may have partial or full loss of function in an EN patient with the EN-associated genetic variant. In another embodiment, an EN-associated genetic variant may result in gain of function for the protein product expressed from the mutated gene, such as an activating mutation of the protein's function (e.g., kinase activity is aberrantly increased) or overexpression of the protein due to a CNV gain of the whole gene. Methods of drug screening for drug targets are well known to those skilled in the art. Drugs can be developed to specifically target a gene that is found to cause a particular disease (e.g., EN) due to the presence of a genetic variant or to another gene in a particular biochemical/cellular pathway (e.g., FIG. 9).

In one embodiment, drug development can be pursued on the basis that a gene is a target for drugs in development or already approved for use in one or more conditions, such as those genes listed in FIG. 10. For example, EN-associated genes in FIG. 3 that are known drug targets, according to FIG. 10, include CYP17A1, LEPR, PTK2, RXFP1, and TSHR. In another embodiment, a gene family member of a known drug target may have a higher probability of success in yielding an approved drug than a target with no prior efforts attempted for drug development. For example, EN-associated genes in FIG. 3 that are in the same gene family of known drug targets, according to FIG. 10, include DPP6 (FIG. 10, DPP4), GPR111 (FIG. 10, 4 GPR genes), HMGB3 (FIG. 10, HMGB1), MAGEA11 (FIG. 10, MAGEA3), MUC4 (FIG. 10, MUC1 and MUC16), MYO1B (FIG. 10, MYO7A), PDE1C (FIG. 10, 6 PDE genes), PGRMC2 (FIG. 10, PGR), PLA2G4C (FIG. 10, PLA2G4A), TGFBR3 (FIG. 10, TGFBR1 and TGFBR2), and TGFB1I1 (FIG. 10, TGFB signaling genes TGFB1, TGFB2, TGFBR1, TGFBR2).

For example, a drug approved or in development for one disease area may have therapeutic use in a related, or even unrelated, disease area. For example, the EN-associated gene RXFP1 is a known drug target (FIG. 10) and multiple pharmaceutical companies are developing drugs that target its gene product. The RXFP1 protein is a G-protein-coupled receptor and the endogenous hormone relaxin activates this receptor (Xiao et al., Probe Reports from the NIH Molecular Libraries Program [Internet] Bethesda (Md.): National Center for Biotechnology Information (US), 2010-2012 (2013, updated); Xiao et al., *Nat Commun.* 4:1953 (2013)). Recombinant relaxin hormone is in development for treatment of heart failure. Analogs of relaxin, such as H2:A(4-24)(F23A) (see Chan et al., *J. Biol. Chem.*, 287:41152 (2012)), have also been found to have potency. However, due to the short half-life of relaxin, it requires intravenous administration. Small molecule agonists of the relaxin receptor are being developed that are orally bioavailable (Xiao et al., supra). Those molecules can be identified using a high-throughput screening assay developed for the RXFP1 gene product (Chen et al., *J Biomol Screen.* 18:670 (2013)). Since RXFP1 has been reported to have lower expression in ectopic endometriotic tissues (see Table 1) and a deletion in the RXFP1 gene is associated with EN (FIG. 2), recombinant relaxin, relaxin analogs or RXFP1 small molecule agonists may have therapeutic value in certain EN patients. For example, Xiao et al. (supra) reported that relaxin, via its RXFP1 receptor, regulates cellular processes such as extracellular matrix remodeling, cell invasiveness, and proliferation, which are also known to be involved in the pathology of endometriosis. Those skilled in the art also appreciate that therapeutics developed to target a specific gene (or its products) can be administered on the basis of a patient testing positive for a particular genetic variant that impacts the gene target or another gene in the same molecular pathway. In some embodiments, a genetic test is developed as a companion diagnostic test for a specific therapeutic.

RNA Therapeutics

The nucleic acids and/or variants of the disclosure, or nucleic acids comprising their complementary sequence, can be used as antisense constructs to control gene expression in cells, tissues or organs. The methodology associated with antisense techniques is well known to the skilled artisan, and is described and reviewed in Antisense Drug Technology; Principles, Strategies, and Applications, Crooke, Marcel Dekker Inc., New York (2001) In general antisense nucleic acids are designed to be complementary to a region of mRNA expressed by a gene, so that the antisense molecule hybridizes to the mRNA, thus blocking translation of the mRNA into protein Several classes of antisense oligonucleotide are known to those skilled in the art, including cleavers and blockers. The former bind to target RNA sites, activate intracellular nucleases (e.g., Rnase H or Rnase L) that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today.* 7:912-917 (2002)) Antisense oligonucleotides are useful directly as therapeutic agents, and are also useful for determining and validating gene function, for example by gene knock-out or gene knock-down experiments. Antisense technology is further described in Lavery et al., *Curr. Opin. Drug Discov. Devel.,* 6:561-569 (2003), Stephens et al., *Curr, Opin. Mol Ther.,* 5:118-122 (2003), Kurreck, *Eur. J. Biochem.,* 270:1628-44 (2003), Dias et al, *Mol. Cancer Ter.,* 1:347-55 (2002), Chen, *Methods Mol. Med.,* 75:621-636 (2003), Wang et al., *Curr. Cancer Drug Targets,* 1:177-96 (2001), and Bennett, *Antisense Nucleic Acid Drug. Dev.,* 12 215-24 (2002).

The variants described herein can be used for the selection and design of antisense reagents that are specific for particular variants (e.g., particular genetic variations or polymorphic markers in linkage disequilibrium with particular genetic variations). Using information about the variants described herein, antisense oligonucleotides or other antisense molecules that specifically target mRNA molecules that contain one or more variants of the disclosure can be designed. In this manner, expression of mRNA molecules that contain one or more variants of the present disclosure (markers and/or haplotypes) can be inhibited or blocked. In some embodiments, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat EN. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature,* 391:806-11 (1998)), and in recent years its potential use in treatment of human disease has been actively pursued (reviewed in Kim & Rossi, *Nature Rev. Genet.,* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the disclosure relates to isolated nucleic acid sequences, and the use of those molecules for RNA interference, for example as small interfering RNA molecules (siRNA). In some embodiments, the isolated nucleic acid sequences can be 18-26 nucleotides in length, or 19-25 nucleotides in length, or 20-24 nucleotides in length, or 21, 22 or 23 nucleotides in length.

Another pathway for RNAi-mediated gene silencing originates in endogenously encoded primary microRNA (pn-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.,* 8:173-204 (2007)).

Clinical applications of RNAi include the incorporation of synthetic siRNA duplexes, which are approximately 20-23 nucleotides in size, and may have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, such as about 27 nucleotides), as well as small hairpin RNAs (shRNAs; typically about 29 nucleotides in length). The latter are naturally expressed, as described in Amarzguioui et al. (*FEBS Lett.,* 7:5974-81 (2005)). Chemically synthetic siRNAs and shRNAs are substrates for in vivo processing, and in some cases provide more potent gene-silencing than shorter designs (Kim et al., *Nature Biotechnol.,* 2:222-226 (2005); Siola et al., *Nature Biotechnol.,* 3:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.,* 23:559-565 (2006), Brummelkamp et al., *Science.* 9:550-553 (2002)).

Since RNAi molecules, including siRNA, miRNA and shRNA, act in a sequence-dependent manner, variants described herein can be used to design RNAi reagents that recognize specific nucleic acids comprising specific genetic variations, alleles and/or haplotypes, while not recognizing nucleic acid sequences not comprising the genetic variation, or comprising other alleles or haplotypes. These RNAi reagents can thus recognize and destroy the target nucleic acid sequences. As with antisense reagents, RNAi reagents can be useful as therapeutic agents (i.e., for turning off disease-associated genes or disease-associated gene variants), but can also be useful for characterizing and validating gene function (e.g., by gene knock-out or gene knock-down experiments).

Delivery of RNAi can be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles Viral delivery methods include use of lentivirus, adenovirus and adeno-associated virus The siRNA molecules are in some embodiments chemically modified to increase their stability. This can include modifications at the 2' position of the ribose, including 2'-O-methylpunnes and 2'-fluompyrimidmes, which provide resistance to RNase activity. Other chemical modifications are possible and known to those skilled in the art.

The following references provide a further summary of RNAi, and possibilities for targeting specific genes using RNAi: Kim & Rossi, *Nat. Rev. Genet.*, 8:173 (2007), Chen & Rajewsky, *Nat. Rev, Genet.*, 8:93 (2007), Reynolds, et al., *Nat. Biotechnol.*, 22:326 (2004), Chi et al., *Proc. Natl. Acad. Sa. USA*, 100:6343 (2003), Vickers et al., *J. Bio. Chem.*, 27:7108 (2003). Agami, *Curr. Opin. Chem. Biol.*, 6:829 (2002), Lavery, et al., *Curr. Opin. Drug Discov. Devel.*, 6:561 (2003), Shi, *Trends Genet.*, 19:9 (2003), Shuey et al., *Drug Discov. Today*, 7:1040 (2002), McManus et al., *Nat. Rev. Genet.*, 3:737 (2002), Xia et al., *Nat. Biotechnol.*, 20:1006 (2002, Plasterk et al., *Curr. Opin Genet. Dev.*, 19:562 (2000), Bosher et al., *Nat. Cell Biol.*, 2:E31 (2000), and Hunter, *Curr. Biol.*, 9:R440 (1999).

A genetic defect leading to increased predisposition or risk for development of EN or a defect causing the disease, can be corrected permanently by administering to a subject carrying the defect a nucleic acid fragment that incorporates a repair sequence that supplies the normal/wild-type nucleotide(s) at the site of the genetic defect. Such site-specific repair sequence can encompass an RNA/DNA oligonucleotide that operates to promote endogenous repair of a subject's genomic DNA. The administration of the repair sequence can be performed by an appropriate vehicle, such as a complex with polyethelamine, encapsulated in anionic liposomes, a viral vector such as an adenovirus vector, or other pharmaceutical compositions suitable for promoting intracellular uptake of the administered nucleic acid The genetic defect can then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation. It is generally considered that the major mechanism of RNA induced silencing (RNA interference, or RNAi) in mammalian cells is mRNA degradation. RNA interference (RNAi) is a mechanism that inhibits gene expression at the stage of translation or by hindering the transcription of specific genes. Specific RNAi pathway proteins are guided by the dsRNA to the targeted messenger RNA (mRNA), where they "cleave" the target, breaking it down into smaller portions that can no longer be translated into protein. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems. Another outcome is epigenetic changes to a gene—histone modification and DNA methylation—affecting the degree the gene is transcribed.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al., *EMBO J.*, 21:5864 (2002); Tabara et al., *Cell*, 109:861 (2002); Martinez et al., *Cell*, 110:563 (2002); Hutvagner & Zamore, *Science*, 297:2056 (2002).

From a mechanistic perspective, introduction of long double stranded RNA into plants and invertebrate cells is broken down into siRNA by a Type ill endonuclease known as Dicer. Sharp, RNA interference—2001, *Genes Dev.*, 15:485 (2001). Dicer, a ribonuclease-III-like enzyme, processes the dsRNA into 19-23 base pair short interfering RNAs with characteristic two base 3' overhangs. Bernstein, Caudy, Hammond, & Hannon, *Nature*, 409:363 (2001). The siRNAs are then incorporated into an RNA-induced silencing complex (RISC) where one or more helicases unwind the siRNA duplex, enabling the complementary antisense strand to guide target recognition (Nykanen, Haley, & Zamore, *Cell*, 197:309 (2001)). Upon binding to the appropriate target mRNA, one or more endonucleases within the RISC cleaves the target to induce silencing. Elbashir, Lendeckel, & Tuschl, (*Genes Dev.*, 1:188 (2001).

Generally, the antisense sequence is retained in the active RISC complex and guides the RISC to the target nucleotide sequence by means of complementary base-pairing of the antisense sequence with the target sequence for mediating sequence-specific RNA interference. It is known in the art that in some cell culture systems, certain types of unmodified siRNAs can exhibit "off target" effects. It is hypothesized that this off-target effect involves the participation of the sense sequence instead of the antisense sequence of the siRNA in the RISC complex (see for example, Schwarz et al., Cell, 115:199 (2003)). In this instance the sense sequence is believed to direct the RISC complex to a sequence (off-target sequence) that is distinct from the intended target sequence, resulting in the inhibition of the off-target sequence. In these double stranded nucleic acid sequences, each strand is complementary to a distinct target nucleic acid sequence. However, the off-targets that are affected by these dsRNAs are not entirely predictable and are non-specific.

The term "siRNA" refers to small inhibitory RNA duplexes that induce the RNA interference (RNAi) pathway. These molecules can vary in length (generally between 18-30 basepairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region. Small interfering RNA (siRNA), sometimes known as short interfering RNA or silencing RNA, are a class of 20-25 nucleotide-long double-stranded RNA molecules that play a variety of roles in biology.

While the two RNA strands do not need to be completely complementary, the strands should be sufficiently complementary to hybridize to form a duplex structure. In some instances, the complementary RNA strand can be less than 30 nucleotides, less than 25 nucleotides in length, about 19 to 24 nucleotides in length, or 20-23 nucleotides in length, including 22 nucleotides in length. The dsRNA of the present disclosure can further comprise at least one single-stranded nucleotide overhang. The dsRNA of the present disclosure can further comprise a substituted or chemically modified nucleotide. As discussed in detail below, the dsRNA can be synthesized by standard methods known in the art.

siRNA can be divided into five (5) groups including non-functional, semi-functional, functional, highly functional, and hyper-functional based on the level or degree of silencing that they induce in cultured cell lines. As used herein, these definitions are based on a set of conditions where the siRNA is transfected into the cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) can be used to compare siRNAs to a particular target for applications such as functional genomics, target identification and therapeutics.

microRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Antibody-Based Therapeutics

The present disclosure embodies agents that modulate a peptide sequence or RNA expressed from a gene associated with EN. The term biomarker, as used herein, can comprise a genetic variation of the present disclosure or a gene product, for example, RNA and polypeptides, of any one of the genes listed in FIGS. 1-4. Such modulating agents include, but are not limited to, proteins, peptides, peptidomimetics, peptoids, or any other forms of a molecule, which bind to, and alter the signaling or function associated with the EN associated biomarker, have an inhibitory or stimulatory effect on the EN associated biomarkers, or have a stimulatory or inhibitory effect on the expression or activity of the EN associated biomarkers' ligands, for example, polyclonal antibodies and/or monoclonal antibodies that specifically bind one form of the gene product but not to the other form of the gene product are also provided, or which bind a portion of either the variant or the reference gene product that contains the polymorphic site or sites.

In some embodiments, the present disclosure provides antibody-based agents targeting EN associated biomarkers. The antibody-based agents in any suitable form of an antibody, e.g., monoclonal, polyclonal, or synthetic, can be utilized in the therapeutic methods disclosed herein. The antibody-based agents include any target-binding fragment of an antibody and also peptibodies, which are engineered therapeutic molecules that can bind to human drug targets and contain peptides linked to the constant domains of antibodies. In some embodiments, the antibodies used for targeting EN associated biomarkers are humanized antibodies. Methods for humanizing antibodies are well known in the art. In some embodiments, the therapeutic antibodies comprise an antibody generated against EN associated biomarkers described in the present disclosure, wherein the antibodies are conjugated to another agent or agents, for example, a cytotoxic agent or agents.

The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the disclosure is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')2 fragments which can be generated by treating the antibody with an enzyme such as pepsin. The disclosure provides polyclonal and monoclonal antibodies that bind to a polypeptide of the disclosure. The term "monoclonal antibody" or "monoclonal antibody composition", as used herein, refers to a population of antibody molecules that contain only one species of an antigen binding site capable of immunoreacting with a particular epitope of a polypeptide of the disclosure. A monoclonal antibody composition thus typically displays a single binding affinity for a particular polypeptide of the disclosure with which it immunoreacts.

Polyclonal antibodies can be prepared as described above by immunizing a suitable subject with a desired immunogen, e.g., polypeptide of the disclosure or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature*, 25:495 (1975), the human B cell hybridoma technique (Kozbor et al., *Immunol. Today*, 4:72 (1983)), the EBV-hybridoma technique (Cole et al., *Monoclonal Antibodies and Cancer Therapy*, Alan R. Liss (1985) Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the disclosure.

Any of the many well-known protocols used for fusing lymphocytes and immortalized cell lines can be applied for the purpose of generating a monoclonal antibody to a polypeptide of the disclosure (see, e.g., *Current Protocols in Immunology*, supra; Galfre et al., *Nature*, 266.55052 (1977); R. H. Kenneth, in *Monoclonal Antibodies: A New Dimension In Biological Analyses*, Plenum Publishing Corp., New York, N.Y. (1980); and Lerner, *J. Biol. Med.*, 54:387 (1981)). Moreover, the ordinarily skilled worker can appreciate that there are many variations of such methods that also would be useful. Alternative to preparing monoclonal antibody-secreting hybridomas, a monoclonal antibody to a polypeptide of the disclosure can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01: and the Stratagene SurfZAP$^a$ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619, WO 91/17271, WO 92/20791, WO 92/15679; WO 93/01288, WO 92/01047, WO 92/09690, and WO 90/02809; Fuchs et al., *Bio/Technology*, 2:1370 (1991); Hay et al., *Hum. Antibod. Hybndomas*, 2:81 (1992); Huse et al., *Science*, 246:1275 (1989); and Griffiths et al., *EMBO J.*, 12:725 (1993).

Additionally, recombinant antibodies, such as chimeric and humanized monoclonal antibodies, comprising both human and non-human portions, which can be made using standard recombinant DNA techniques, are within the scope of the disclosure. Such chimeric and humanized monoclonal antibodies can be produced by recombinant DNA techniques known in the art.

In general, antibodies of the disclosure (e.g., a monoclonal antibody) can be used to isolate a polypeptide of the disclosure by standard techniques, such as affinity chromatography or immunoprecipitation. A polypeptide-specific antibody can facilitate the purification of natural polypeptide from cells and of recombinants produced polypeptide expressed in host cells Moreover, an antibody specific for a polypeptide of the disclosure can be used to detect the polypeptide (e.g., in a cellular lysate, cell supernatant, or tissue sample) in order to evaluate the abundance and pattern of expression of the polypeptide. Antibodies can be used diagnostically, prognostically, or theranostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotnazinylamine fluorescein, dansyl chloride or phycoerythnn; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. Antibodies can also be useful in pharmacogenomic analysis. In such embodiments, antibodies against variant proteins encoded by nucleic acids according to the disclosure, such as variant proteins that are encoded by nucleic acids that contain at least one genetic variation of the disclosure, can be used to identify individuals that can benefit from modified treatment modalities.

Antibodies can furthermore be useful for assessing expression of variant proteins in disease states, such as in active stages of a disease, or in an individual with a predisposition to a disease related to the function of the protein, in particular EN. Antibodies specific for a variant protein of the present disclosure that is encoded by a nucleic acid that comprises at least one polymorphic marker or haplotype as described herein can be used to screen for the presence of the variant protein, for example to screen for a predisposition to EN as indicated by the presence of the variant protein.

Antibodies can be used in other methods. Thus, antibodies are useful as screening tools for evaluating proteins, such as variant proteins of the disclosure, in conjunction with analysis by electrophoretic mobility, isoelectric point, tryptic or other protease digest, or for use in other physical assays known to those skilled in the art. Antibodies can also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or, for instance, endometrial or blood cell expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites for specific function or against an intact protein that is associated with a cell or cell membrane.

The present disclosure also embodies the use of any pharmacologic agent that can be conjugated to an antibody or an antibody binding fragment, and delivered in active form. Examples of such agents include cytotoxins, radioisotopes, hormones such as a steroid, anti-metabolites such as cytosines, and chemotherapeutic agents. Other embodiments can include agents such as a coagulant, a cytokine, growth factor, bacterial endotoxin or a moiety of bacterial endotoxin. The targeting antibody-based agent directs the toxin to, and thereby selectively modulates the cell expressing the targeted surface receptor. In some embodiments, therapeutic antibodies employ cross-linkers that provide high in vivo stability (Thorpe et al., *Cancer Res.*, 48:6396 (1988)). In any event, it is proposed that agents such as these can, if desired, be successfully conjugated to antibodies or antibody binding fragments, in a manner that can allow their targeting, internalization, release or presentation at the site of the targeted cells expressing the EN associated biomarkers using known conjugation technology. For administration in vivo, for example, an antibody can be linked with an additional therapeutic payload, such as radionuclide, an enzyme, an immunogenic epitope, or a cytotoxic agent, including bacterial toxins (diphtheria or plant toxins, such as ricin), The in vivo half-life of an antibody or a fragment thereof can be increased by pegylation through conjugation to polyethylene glycol.

Methods of Treatment

One embodiment of the present disclosure relates to methods of using pharmaceutical compositions and kits comprising agents that can reduce or increase the function and/or activity of polypeptides and/or nucleic acids that are associated with EN to inhibit or decrease EN progression. Another embodiment of the present disclosure provides methods, pharmaceutical compositions, and kits for the treatment of animal subjects. The term "animal subject" as used herein includes humans as well as other mammals. The term "treating" as used herein includes achieving a therapeutic benefit and/or a prophylactic benefit. By therapeutic benefit is meant eradication or amelioration of the underlying cause of EN. Also, a therapeutic benefit is achieved with the eradication or amelioration of one or more of the physiological symptoms associated EN such that an improvement is observed in the animal subject, notwithstanding the fact that the animal subject can still be afflicted with EN.

For embodiments where a prophylactic benefit is desired, a pharmaceutical composition of the disclosure can be administered to a subject at risk of developing EN, or to a subject reporting one or more of the physiological symptoms of EN, even though a screening of the condition cannot have been made. Administration can prevent EN from developing, or it can reduce, lessen, shorten and/or otherwise ameliorate the progression of EN, or symptoms that develop. The pharmaceutical composition can modulate a target EN associated biomarker. Wherein, the term modulate includes inhibition of EN associated biomarkers or alternatively activation of EN associated biomarkers.

Reducing the activity and/or function of polypeptides and/or nucleic acids found to be associated with EN, is also referred to as "inhibiting" the polypeptides and/or nucleic acids. The term "inhibits" and its grammatical conjugations, such as "inhibitory," do not require complete inhibition, but refer to a reduction in EN associated biomarkers' activities. In some embodiments, such reduction is by at least 5%, at least 10%, at least 20%, at least 30%, at least 40%, at least 50%, at least 75%, at least 90%, and can be by at least 95% of the activity of the enzyme in the absence of the inhibitory effect, e.g., in the absence of an inhibitor. Conversely, the phrase "does not inhibit" and its grammatical conjugations refer to situations where there is less than 20%, less than 10%, and can be less than 5%, of reduction in enzyme activity in the presence of the agent. Further the phrase "does not substantially inhibit" and its grammatical conjugations refer to situations where there is less than 30%, less than 20%, and in some embodiments less than 10% of reduction in enzyme activity in the presence of the agent.

Increasing the activity and/or function of polypeptides and/or nucleic acids found to be associated with EN, is also referred to as "activating" the polypeptides and/or nucleic acids. The term "activated" and its grammatical conjugations, such as "activating," do not require complete activation, but refer to an increase in EN associated biomarkers' activities. In some embodiments such increase is by at least 5%, at least 10%, at least 20%, at least 30%, at least 40%, at least 50%, at least 60%, at least 70%, at least 75%, at least 80%, at least 85%, at least 90%, and can be by at least 95% of the activity of the enzyme in the absence of the activation effect, e.g., in the absence of an activator. Conversely, the phrase "does not activate" and its grammatical conjugations refer to situations where there can be less than 20%, less than 10%, and less than 5%, of an increase in enzyme activity in the presence of the agent. Further the phrase "does not substantially activate" and its grammatical conjugations refer to situations where there is less than 30%, less than 20%, and in some embodiments less than 10% of an increase in enzyme activity in the presence of the agent.

The ability to reduce enzyme activity is a measure of the potency or the activity of an agent, or combination of agents, towards or against the enzyme. Potency can be measured by cell free, whole cell and/or in vivo assays in terms of IC50, Ki and/or ED50 values. An IC50 value represents the concentration of an agent to inhibit enzyme activity by half (50%) under a given set of conditions. A Ki value represents the equilibrium affinity constant for the binding of an inhibiting agent to the enzyme. An ED50 value represents the dose of an agent to affect a half-maximal response in a biological assay. Further details of these measures will be appreciated by those of ordinary skill in the art, and can be found in standard texts on biochemistry, enzymology, and the like.

The present disclosure also includes kits that can be used to treat EN. These kits comprise an agent or combination of agents that inhibits an EN associated biomarker and in some embodiments instructions teaching the use of the kit according to the various methods and approaches described herein. Such kits can also include information, such as scientific literature references, package insert materials, clinical trial results, and/or summaries of these and the like, which indicate or establish the activities and/or advantages of the agent. Such information can be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

Kits

Kits useful in the methods of the disclosure comprise components useful in any of the methods described herein, including for example, primers for nucleic acid amplification, hybridization probes for detecting genetic variation, or other marker detection, restriction enzymes, nucleic acid probes, optionally labeled with suitable labels, allele-specific oligonucleotides, antibodies that bind to an altered polypeptide encoded by a nucleic acid of the disclosure as described herein or to a wild type polypeptide encoded by a nucleic acid of the disclosure as described herein, means for amplification of genetic variations or fragments thereof, means for analyzing the nucleic acid sequence of nucleic acids comprising genetic variations as described herein, means for analyzing the amino acid sequence of a polypeptide encoded by a genetic variation, or a nucleic acid associated with a genetic variation, etc. The kits can for example include necessary buffers, nucleic acid primers for amplifying nucleic acids, and reagents for allele-specific detection of the fragments amplified using such primers and necessary enzymes (e.g., DNA polymerase). Additionally, kits can provide reagents for assays to be used in combination with the methods of the present disclosure, for example reagents for use with other screening assays for EN.

In some embodiments, the disclosure pertains to a kit for assaying a sample from a subject to detect the presence of a genetic variation, wherein the kit comprises reagents necessary for selectively detecting at least one particular genetic variation in the genome of the individual. In some embodiments, the disclosure pertains to a kit for assaying a sample from a subject to detect the presence of at least particular allele of at least one polymorphism associated with a genetic variation in the genome of the subject. In some embodiments, the reagents comprise at least one contiguous oligonucleotide that hybridizes to a fragment of the genome of the individual comprising at least genetic variation. In some embodiments, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one genetic variation, or a fragment of a genetic variation. Such oligonucleotides or nucleic acids can be designed using the methods described herein. In some embodiments, the kit comprises one or more labeled nucleic acids capable of allele-specific detection of one or more specific polymorphic markers or haplotypes with a genetic variation, and reagents for detection of the label. In some embodiments, a kit for detecting SNP markers can comprise a detection oligonucleotide probe, that hybridizes to a segment of template DNA containing a SNP polymorphisms to be detected, an enhancer oligonucleotide probe, detection probe, primer and/or an endonuclease, for example as described by Kutyavin et al. (*Nucleic Acid Res.*, 3.4:e128 (2006)).

In some embodiments, the DNA template is amplified by any means of the present disclosure, prior to assessment for the presence of specific genetic variations as described herein. Standard methods well known to the skilled person for performing these methods can be utilized, and are within scope of the disclosure. In one such embodiment, reagents for performing these methods can be included in the reagent kit.

In a further aspect of the present disclosure, a pharmaceutical pack (kit) is provided, the pack comprising a therapeutic agent and a set of instructions for administration of the therapeutic agent to humans screened for one or more variants of the present disclosure, as disclosed herein. The therapeutic agent can be a small molecule drug, an antibody, a peptide, an antisense or RNAi molecule, or other therapeutic molecules as described herein. In some embodiments, an individual identified as a carrier of at least one variant of the present disclosure is instructed to take a prescribed dose of the therapeutic agent. In one such embodiment, an individual identified as a carrier of at least one variant of the present disclosure is instructed to take a prescribed dose of the therapeutic agent. In some embodiments, an individual identified as a non-carrier of at least one variant of the present disclosure is instructed to take a prescribed dose of the therapeutic agent.

Also provided herein are articles of manufacture, comprising a probe that hybridizes with a region of human chromosome as described herein and can be used to detect a polymorphism described herein. For example, any of the probes for detecting polymorphisms described herein can be combined with packaging material to generate articles of manufacture or kits. The kit can include one or more other elements including: instructions for use; and other reagents such as a label or an agent useful for attaching a label to the probe. Instructions for use can include instructions for screening applications of the probe for making a diagnosis, prognosis, or theranosis to EN in a method described herein. Other instructions can include instructions for attaching a label to the probe, instructions for performing in situ analysis with the probe, and/or instructions for obtaining a sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof that can have an abnormality associated with a particular endophenotype. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

In some embodiments, an in vitro screening test can comprise one or more devices, tools, and equipment configured to collect a genetic sample from an individual. In some embodiments of an in vitro screening test, tools to collect a genetic sample can include one or more of a swab, a scalpel, a syringe, a scraper, a container, and other devices and reagents designed to facilitate the collection, storage, and transport of a genetic sample. In some embodiments, an in vitro screening test can include reagents or solutions for collecting, stabilizing, storing, and processing a genetic sample.

Such reagents and solutions for nucleotide collecting, stabilizing, storing, and processing are well known by those of skill in the art and can be indicated by specific methods used by an in vitro screening test as described herein. In some embodiments, an in vitro screening test as disclosed herein, can comprise a microarray apparatus and reagents, a flow cell apparatus and reagents, a multiplex nucleotide sequencer and reagents, and additional hardware and software necessary to assay a genetic sample for certain genetic markers and to detect and visualize certain genetic markers.

The present disclosure further relates to kits for using antibodies in the methods described herein. This includes, but is not limited to, kits for detecting the presence of a variant protein in a test sample. One embodiment comprises antibodies such as a labeled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit. In certain embodiments, the kit further comprises a set of instructions for using the reagents comprising the kit.

Unless otherwise explained, all technical and scientific terms used herein have the same meaning as commonly understood by one of ordinary skill in the art to which this disclosure belongs. The following references contain embodiments of the methods and compositions that can be used herein: *The Merck Manual of Diagnosis and Therapy*, 18th Edition, published by Merck Research Laboratories, 2006 (ISBN 0-911910-18-2); Benjamin Lewin, *Genes IX*, published by Jones & Bartlett Publishing, 2007 (ISBN-13: 9780763740634); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Standard procedures of the present disclosure are described, e.g., in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology; Guide to Molecular Cloning Techniques*, Vol. 152, S. L. Berger and A. R. Kimmerl (eds.), Academic Press Inc., San Diego, USA (1987)). *Current Protocols in Molecular Biology* (CPMB) (Fred M. Ausubel, et al. ed., John Wiley and Sons. Inc.), *Current Protocols in Protein Science* (CPPS) (John E. Coligan, et. al., ed., John Wiley and Sons, Inc.), *Current Protocols in Immunology* (CPI) (John E. Coligan, et. al., ed. John Wiley and Sons, Inc.), *Current Protocols in Cell Biology* (CPCB) (Juan S. Bonifacino et. al. ed., John Wiley and Sons, Inc.), *Culture of Animal Cells: A Manual of Basic Technique* by R. Ian Freshney, Publisher: Wiley-Liss; 5th edition (2005), and *Animal Cell Culture Methods* (Methods in Cell Biology, Vol. 57, Jennie P. Mather and David Barnes editors, Academic Press, 1st edition, 1998), which are all incorporated by reference herein in their entireties.

It should be understood that the following examples should not be construed as being limiting to the particular methodology, protocols, and compositions, etc., described herein and, as such, can vary. The following terms used herein is for the purpose of describing particular embodiments only, and is not intended to limit the scope of the embodiments disclosed herein.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art can recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described as these can vary. It is also to be understood that the terminology used herein is for the purpose of describing particular embodiments only, and is not intended to limit the scope of the present disclosure which can be limited only by the appended claims.

Unless defined otherwise, all technical and scientific terms used herein have the meanings that would be commonly understood by one of skill in the art in the context of the present specification.

It should be noted that as used herein and in the appended claims, the singular forms "a," "an," and "the" include plural reference unless the context clearly dictates otherwise. Thus, for example, reference to "a nucleotide" includes a plurality of such nucleotides; reference to "the nucleotide" is a reference to one or more nucleotides and equivalents thereof known to those skilled in the art, and so forth.

The term "and/or" shall in the present context be understood to indicate that either or both of the items connected by it are involved. While preferred embodiments of the present disclosure have been shown and described herein, it can be obvious to those skilled in the art that such embodiments are provided by way of example only. Numerous variations, changes, and substitutions can now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

The invention will be further described by the following non-limiting examples.

Example 1

The present invention is not based on finding common variants that increase the risk for or cause disease, but rather rare variants. In this context 'rare' refers to variants that are present/observed in disease cohorts at a certain frequency but never or almost never in normal (non-disease or unaffected) subjects. 'Rare' refers to the frequency in normal cohorts, but not necessarily in disease cohorts. Thus, a variant may actually be 'common' in the disease cohort but if absent or present at low frequency in a normal cohort, it would be classed as a 'rare' variant. The present invention is based on a discovery method that differs from traditional 'common variant' studies which, by design, typically identify weak associations between variants and disease (e.g., with low odds ratios of <1.5), since the variants being studied are known, in advance, to be present at an appreciable frequency in normal/unaffected subjects. As an example, consider the TGFBR3 deletion found in 3/100 EN cases but in 0/1,005 normal subjects (see FIG. 5). This deletion is clearly 'very rare' in normal subjects (found in the study described herein at 0% frequency) but this is not so in the EN cohort (the deletion is found at a frequency of 3%). While there is no specific frequency cutoff that defines a variant as rare or common, it is generally accepted by those skilled in the art and the genetics field that rare variants occur at <1% frequency in the general population (i.e., the presence of the TGFBR3 deletion in the EN cohort at 3% frequency would be considered a 'common' variant by this general cutoff used for the population at large). The discovery methodology described herein is able to detect rare variants because it is not limited to the analysis of previously known variants, as is the case with the common variant SNP-based genome-wide association studies (GWAS) that have been employed by many skilled in the art for the discovery of genes that are causal or associated with the disease being studied. Thus, for a complex disease such EN, the present method identifies single highly causal genes and rare gene variations including intragenic regions or nongenic (intergenic) regions. Data was generated on the basis of a comparison of copy number variants (CNVs) identified in 2 cohorts: 1,005 Normal individuals (Normal Variation Engine—NVE): and 100 endometriosis (EN) cases.

Genomic DNA Sample Hybridization

Genomic DNA samples from individuals within the Normal cohort (NVE 'test' subjects) and from the Endo cohort (Endo 'test' subjects) were hybridized against a single, sex-matched reference individual as follows. Reference DNA samples were labeled with Cy5 and test subject DNA samples were labeled with Cy3. After labeling, samples were combined and co-hybridized to Agilent 1M feature oligonucleotide microarrays, design ID 021529 (Agilent Product Number G4447A) using standard conditions (array Comparative Genomic Hybridization—aCGH). Post-hybridization, arrays were scanned at 2 μm resolution, using Agilent's DNA microarray scanner, generating tiff images for later analysis.

All tiff images were analyzed using Agilent Feature Extraction (FE) software, with the following settings:
Human Genome Freeze: hg18:NCBI36:Mar2006
FE version: 10.7.3.1
Grid/design file: 021529_D_F_20091001
Protocol: CGH_107_Sep09

This procedure generates a variety of output files, containing about 1,000,000 rows of data, each corresponding to a specific feature on the array. This file was used to perform CNV calling using DNAcopy, an open source software package implemented in R via BioConductor (http://www.bioconductor.org/packages/release/bioc/html/DNAcopy.html). Losses or gains were determined according to a threshold $\log_2$ ratio, which was set at −/+0.35. In other words, all losses with a $\log_2$ ratio value $<=-0.35$ were counted, as were all gains with a $\log_2$ ratio $>=+0.35$. All log 2 ratio values were determined according to Cy3/Cy5 (Test/Reference). A minimum probe threshold for CNV-calling was set at 2 (2 consecutive probes were sufficient to call a CNV). A CNV list was thus generated for each individual in the 2 cohorts.

There were a total of 162,316 CNVs in the NVE cohort of 1,005 individuals (an average of 162 CNVs per individual). These CNVs (many of which appeared in multiple individuals) were 'merged' into a master list (NVE-master) of non-redundant CNV subregions, according to the presence or absence of the CNV subregion in individuals within the cohort. Using this approach, the NVE-master list has 14,693 distinct CNV subregions, some of which are uniquely present in a single individual and some of which are present in multiple individuals. For example, consider 3 individuals within the NVE cohort with the following hypothetical CNVs:
  A. Chr1:1-100,000;
  B. Chr1:10,001-100,000;
  C. Chr1:1-89,999;

In the master list, these would be merged into 3 distinct CNV subregions, as follows:
CNV subregion 1 Chr1:1-10,000 Patients A, C
CNV subregion 2 Chr1:10,001-89,999 Patients A, B, C
CNV subregion 3 Chr1:90,000-100,000 Patients A. B There were a total of 16,577 CNVs in the EN cohort of 100 individuals (an average of 166 CNVs per individual). These CNVs (many of which appeared in multiple individuals) were 'merged' into a master list (EN-master) of non-redundant CNV subregions, according to the presence or absence of the CNV subregion in individuals within the cohort. Using this approach, the EN-master list has 3,408 distinct CNV subregions, some of which are uniquely present in a single individual and some of which are present in multiple individuals.

CNV subregions of interest were obtained after:
1. Annotation in order to attach to each CNV region relevant information regarding overlap with known genes and exons;
2. A calculation of the odds ratio (OR) for each CNV subregion, according to the following formula:

$$*OR = (EN/(100-EN))/(NVE/(1005-NVE))$$

where:
EN=number of EN individuals with CNV subregion of interest
NVE=number of NVE individuals with CNV subregion of interest.

As an illustrative example, consider the CNV subregion chr1:92013987-92020793, which is found in 0 individuals in the NVE cohort and 3 individuals in the EN cohort.

The OR is:

$$(3.5/(97.5))/(0.5/(1005.5)) = 72.19$$

Note that, by one convention, if either of NVE or EN=0, a value of 0.5 is added to all 4 entries in the main formula above, in order to avoid dealing with infinities. This has the effect of artificially lowering OR values in cases where no individuals within the NVE have the CNV. This method is also used when calculating the Fisher's 2-tailed Exact Test (FET) in the event that any one of the variables is zero.

CNV subregions/genes that fulfill one of the following criteria were identified (see FIG. 1):
1. Strong biology linking the CNV subregion and/or the gene it overlaps, with known pathways/mechanisms or biology in EN (in some cases, statistical evidence is lacking but does not exclude the CNV subregion as a candidate);
2. Statistical analysis without obvious biological connection (FDR adjusted p-value <=0.05);
3. A combination of statistical significance and biology.

It can be appreciated by those skilled in the art that the number of EN candidate CNV subregions, irrespective of category, may increase or decrease as additional EN cohorts are analyzed.

FIG. 1 lists exemplary CNVs of interest. FIG. 2 shows the CNV coordinates for the actual CNV subregions found to be unique or significantly different between the disease and normal cohorts, as opposed to FIG. 1, which lists the original CNV coordinates. FIG. 2 also details whether genic CNV subregions of interest overlap an exon or not and the number of normal subjects and the number of disease subjects that harbor the relevant CNV subregion, reports Fisher's 2-tailed Exact Test (FET) and odds ratio (OR), and provides the category under which the CNV subregion falls with respect to statistical and/or biological significance as discussed above. FIG. 3 represents a non-redundant list for all genes listed in FIG. 2. For all genes listed in FIG. 2, FIG. 4 represents a non-redundant list of relevant RNA transcripts. Table I summarizes biology and uterus expression data for genes impacted by CNVs/CNV subregions of interest (NA=data or information 'not available').

The sequence file 3886.001PRV_ST25.txt contains genomic sequence information for (in the following order): All distinct CNVs listed in FIG. 1 (SEQ ID NOs: 1-47) and the full genomic extent of the transcripts listed in FIG. 4 (SEQ ID NOs: 48-149).

Examples of Sequences:
Sequence Entry Starts:
SEQ_ID 1=6,806 bp CNV (loss) involving an intron of the gene TGFBR3:

```
<210> 1
<211> 6807
<212> DNA
<213> Homo sapiens

<400> 1
actgaaacat tcattttcca agattcctttt ccaaattcaa ctccatggtc tttcttttgt    60
ctgttttgct aaagggcaaa atactaacct gtttccaagc tattcagcaa tattttggca   120
caggtaatcc agtaagagaa ttgtttgtat agaacagagc tgatgttaat aacagggtgc   180

.................................................(sequence
truncated for brevity)

aaagcactgc ttgcacatcg actgacctga ggttgagagg aggagcagag gaatgtggaa  6720
aggattgttt ttaccttcat taagtgttaa atttacctaa gactcccaga gagtcaatgc  6780
tcttcaggaa ctattctgag gcagaaa                                      6807
```

Sequence Entry Ends.
Sequence Entry Starts:
SEQ_ID 149=GPR111, transcript NM_153839, which is 41,208 bp in length:

```
<210> 149
<211> 41208
<212> DNA
<213> Homo sapiens

<400> 149
gcaaggtatg acagaagaga gccagtaatg cccatatctc cagctgccag ggagtggggc    60
aaatttgccg gtgagtttgt ctttggccag ccacagtgag tagtcccagg tcctccttct   120
ccttccagtg acttcctttg gagaggaatt tcagagatga gcagccactc atgattttgt   180

.................................................(sequence
truncated for brevity)

cctttggtc tttttgtgtg catatgtata tgtttgggg aatgggtat tcactttgt  41100 tactcactgt gttactcact tttgtatgcc catagtgcag agcatggtgc cttgtacata  41160
gagtatgttc ggtaaatatg tgcaataaaa agtcctttga ttacacaa               41208
```

Sequence Entry Ends.

TABLE I

Biological notes for genes impacted by CNVs/CNV Subregions of Interest

| CHR | START | STOP | Gene_symbol | Expression_data_uterus | Biology_notes | PubMed_PMID_No |
|---|---|---|---|---|---|---|
| 1 | 92,013,987 | 92,020,793 | TGFBR3 | yes | One of several TGF beta superfamily members involved in endometrial function, links to CNV-identified endometriosis candidates TGFB1I1 (Hic-5) and PTK2 (FAK) | 11912285, 15745937, 16613890, 16621788, 16885531, 21261473, 22562249, 23242524 |
| 23 | 149,901,706 | 149,902,701 | HMGB3 | yes | Family member HMGB1 expressed in endometrium and regulated by estradiol, progesterone, and nitric oxide | 18483013, 22014880 |
| 23 | 149,902,702 | 149,904,265 | HMGB3 | yes | Family member HMGB1 expressed in endometrium and regulated by estradiol, progesterone, and nitic oxide | 18483013, 22014880 |
| 6 | 96,610,680 | 96,625,609 | FUT9 | yes | Link between FUT9 (fucosyltransferase) and SELE (e-selectin) and endometrial, 16 PubMed citations for "fucosyltransferase AND endometrial", 15 PubMed citations for "e-selectin AND endometrial", 7 PubMed citations "e-selectin AND endometriosis" | 7627975, 23192350 |
| 7 | 31,844,434 | 31,851,158 | PDE1C | no | Regulates collagen homeostasis and is a key regulator of pathological vascular remodeling and CNV-identified endometriosis candidate TGFB1I1 (Hic-5) is linked to vascular remodeling and endometriosis, PDE1C maps to linkage peak 7p13-15 for endometriosis | 9366577, 18335582, 21112686, 21148428, 21576276, 21962439, 22472216 |
| 10 | 59,620,764 | 59,630,493 | IPMK | no | IPMK linked to p53 and 95 PubMed citations for "p53 AND endometriosis", IPMK linked to mTor and 8 PubMed citations for "mtor AND endometriosis" plus 111 PubMed citations for "mtor AND endometrial" | 21284988, 23550211, 23708509 |
| 2 | 233,285,559 | 233,298,235 | GIGYF2 | no | IGF-1 expression linked to endometriosis and GYGYF1 and GYGYF2 are transiently linked to IGF-I receptors by the Grb10 adapter protein (GRB10) following IGF-I stimulation, GYGYF2 has also been incorrectly identified as a Parkinson's disease gene (PARK11) | 12771153, 20844834, 23776368 |
| 6 | 138,516,944 | 138,520,155 | intergenic | no | Intergenic and located near KIAA1244 (BIG3), which is linked to estrogen/ER signaling in breast cancer | 19496786 |
| 11 | 44,056,561 | 44,058,123 | ACCS | yes | NA | 11470512, 22543105 |
| 7 | 153,645,525 | 153,647,352 | DPP6 | no | NA | NA |
| 6 | 120,674,750 | 120,680,729 | intergenic | NA | NA | NA |
| 16 | 31,356,038 | 31,434,641 | TGFB1I1 | yes | TGFB1I1 (Hic-5) is a coactivator of the progesterone receptor and may be involved in progesterone resistance observed in some endometriosis patients, linked to vascular remodeling, interacts with CNV-identified endometriosis candidate PTK2 and acts as a scaffold for focal adhesions, TP53 and CDKN1A (p21, WAF1, CIP1) genotypes correlate with endometriosis and TGFB1I1 transactivates CDKN1A, and potential pharmacolgoical link to HDAC inhibitors, links to CNV-identified endometriosis candidates TGFBR3 (betaglycan) PDE1C, and PTK2 (FAK) | 19389829, 21715447, 22472216, 22529104 |
| 8 | 142,060,703 | 142,065,735 | PTK2 | no | PTK2 (FAK) is implicated in endometriosis and endometrial cancer, links to CNV-identified endometriosis candidates TGFB1I1 (Hic-5) and TGFBR3 (betaglycan) | 17543958, 17550607, 18294638, 19471549, 20869705, 21058027, 21900245, 23242524 |

TABLE I-continued

Biological notes for genes impacted by CNVs/CNV Subregions of Interest

| CHR | START | STOP | Gene_symbol | Expression_data_uterus | Biology_notes | PubMed_PMID_No |
|---|---|---|---|---|---|---|
| 4 | 129,189,476 | 129,451,283 | PGRMC2 | yes | Gain of several genes, PGRMC2 has links to endometriosis and progesterone, and expression levels correlate with diminished ovarian reserve (see also CNV-identified endometriosis candidate MYADML) | 22307145, 22355044, 23276631, 23522067 |
| 19 | 41,532,062 | 41,533,404 | ZFP14 | no | NA | NA |
| 1 | 65,627,570 | 65,696,043 | LEPROT, LEPR | yes | CNV may result in gain-of-function for LEPROT and gain-of-function/loss-of-function for LEPR (several transcript variants), disruption of leptin signaling linked to endometriosis, LEPROT is a negative regulator of leptin signaling, LEPR mutations cause reduced fertility, LEPROT (and LEPROTL1) involved in growth hormone signaling, which is implicated in endometrial cancer and endometriosis | 16564564, 17962343, 18450952, 19854659, 20624279, 22265003, 22647716, 23184927, 23634146, 24239717, 24401660, 24845415 |
| 3 | 197,001,562 | 197,065,388 | MUC4 | yes | Complex CNV with 4-step change in copy number and part overlaps with a frequent CNV found in several endometriosis patients and controls, mucin proteins have been detected in normal and pathological endometrial tissues (MUC1 and MUC4 are major major ones expressed in endometriosis), MUC4 SNP associated with endometriosis development and endometriosis-related infertility | 17197898, 21349170 |
| 23 | 148,575,584 | 148,608,166 | MAGEA11 | yes | Complex CNV with duplicated and triplicated regions in a control but CNV is a gain-of-funtion, whereas in the endometriosis patient it loss-of-function (left breakpoint). MAGEA11 is a primate-specific gene and functions as an androgen receptor co-regulator with its mRNA levels expressed in a temporal manner in the endometrium, also found to regulate progesterone receptor during human endometrium development | 18048459, 22891251 |
| 2 | 242,109,998 | 242,153,935 | BOK | yes | Pro-apoptotic protein and apoptosis is linked to endometriosis, highly expressed in ovary, testis, and uterus, role in other reproductive biology (preeclampsia, ovarian development) | 9356461, 19942931, 21196342 |
| 14 | 80,613,390 | 80,649,876 | TSHR | yes | Thyroid hormone receptor protein expression found in macaques, TSHR and thyroid hormone receptors are expressed in human endometrium | 20691434, 22713859, 23806847 |
| 23 | 64,731,495 | 64,811,828 | MSN | no | Implicated in migration rate in endometrial stromal cells from endometriosis patients, MSN and CLDN7 mRNA and protein expression found in endometrial cancer, RNAi-mediated knockdown of related family member ezrin (EZR) reduces migration of endometrial cells in endometriosis, and links to CNV-identified endometriosis candidate TGFB1I1 (via CDKN1A) | 19095664, 19541800, 22225925, 22272721, 22544491, 23856463, 24012495 |
| 2 | 33,773,800 | 33,903,436 | MYADML | no | Associated with diminished ovarian reserve, which is observed in some endometriosis patients | 11209637, 22116950, 23446861 |
| 10 | 104,571,485 | 104,810,431 | CYP17A1 | no | Gain of whole gene for CYP17A1, upregulation found in endometrial cancers, conflicting reports of genotypes correlated wwith endometriosis and endometrial cancer | 11221867, 15823822, 18172694, 20886547, 23609033 |
| 4 | 159,674,653 | 159,683,362 | RXFP1 | NA | RXFP1 (aka LGR7) mRNA expression (and relaxin) are reduced in ectopic endometriotic samples. mRNA expression | 19416175, 20655530 |

TABLE I-continued

Biological notes for genes impacted by CNVs/CNV Subregions of Interest

| CHR | START | STOP | Gene_symbol | Expression_data_uterus | Biology_notes | PubMed_PMID_ No |
|---|---|---|---|---|---|---|
| 7 | 30,668,143 | 30,681,882 | CRHR2 | no | Differential expression found in eutopic and ectopic endometrium of endometriosis patients. | 23638035 |
| 19 | 53,252,457 | 53,257,305 | PLA2G4C | no | Involved in endometrial biology and linked to preterm birth; PLA2 enzymes are the rate-limiting step in prostaglandin synthesis and prostaglandins have numerous links endometriosis. | 17459165, 21184677, 22201853, 22658345, 24035605 |
| 2 | 24,798,190 | 24,806,680 | NCOA1 | no | NCOA1 (aka SRC1) is linked to PGR and is proposed to contribute to pathogenesis of endometriosis along with TNF and MMP9. | 22660634 |
| 7 | 139,757,225 | 139,828,667 | MKRN1 | no | Gene family member MKRN3 causes precocious puberty and both endometriosis and precocious puberty involve GnRH and are treatable with GnRH antagonists/agonists. | 23738509, 23817290 |
| 9 | 16,567,785 | 16,576,265 | BNC2 | yes | Involved in pigmentatation in animals and in a zebrafish model results in female infertility; endometriosis and ovarian cancer are associated and BNC2 variants have been associated with ovarian cancer. | 19956727, 21642636 |
| 1 | 16,713,074 | 16,799,710 | NBPF1 | no | NBPF1 interacts with clusterin and 15 PubMed citations for "clusterin AND endometrial" | 20096688, 22211095, 23589125 |
| 15 | 86,943,691 | 86,944,414 | intergenic | NA | Intergenic, 21Kb upstream of AEN, an apoptosis gene and apoptosis is linked to endometriosis | 18264133, 21196342 |
| 15 | 86,941,339 | 86,943,690 | intergenic | NA | Intergenic, 21Kb upstream of AEN, an apoptosis gene and apoptosis is linked to endometriosis21Kb upstream of AEN, an apoptosis gene and apoptosis is linked to endometriosis | 18264133, 21196342 |
| 2 | 191,869,063 | 191,873,037 | MYO1B | no | Actin expression levels linked to endometriosis and actin; MYO1B and actin links | 15475577, 20080738, 20471271, 22878529, 22735530 |
| 2 | 191,873,038 | 191,874,236 | MYO1B | no | Actin expression levels linked to endometriosis and actin; MYO1B and actin links | 15475577, 20080738, 20471271, 22878529, 22735530 |
| 6 | 47,731,384 | 47,734,315 | GPR111 | no | NA | 22837050 |
| 6 | 70,290,311 | 70,295,413 | intergenic | NA | NA | NA |

Example 2

Pathway analysis software may be used to identify whether the candidate gene is a drug target, which may be FDA-approved, in clinical trials or amenable for development of a new therapeutic. Such information will assist in the design of clinical trials (e.g., patient stratification for genetic subtypes) or will be used to facilitate clinical trials that are in progress, thereby reducing the attrition rate (failure to receive FDA approval) and reducing the time and cost of drug development. When a candidate EN gene is identified as a known drug target of an FDA-approved therapeutic, the drug can be repurposed and approved for use in a new indication (e.g., a cancer or anti-inflammatory agent may be beneficial to EN patients as well). Those skilled in the art will recognize that Phase II and III failures may be rescued with additional clinical trial data that accounts for genetic subtypes, particularly when the drug fails for lack of efficacy. For example, if a drug will be designed or established to target a particular gene defect (e.g., use of an RNAi therapeutic to decrease aberrant overexpression of the gene that is caused by a CNV or other type of genetic variant), it will be expected that only EN patients with that particular genetic subtype will benefit from the targeted therapy.

Example 3

Once a region is identified that has one or more genetic variations associated with EN, probes and/or primers can be prepared to further characterize those variations in test subjects. Targeted sequencing of CNV-identified regions/genes that are associated with EN (FIG. 2) and/or found to have EN-relevant biology (Table 1) is a preferred embodiment for further characterization of the genetic findings. Targeted sequencing enables ascertainment of the mutational spectrum in EN patients that are associated with EN. Targeted sequencing can be performed using one or more methods known to those skilled in the art such as, but not limited to, Sanger sequencing of PCR amplified regions, high-throughput sequencing of specific regions of interest, exome sequencing, or whole genome sequencing. Known and novel variants (SNPs/SNVs/indels) identified in sequencing experiments and/or data can be interpreted (mainly for exonic variants, but some adjacent intronic sequence variant data is also available) using NCBI's dbSNP, the Exome Variant Server (EVS) hosted by a website at the University of Washington (evs.gs.washington.edu/EVS/), or the Exome Aggregation Consortium (ExAC) browser hosted by the Broad Institute (http://exac.broadinstitute.org/) to assess their frequency in the general population. In another embodiment, interpretation of EN-associated regions/genes identified on the basis of CNVs can be performed on prexisting exome or whole genome sequence data (i.e., targeted interpretation). It can be appreciated by those skilled in the art that the genome search space for identifying other EN-associated variants is dramatically reduced by performing targeted sequencing and/or targeted interpretation of CNV-identified regions of interest (e.g., such analyses may involve sequencing/interpretation of variants present in only 20-30 EN candidate genes as opposed to variants present in all approximately 20,000 genes in the human genome). As described herein, genetic variations in TGFBR3 and PDE1C were found to be associated with EN (FIG. 2), TGFBR3 is one of several TGF beta superfamily members involved in endometrial and placental function, which includes activin/inhibin regulation. TGFBR3 is a proteoglycan that functions as a co-receptor for inhibins (INHA, INHBs) and TGF beta isoforms (TGFBs). TGFBR3 and INHA are down-regulated in endometrial carcinoma, and TGFBR3 is down-regulated in 90% breast cancers (via LOH or at the protein level). Restoring TGFBR3 expression inhibits tumor invasiveness, angiogenesis, and metastasis. Along with ARRB2, TGFBR3 regulates integrin α5β1 (ITGA5/ITGB1) trafficking and focal adhesion formation, which are processes implicated in endometriosis.

PDE1C has high affinity for cAMP and cGMP and is a calmodulin-dependent phosphdiesterase. PDE1C regulates collagen homeostasis and is a key regulator of pathological vascular remodeling. PDE1C (HG18; chr7:31759157-32304908) maps to a linkage peak found in familial endometriosis.

Example 4

The CNV analysis described herein (Example 1) revealed the presence of a 4-probe spanning heterozygous TGFBR3 deletion in 3 individuals with endometriosis (FIG. 5). The deletion is within an intron of TGFBR3 and was predicted, on the basis of the array data, to be at least 6.8 kb in size. Since the deletion was observed in 3 unrelated females, it was suspected that either the deletion occurs recurrently in different families; or the deletion represents an individual mutation that occurred some time ago and is present in descendants of the individual in whom it originally occurred (founder effect).

To determine whether the deletion was associated with EN or was an artifact and to map precise breakpoints at each end of the deletion, in order to define the size, the following experiments were conducted: 3 pairs of PCR primers were designed to amplify putative products of a given size only in those individuals who carried the deletion. One of these primer pairs successfully generated a product of the expected size in the deletion carriers but not in either normal DNA or DNA from an endometriosis patient without the deletion. The primer pair that had successfully generated a product in the deletion carriers was used again to amplify a product in all three carriers, for the purpose of Sanger sequencing. Data from Sanger sequencing revealed confirmation of the presence of the deletion in all 3 carriers; the precise sequence at each breakpoint; the precise size of the deletion (8,071 bp): and the presence of an extra 2 bp between the endpoints ('GG').

This data may be used to generate an even more efficient assay of the presence of the deletion in endometriosis cohorts and will be used as both a screening tool and a diagnostic test.

Methods and Results 3 sets of primers were tested:

| | | |
|---|---|---|
| OUTER_FWD | 57.21 | TTTTTGGTTAAACCCTACATCAC (SEQ ID NO: 150) |
| OUTER_REV | 59.52 | TCCCTAGCCCATTTCTAAATCTT (SEQ ID NO: 151) |
| MIDDLE_FWD | 59.55 | TCCCTTGCCAGTGGAACTAT (SEQ ID NO: 152) |
| MIDDLE_REV | 59.99 | TCGGCCAGAAGAGTCTGTTT (SEQ ID NO: 153) |
| INNER_FWD | 60.05 | TGAATTTCTGGCCATGTGAA (SEQ ID NO: 154) |
| INNER_REV | 60.13 | GAGAGGCCTGAGCACAAAAG (SEQ ID NO: 155) |

Only primers OUTER_FWD and OUTER_REV generated a product that was specific to the deletion carriers (and yielded negative results in normal DNA and in an individual with endometriosis who did not carry a deletion, based on the 1M array data). These PCR primers were used to amplify a product from all 3 deletion carriers, for the purpose of Sanger sequencing (FIG. 7).

Figure 7:
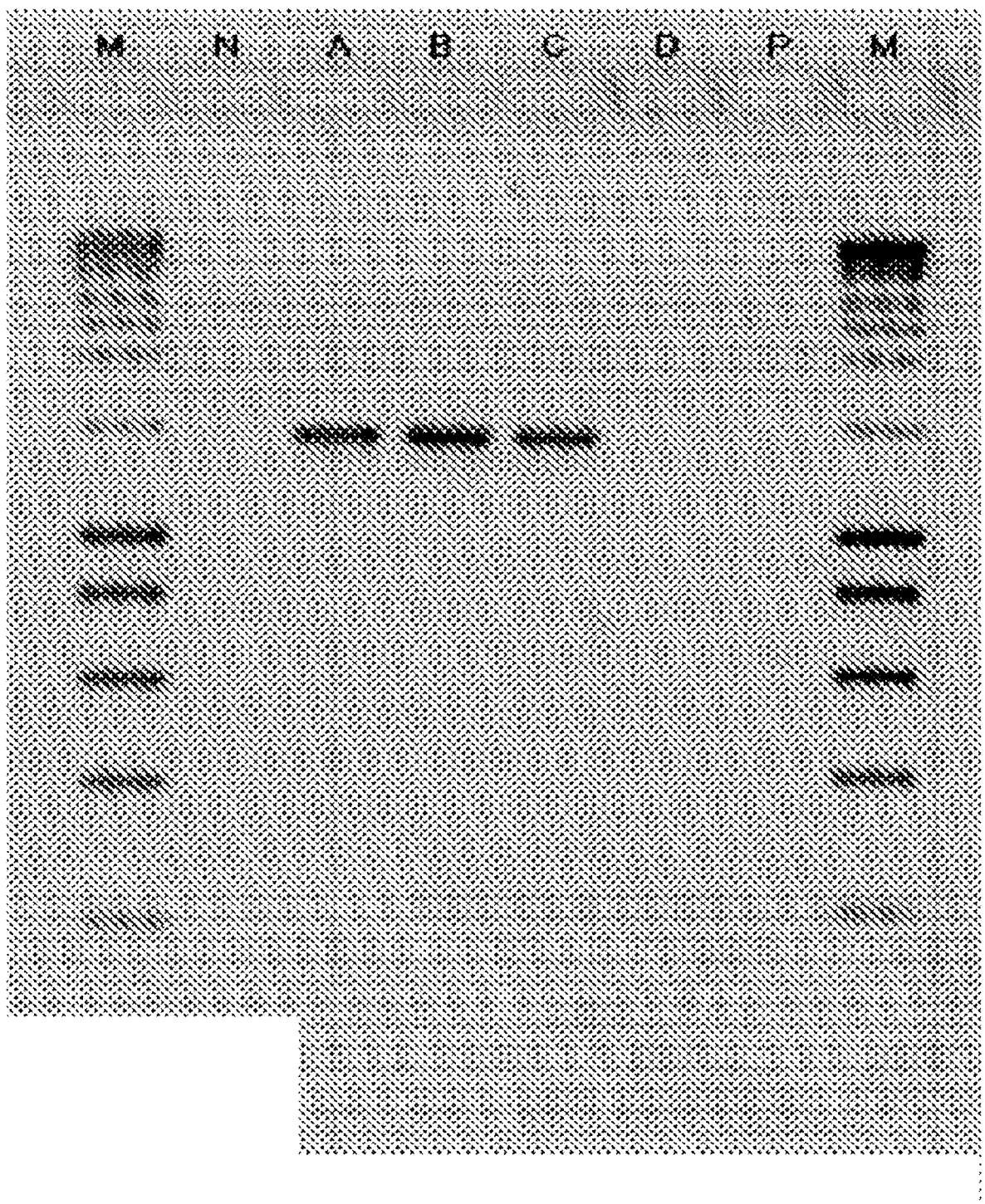
FIG. 7 shows amplification products from the use of a primer set to detect a deletion in TGFRB3. M=marker (Bioline Hyperladder I—200 bp, 400 bp, 600 bp, 800 bp, 1000 bp (bold), 1.5 kb, 2 kb, 2.5 kb, 3 kb, 4 kb, 5 kb, 6 kb, 8 kb, and 10 kb). N=No template control. A=D-001739 template (30 ng). Contains the deletion. B=D-002732 template (30 ng). Contains the deletion. C=D-003697 template (30 ng). Contains the deletion. D=D-001832 template (30 ng). Does not contain the deletion. P=Bioline pooled placental genomic DNA (30 ng).
Figure 8:
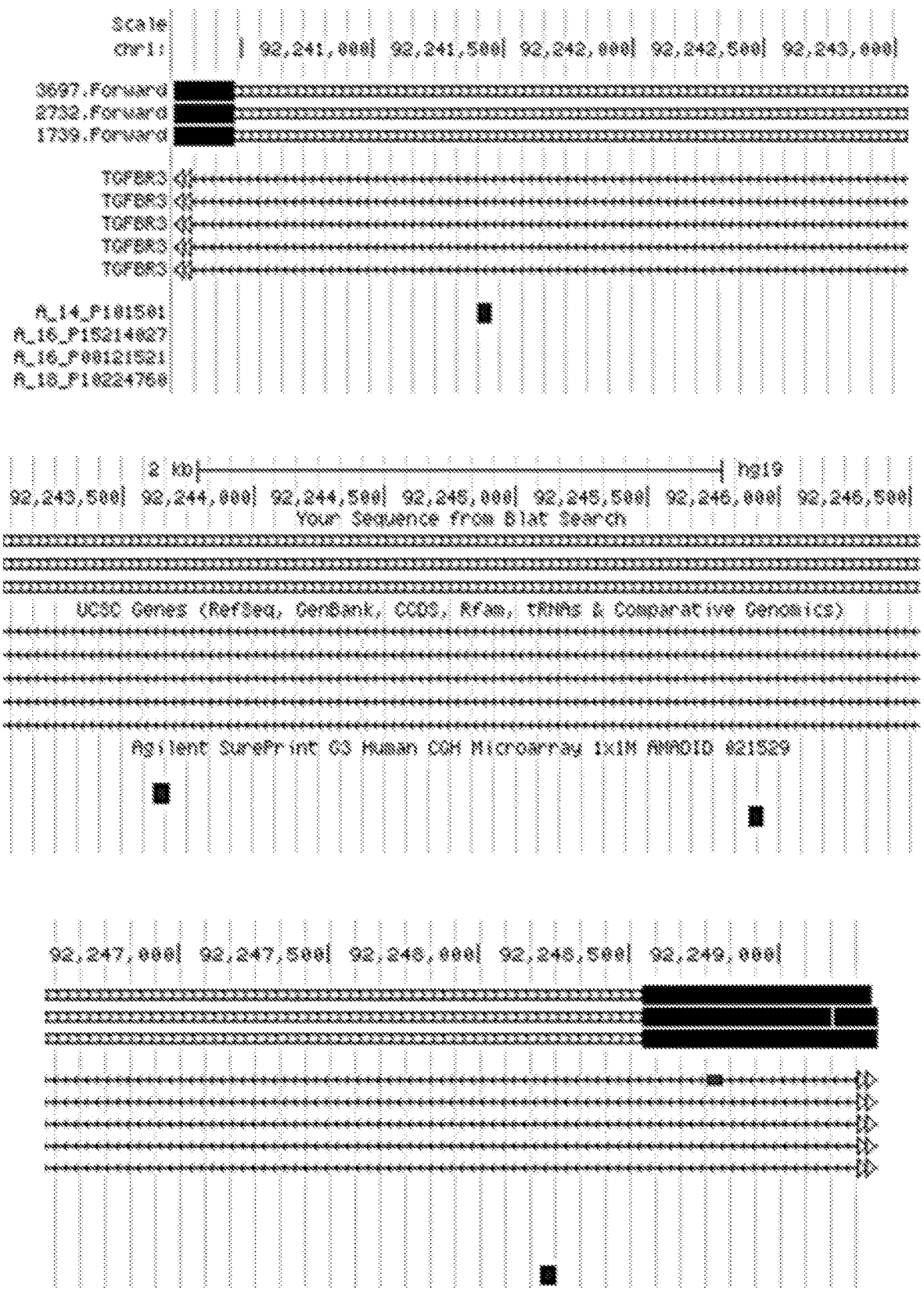
FIG. 8 is a BLAT analysis of Fwd sequence from 3 unrelated endometriosis cases with an approximately 8 kb deletion in an intron of TGFBR3, demonstrating the identical nature of the deletion in all 3 cases and the presence of 4 probes (as observed in the CNV array data herein, see FIG. 5 wherein the 4 probes define a minimal deletion size of approximately 6.8 kb) within the deletion.

The three products shown in FIG. 7 were purified and subjected to Sanger sequencing using the Fwd and Rev primers as sequencing primers. Sequence from the 3 products was queried, using BLAT, at the UCSC server (http://genome.ucsc.edu/cgi-bin/hgBlat?command=start). In each case, the sequence obtained with the Fwd sequencing primers clearly demonstrated the presence of an approximately 8 kb deletion, with apparently identical breakpoints in all 3 individuals (FIG. 8). Further analysis of the sequences revealed the deletion size to be 8,071 bp (which encompassed the expected 4 probes from the Agilent 1M feature (design ID 021529)) and was identical in all 3, unrelated, individuals.

The sequences (hg19 coordinates) obtained were as follows:

```
>1739.Forward
                                                            (SEQ ID NO: 156)
TAATCGACTCATGCGGTGATTGGGAATTCTTTCAGGGCAACAGGCAATGTGTTAAATATG

CACTGTTGAGTACACTGTGCAAAGTTATGAAATTCTCTCTTTCCCTCCTGACATTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAAGGT

GGAGCAAATTCAAAATGGATCAGATGTGTGTACACATGTATCAACAAATAGAAGTTAAGC
```

```
CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC

AAGAGTTGTACAAATTTCAGGTTCAGCTGAAGGACTCTGTGGTTCAGGTGAAAAAAAAG

CCATAAATACAAAGCATTATTGTAGGGTGCTTTGGACTAGAACCCTGTCTAATATCTGGG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGGGGGTAAAGCTTGAAAAGGCTGC

CAAATCCAATGACCAGCAACTTTTGAGCTGACTTAGAAAACAAGCTACAAAGACTTGAGT

CCAGAGTAAACAAGGAAAAAGCCATATTAAACAGGGAACAAATTACTATATCGGCAGGG

AAATTTTAA

>2732.Forward
                                                   (SEQ ID NO: 157)
TAATCGACTCATGCGGTGATTGGGAATTCTTTCAGGGCAACAGGCAATGTGTTAAATATG

CACTGTTGAGTACACTGTGCAAAGTTATGAAATTCTCTCTTTCCCTCCTGACATTTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAGGT

GGAGCAAATTCAAAATGGATCAGATGTGTGTACACATGTATCAACAAATAGAAGTTAAGC

CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC

AAGAGTTGTACAAATTTCAGGTTCAGCTGAAGGACTCTGTGGTTCAGGTGAAAAAAAAG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGTGGGTAAAGCTTGAAAAGGCTGC

CAAATCCAATGACCAGCAACTTTTGAGCTGACTTAGAAAACAAGCTACAAAGACTTGAGT

CCAGAGTAAACAAGGAAAAAGCCATATTAAACAGGGAACAAATTACTATATCGGCAGGG

ATATTTAA

>3697.Forward
                                                   (SEQ ID NO: 158)
TAATCGACTCATGCGGTGATTGGGAATTCTTTCAGGGCAACAGGCAATGTGTTAAATATG

CACTGTTGACTACACTGTGCAAAGTTATGAAATTCTCTCTTTCCCTCCTGACATTTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAGGT

GGAGCAAATTCAAAATGGATCAGATGTGTGTACACATGTATCAACAAATAGAAGTTAAGC

CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC

AAGAGTTGTACAAATTTCAGGTTCAGCTGAAGGACTCTGTGGTTCAGGTGAAAAAAAAG
```

-continued

```
CCATAAATACAAAGCATTATTGTAGGGTGCTTTGGACTAGAACCCTGTCTAATATCTGGG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGGGGGTAAAGCTTGAAAAGGCTGC

CAAATCCAATGACCAGCAACTTTTGAGCTGACTTAGAAAACAAGCTACAAAGACTTGAGT

CCAGAGTAAACAAGGAAAAAGCCATATTAAACAGGGAACAAATTAC
```

1739, 2732 and 3697 refer to anonymized identifiers for the 3 endometriosis cases.

These sequences, once analyzed using the UCSC server (using BLAT), were found to break down into the following subsequences:

```
>1739.Forward
                                                (SEQ ID NO: 159)
TAATCGACTCATGCGGTGATTGGGAATTCTTTCAGGGCAACAGGCAATGTGTTAAATATG

CACTGTTGAGTACACTGTGCAAAGTTATGAAATTCTCTCTTTCCCTCCTGACATTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAAGGT

GGAGCAAATTCAAAATGGATCAGATGTGTGTACACATGTATCAACAAATAGAAGTTAAGC

CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC

AAGAGTTGTACAAATTTCAGGTTCAGCTGAAGGACTCTGTGGTTCAGGTGAAAAAAAAAG

CCATAAATACAAAGCATTATTGTAGGGTGCTTTGGACTAGAACCCTGTCTAATATCTGGG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGGGGTAAAGCTTGAAAAGGCTGC

CAAATCCAATGACCAGCAACTTTTGAGCTGACTTAGAAAACAAGCTACAAAGACTTGAGT

CCAGAGTAAACAAGGAAAAAGCCATATTAAACAGGGAACAAATTACTATATCGGCAGGG

AAATTTTAA

>2732.Forward
                                                (SEQ ID NO: 160)
TAATCGACTCATGCGGTGATTGGGAATTCTTTCAGGGCAACAGGCAATGTGTTAAATATG

CACTGTTGAGTACACTGTGCAAAGTTATGAAATTCTCTCTTTCCCTCCTGACATTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAAGGT

GGAGCAAATTCAAAATGGATCAGATGTGTGTACACATGTATCAACAAATAGAAGTTAAGC

CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC
```

-continued
```
AAGAGTTGTACAAATTTCAGGTTCAGCTGAAGGACTCTGTGGTTCAGGTGAAAAAAAAG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGTGGGTAAAGCTTGAAAAGGCTGC

CAAATCCAATGACCAGCAACTTTTGAGCTGACTTAGAAAACAAGCTACAAAGACTTGAGT

CCAGAGTAAACAAAGGAAAAAGCCATATTAAACAGGGAACAAATTACTATATCGGCAGGG

ATATTTTAA

>3697.Forward
                                                    (SEQ ID NO: 161)
TAATCGACTCATGCGGTGATTGGGAATTCTTTCAGGGCAACAGGCAATGTGTTAAATATG

CACTGTTGACTACACTGTGCAAAGTTATGAAATTCTCTCTTTCCCTCCTGACATTTTTTT

TTCCAAGTACTTCACTGGCTACTCCAGAAGCAAAGGAATAGAGAAAAGAGTGAAATCAGA

ACTAGTGAGTGGACTTGGTTACTGTAAGATCACTGGTAAAAGTCTGAAAGAAACAAAGGT

GGAGCAAATTCAAAATGGATCAGATGTGTGTACACATGTATCAACAAATAGAAGTTAAGC

CATAATGGGCACAAGGGGACACTTCAGCTCCGGGCAAGAGTTAGGCTATGGTAGTGACCT

TGGATCCTAAAGCTGGGCTCTGTCCTTGCTTCACAGTGAGAATCAGTAACACCTCATCTC

ATTAGCTCTCTTATCTTCAAAAGTATCCAAGTCATACCTGTAATTTGCCCCTCATCCTCC

AAGAGTTGTACAAATTTCAGGTTCAGCTGAAGGACTCTGTGGTTCAGGTGAAAAAAAAG

CCATAAATACAAAGCATTATTGTAGGGTGCTTTGGACTAGAACCCTGTCTAATATCTGGG

CCTTGATATTTCAGCCTTTCAGACAAGGCCAAGGAGCTCAGAGACAAGGACTCCTTCAAT

CAGCCAGCAGTGCCACTGAGGTGCCCCGGCGGGCTGGACAGGAAAGCATGGAGAACATGG

CTGCAATGGAAGCCAAAGCAGCAGGTCTTCCAAACACAGACTCAGATGCCTGTGTCTTTA

AGACCAGACCCTCATAAATGGATTGCTTCTGCTGGACACCACGCTCTAAATAAACAGACT

CTTCTGGCCGACACACAACTTCCTGTAGGATTCTGGGGGGTAAAGCTTGAAAAGGCTGC

CAAATCCAATGACCAGCAACTTTTGAGCTGACTTAGAAAACAAGCTACAAAGACTTGAGT

CCAGAGTAAACAAAGGAAAAAGCCATATTAAACAGGGAACAAATTAC
```

In each case:

The first part of the sequence maps to: chr1:92240239-92240474 (hg19)

The second part of the sequence maps to: chr1:92248545-92249312 (hg19)

The precise deletion size is calculated as start of second segment−end of first segment: 92248545−92240474=8,071 bp The presence of the dinucleotide 'GG' in between these two sequences is likely a product of the type of event/mechanism that resulted in the deletion.

The outer primers defined above would be expected to generate a product of 9,499 bp (chr1:92,240,188-92,249,686) from a normal, wild-type genomic sequence, which does not harbor the deletion. In the 3 cases described above, the deletion is present heterozygously, so a wild-type, non-deleted allele is also present. A 9,499 bp band was not observed in FIG. 7 because amplification of PCR products in this size range requires specific, special conditions (long extension times, use of special polymerases etc). In standard PCR, products of 9,499 bp will not amplify efficiently and will remain unobserved on DNA gels. The reason that PCR across a deletion can be used as a screening tool is that the primers can be designed to generate a small PCR product only when a deletion is present, a product that cannot be generated from wild-type sequences, in which the primers are too far apart. Note that, in FIG. 7, the approximate size of the PCR product is 1.5 kb, which is consistent with the sequencing results:

Wild-type PCR product would be 9,499 bp (about 9.5 kb)
Outer primer PCR product about 1.5 kb
Deletion size=8,071 bp, and
about 8 kb deletion+1.5 kb PCR product size=about 9.5 kb wild-type primer distance.

Hence, the outer primer sequences described represent a screening tool that can be used diagnostically in endometriosis. By screening individuals with endometriosis using the 2 outer primers and standard PCR conditions, the presence of an approximately 1.5 kb band confirms the presence of the deletion. The deletion includes a transcription factor binding site.

However, other primers may be employed, e.g., as a pair or in a nested set of primers, to allow for a smaller product to be generated (for more rapid PCR). In one embodiment, the primer pair is capable of generating a diagnostic product even when pooled samples are tested (e.g., the presence of 1/10 individuals with a deletion will result in generation of a product, therefore reporting the presence of at least one deletion within the 10 individuals being tested). This will be a useful screening test, which will allow thousands of individuals to be screened very rapidly (for example, 1,000 individuals can be screened using 100 PCR reactions, each containing DNA from 10 individuals). Any pool that is positive can be 'split' and the individual cases tested singly, in order to identify the individual(s) from whom the band originates. Pools that are negative would not need to be 'split' in this way for further analysis.

Figure 11:
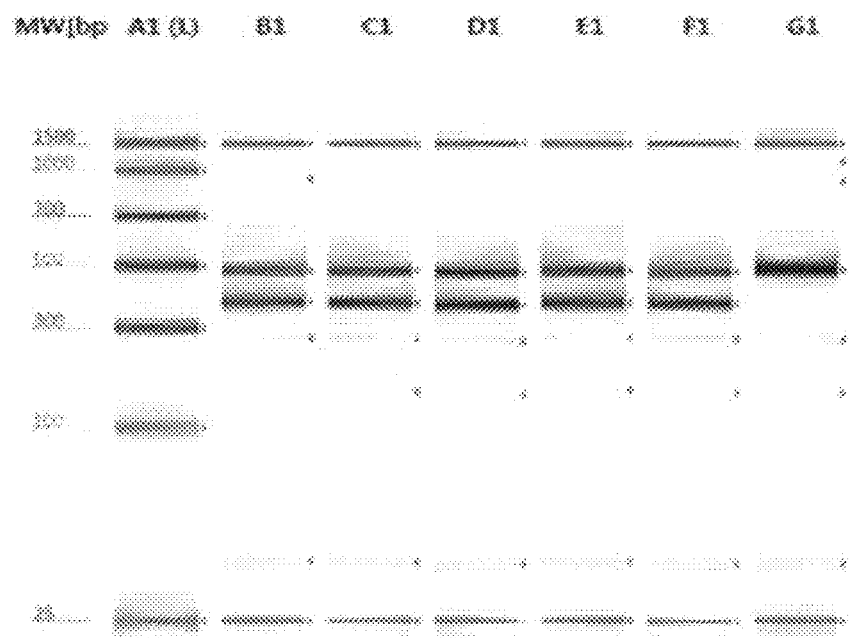
FIG. 11 represents an example of a typical result in a heterozygous deletion carrier and a non-carrier.

For example, using standard PCR conditions, PCR may be performed using a pair of primers designed to generate a product if and only if at least one of the individual's TGFBR3 genes possesses a deletion, for instance, using the primers that yielded the product in FIG. 7. If the band is present, the patient has the deletion, indicating EN or a predisposition or susceptibility thereto. If the band is absent, the patient does not have the deletion and so does not have this marker for EN. In a further refinement of the method to detect the deletion, a new set of primers was designed. The new set of primers, Endo_screen_F= CGAATTCTTTCA-GGGCAACA (SEQ ID NO: 162) and Endo_screen_R= GACAGAGCCCAGCTTTAGGA (SEQ ID NO: 163), generate a product of size 362 bp when the deletion is present. Additionally, a 'control' set of primers was designed to amplify the sequence within the deletion, in order to differentiate del/del homozygotes from del/wt heterozygotes. This 'controls' primer pair was TGFBR3_ internal_F= TTGTGTGGCCTCACTCAAAC (SEQ ID NO: 164) and TGFBR3_internal_R=CCCTTGACTTGCTGTGAGGT- (SEQ ID NO: 165), and generates a 460 bp product when at least one copy of the sequence internal to the deletion is present. The 460 bp 'control' band can be easily differentiated from the 362 bp product created when the deletion is present. Thus, using a combination of both primers in the PCR reaction, there are 3 possible outcomes: 460 bp band only→wt/wt (no deletion); 460 bp+362 bp bands→wt/del (heterozygous deletion is present); 362 bp band only→del/del (homozygous deletion). This primer combination was used to screen a total of 911 endometriosis samples (100 discovery samples plus 811 unrelated individuals). A total of 5 heterozygous deletion carriers were found, 3 from the original discovery cohort of 100 (this represented a technical validation) plus 2 further, new, cases. Thus, the heterozygous deletion was present in a total of 5/911 cases=0.55%. In a total of 2,257 non-endometriosis cases, only one positive was found (in a male for whom no family history is available). Thus, the Fisher's exact test for this deletion is FET=0.0089 and the odds ratio is OR=12.45. FIG. 11 represents an example of a typical result in a heterozygous deletion carrier and a non-carrier (these were the only 2 genotypes seen—no homozygous carriers have been observed but are theoretically predicted to exist, albeit rarely).

Example 5

For each CNV listed in FIG. 1, the relevant intron(s)/exon(s) sequence for the CNV was obtained from the consensus HG18 sequence. The sequences in the files are for complete introns/exons, rather than the specific component relevant to the CNV. CNVs that encompass consecutive introns and exons contain multiple features reported per CNV.

All publications, patents, and patent applications mentioned in this specification are herein incorporated by reference to the same extent as if each individual publication, patent, or patent application was specifically and individually indicated to be incorporated by reference.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11384397B2). An electronic copy of the "Sequence Listing" will also be available from the USPTO upon request and payment of the fee set forth in 37 CFR 1.19(b)(3).

What is claimed is:

1. A method comprising:
   (a) (i) hybridizing a nucleic acid probe to a polynucleic acid, wherein the polynucleic acid is from a sample from a human female subject with endometriosis, or
   (ii) synthesizing a nucleic acid product from a polynucleic acid, wherein the polynucleic acid is from a sample from a human female subject with endometriosis; and
   (b) detecting a genetic variation in the polynucleic acid; wherein detecting comprises detecting by PCR, sequencing, nucleic acid hybridization, microarray analysis, northern blot or a combination thereof,
   wherein the genetic variation is a copy number variation (CNV) of a TSHR gene.

2. The method of claim 1, wherein the CNV comprises the sequence of SEQ ID NO: 26.

3. The method of claim 1, wherein the polynucleic acid sample is isolated from blood, saliva, urine, serum, tears, skin, tissue or hair from the human female subject.

4. The method of claim 1, wherein detecting comprises detecting by multiplex ligation-dependent probe amplification (MLPA), molecular beacon, array Comparative Genomic Hybridization, Invader assay, ligase chain reaction (LCR), fluorescence in situ hybridization, or any combination thereof.

5. The method of claim 1, wherein detecting comprises detecting by whole genome sequencing or whole exome sequencing.

6. The method of claim 1, wherein the method further comprises administering a pharmaceutical composition for treating endometriosis to the subject.

7. The method of claim 1, wherein the human female subject is asymptomatic or is infertile.

8. The method of claim 5, wherein the detecting further comprises an in-silico analysis.

9. The method of claim 1, wherein the detecting comprises detecting a first genetic variation, wherein the first genetic variation is the CNV of the TSHR gene, wherein the first genetic variation and a second genetic variation are in a panel comprising two or more genetic variations.

* * * * *